US007550150B2

(12) United States Patent
Rosenberg et al.

(10) Patent No.: US 7,550,150 B2
(45) Date of Patent: Jun. 23, 2009

(54) METHODS OF TREATING OR PREVENTING A DISEASE, DISORDER OR CONDITION ASSOCIATED WITH A VIRAL INFECTION

(75) Inventors: Barnett Rosenberg, Holt, MI (US); John W. Judge, St. Johns, MI (US)

(73) Assignee: Barros Research Institute, Holt, MI (US)

( * ) Notice: Subject to any disclaimer, the term of this patent is extended or adjusted under 35 U.S.C. 154(b) by 0 days.

(21) Appl. No.: 11/376,656

(22) Filed: Mar. 14, 2006

(65) Prior Publication Data

US 2006/0211027 A1    Sep. 21, 2006

Related U.S. Application Data

(60) Provisional application No. 60/662,135, filed on Mar. 15, 2005.

(51) Int. Cl.
*A61K 39/00* (2006.01)
*A61K 39/002* (2006.01)
*A61K 39/012* (2006.01)
*A61K 49/00* (2006.01)

(52) U.S. Cl. .................. 424/267.1; 424/9.2; 424/185.1; 424/265.1; 424/271.1; 424/273.1

(58) Field of Classification Search ........................ None
See application file for complete search history.

(56) References Cited

U.S. PATENT DOCUMENTS

2005/0058658 A1    3/2005    Rosenberg
2005/0169935 A1    8/2005    Aylsworth et al.

FOREIGN PATENT DOCUMENTS

WO    WO-2005/010040    2/2005
WO    WO-2005/010163    2/2005

OTHER PUBLICATIONS

Charest et al., Recombinant Attenuated *Toxoplasma gondii* Expressing the *Plasmodium yoelii* Circumsporozoite Protein Provides Highly Effective Priming for CD8+ T Cell-Dependant Protective Immunity Against Mice, The Journal of Immunology, Aug. 2000, vol. 165, No. 4, pp. 2084-2092.*
Ding et al., Protective Immunity against *Eimeria acervulina* following In Ovo Immunization with a Recombinant Subunit Vaccine and Cytokine Genes, Infection and Immunity, Dec. 2004, vol. 72, No. 12, pp. 6939-6944.*
Araki et al., Hantavirus-Specific CD8+-T-Cell Responses in Newborn Mice Persistently Infected with Hantaan Virus, Journal of Virology, Aug. 2003, vol. 77, No. 15, pp. 8408-8417.*
Lillehoj, et al. A Recombinant *Eimeria* Protein inducing Inferferon Production: Comparison of Different Gene Expression Systems and Immunization Strategies for Vaccination Against Coccidiosis, Avian Diseases, 2000, vol. 44, No. 2, pp. 379-389.*
Killpatrick et al., Role of Specific CD8+ T Cells in the Severity of a Fulminant Zoonotic Viral Hemorrhagic Fever, Hantavirus Pulmonary Syndrome, The Journal of Immunology, 2004, vol. 172, pp. 3297-3304.*
Julander et al. Prophylactic treatment with recombinant *Eimeria* protein, alone or in combination with an agonist cocktail, protects mice from Banzi virus infection. Antiviral Research, 2007, vol. 75, pp. 14-19.*
Altschul et al., *Nucleic Acids Res.* 1977;2:3389-3402.
Diamond et al, 2003, J Exp Med 198, 1853-62.
Dix et al, 2004, Curr HIV Res 2, 333-42.
Ellermann-Eriksen, 2005, Virol J 2, 59.
Fetterer et al., *J. Parasitol.* 2004;90(6):1321-8.
Fields et al., eds., *Fields Virology*, Third Edition, Lipincott-Raven Publishers, Philadelphia, 1996.
Galasso et al., *Practical Diagnosis of Viral Infections*, Third Edition, 1993, Raven Press, New York.
Ireland et al, 2005, Viral Immunol 18, 397-402.
Aliberti et al., *Immunological Reviews*, 2004;201:26-34.
Koller and Smithies, *Proc. Natl. Acad. Sci.* USA 1989;86:8932-8935.
Korenbaum et al., *Biochemistry* 1998;37(26):9274-83.
Miller et al., *Meth. Enzymol.* 1993;217:581-599.
Reed et al., *Am. J. Hyg.* 1938;27:493-497.
Rollier et al, 2005, J Infect Dis 192, 920-29.
Rosenberg et al., *Int. J. Cancer* 2005;114: 756-765.
Schluter et al., *Biochim Biophys Acta.* 1997;1359(2):97-109.
Sidwell et al., Annals of the New York Academy of Sciences 1992;635:344-355.
Sidwell et al., *Antimicrob Agents Chemother.* 1988;32:331-336.
Singh et al., *Antimicrobial Agents and Chemotherapy* 1989; 33(12): 2126-2131.
Sousa et al., *Immunity*, 1999;11:637-647.
Specter et al., *Clinical Virology Manual*, Third Edition, 2000, ASM Press, Washington D.C.
Zijlstra et al., *Nature* 1989;342:435-438.
Gowen, Bruce B. et al. "Recombinant *Eimeria* Protozoan Protein Elicits Resistance to Acute Phlebovirus Infection in Mice but Not Hamsters" Antimicrobial Agents and Chemotherapy, Jun. 2006, vol. 50, No. 6, pp. 2023-2029.
Gowen, Bruce B. et al. "Use of Protein from an Intestinal Protozoan for the Treatment of Punta Toro Virus Infection in Mice," 2005.
Sidwell, R. "Inhibition of Experimentally Induced Influenza Virus Infections by Barrogen, a Potent New Immunostimulant." Arrival Research, Mar. 2005, vol. 65, No. 3, p. A64.
Charest, H. "Recombinant Attenuated *Toxoplasma gindii* Expressing the *Plasmodium yoelii* Circumsporozoite Protein Provide Highly Effective Priming for CD8 T Cell-Dependent Protective Immunity Against Malaria." The Journal of Immunology, 2000, vol. 165, pp. 2084-2092.

(Continued)

*Primary Examiner*—Bruce Campell
*Assistant Examiner*—Sharon Hurt
(74) *Attorney, Agent, or Firm*—Fish & Richardson P.C.

(57) ABSTRACT

The present invention relates to methods of treating or preventing a disease, disorder or condition associated with a viral infection using a dosing and resting regimen for administering a pharmaceutical composition that provides ARP.

55 Claims, 31 Drawing Sheets

OTHER PUBLICATIONS

Gowen et al., "Immunoprophylaxis of Punta Toro virus (*Phlebovirus, Bunyaviridae*) infection in hamsters with recombinant *Eimeria* profilin-like antigen", *International Immunopharmacology*, vol. 8:1089-1094 (2008).

Gowen et al., "Recombinant *Eimeria* Protozoan Protein Elicits Resistance to Acute Phlebovirus Infection in Mice but Not Hamsters", *Antimicrobial Agents and Chemotherapy*, vol. 50:2023-2029 (2006).

Laurent et al., "*The immunodominant Eimeria acervulina sporozoite anitgen previously described as p160/p240 is a 19-kilodalton antigen present in several Eimeria species*", Molecular and Biochemical Parasitology, Elsivier Science Publishers, Amsterdam, NL, 63(1):79-86 (1994) (Abstract Only).

* cited by examiner $*P<0.05, P<0.01, *P<0.001$

- rBBX-01 (5000 ng/kg/day)
- rBBX-01 (500 ng/kg/day)
- rBBX-01 (50 ng/kg/day)
- rBBX-01 (5 ng/kg/day)
- rBBX-01 (0.5 ng/kg/day)
- Ribavirin (75 ng/kg/day)
- Saline
- Normal Controls

*P<0.05, **P<0.01

| | |
|---|---|
| —■— | rBBX-01

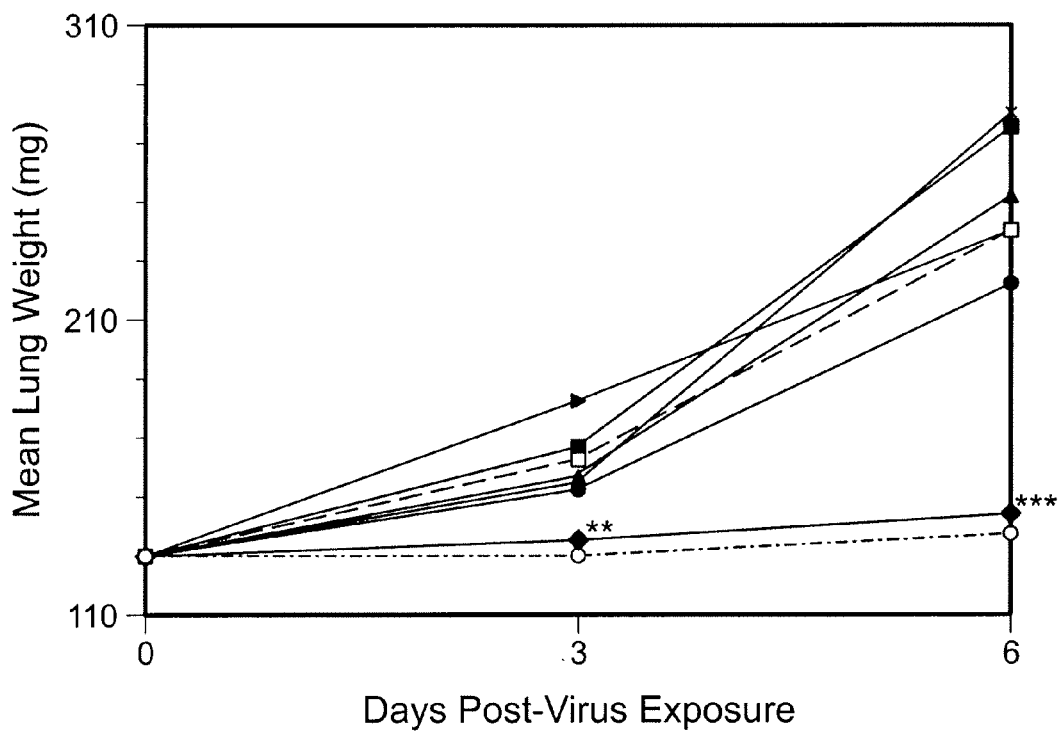
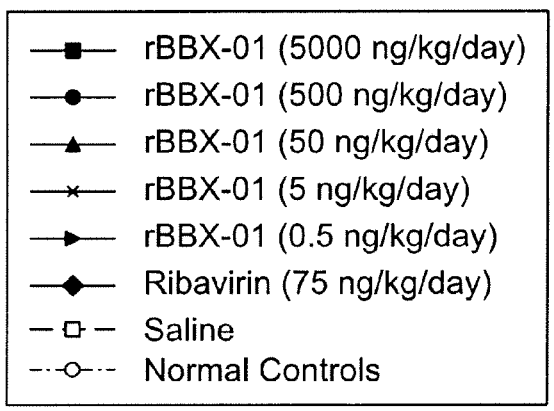
FIG. 3

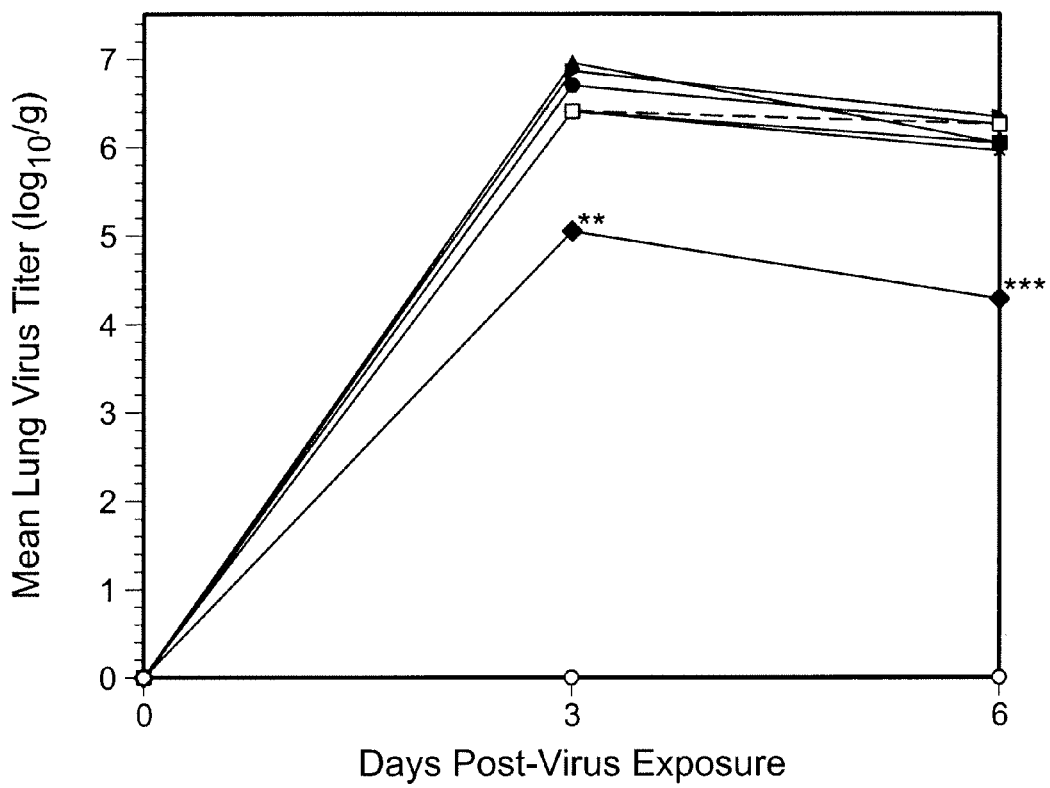
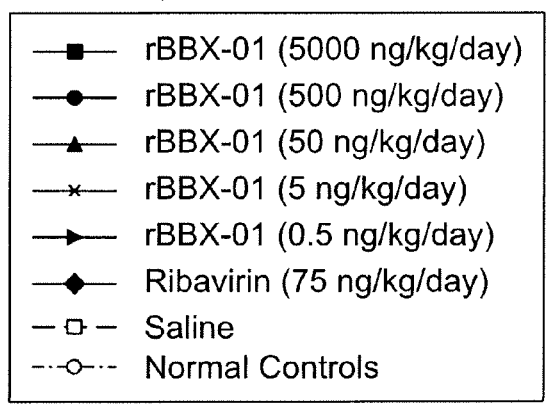
FIG. 4

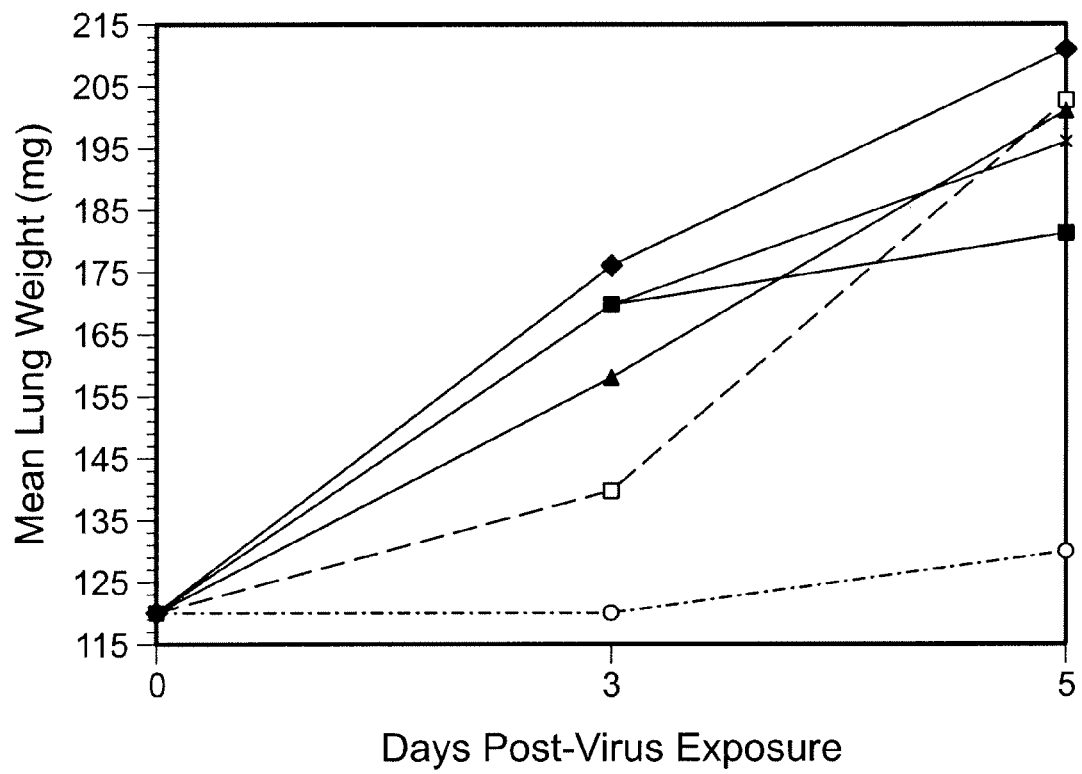
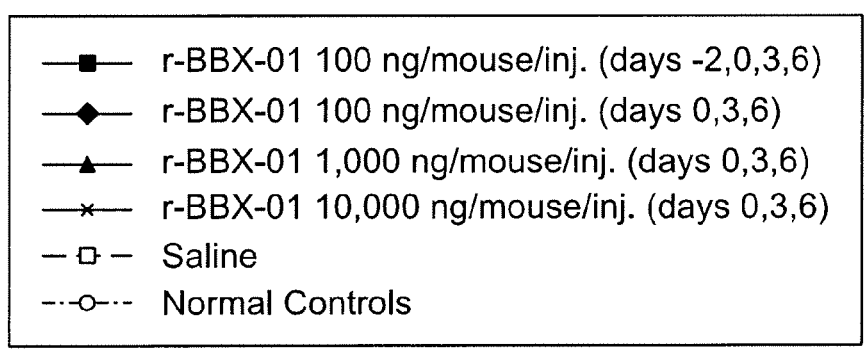
FIG. 7

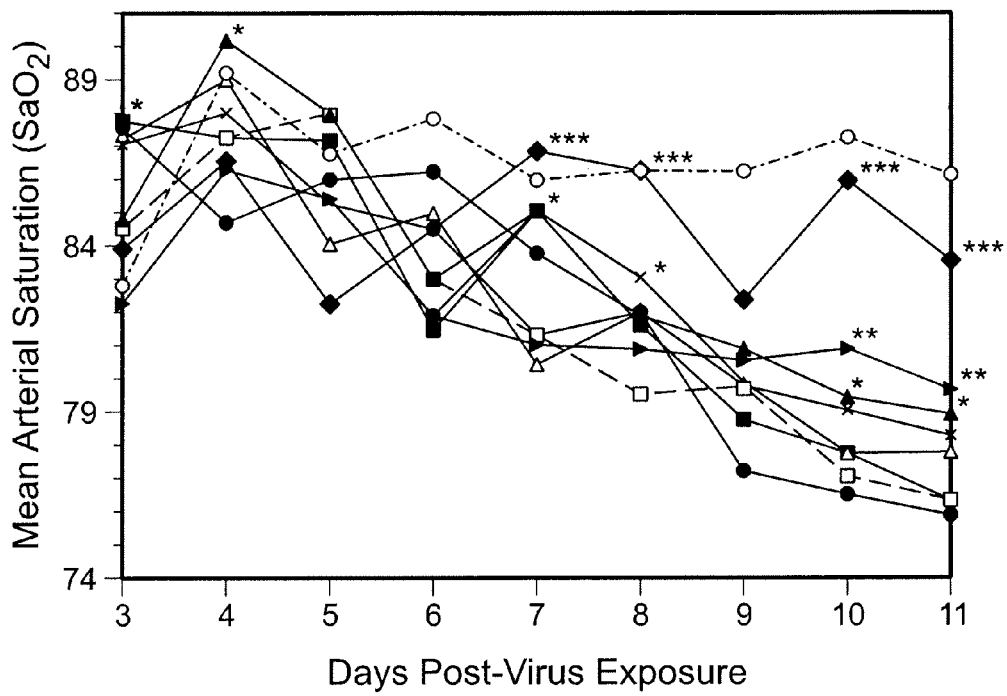
*P<0.05, P<0.01, *P<0.001
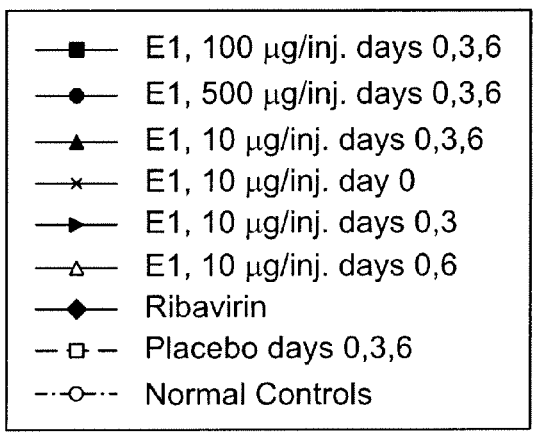
- ■— E1, 100 µg/inj. days 0,3,6
- ●— E1, 500 µg/inj. days 0,3,6
- ▲— E1, 10 µg/inj. days 0,3,6
- ✕— E1, 10 µg/inj. day 0
- ▶— E1, 10 µg/inj. days 0,3
- △— E1, 10 µg/inj. days 0,6
- ◆— Ribavirin
- –□– Placebo days 0,3,6
- ⋯○⋯ Normal Controls
FIG. 9

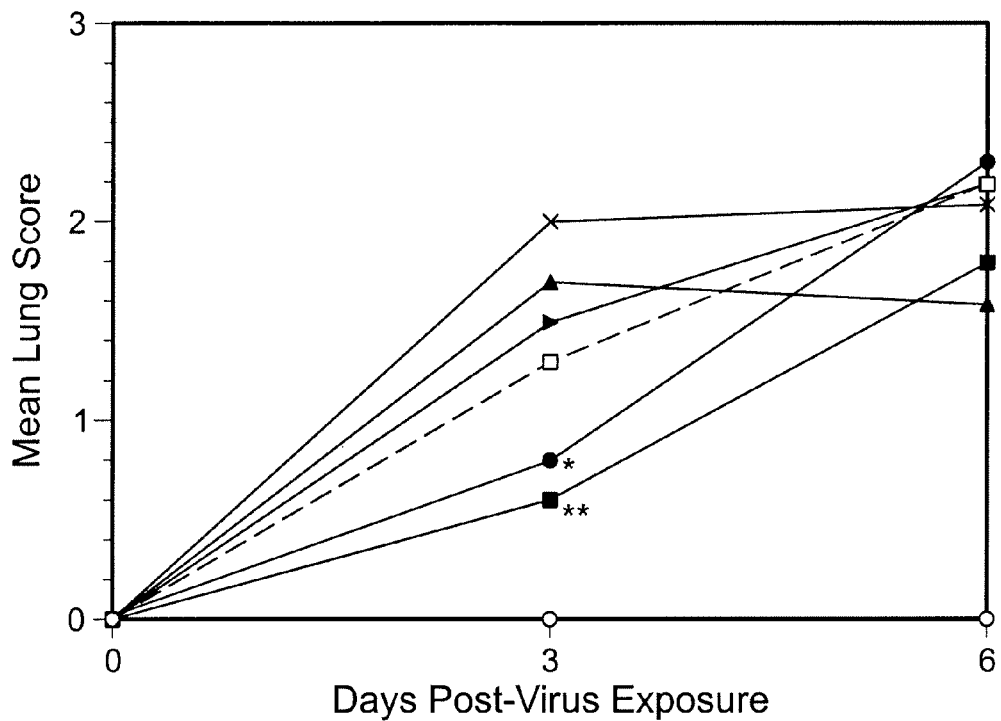
*P<0.05, **P<0.01
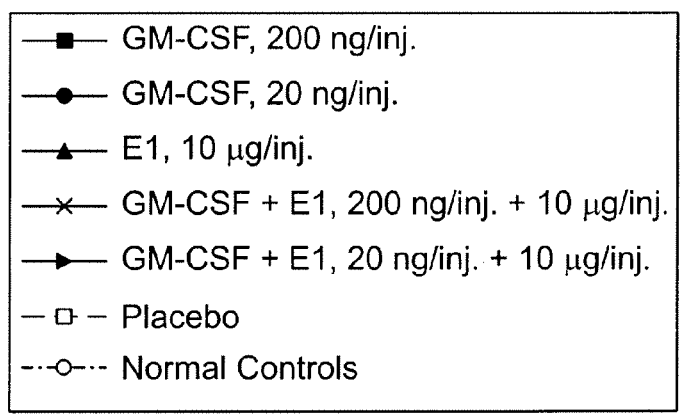
FIG. 14

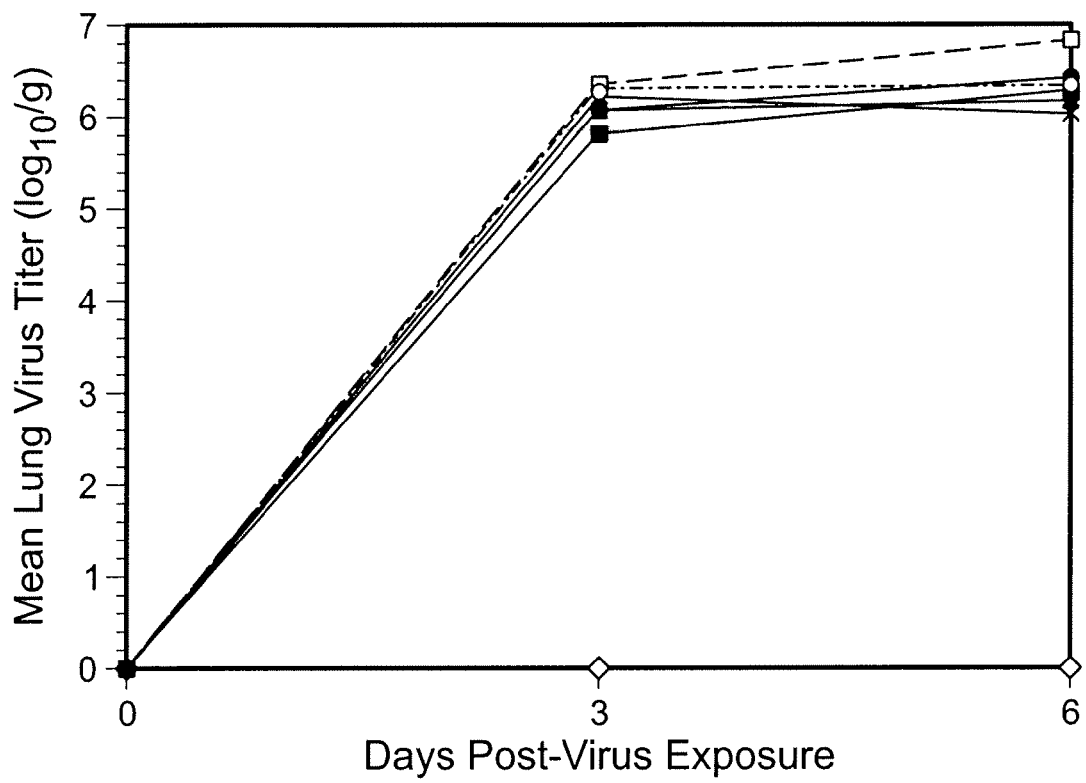
*P<0.05, P<0.01, *P<0.001
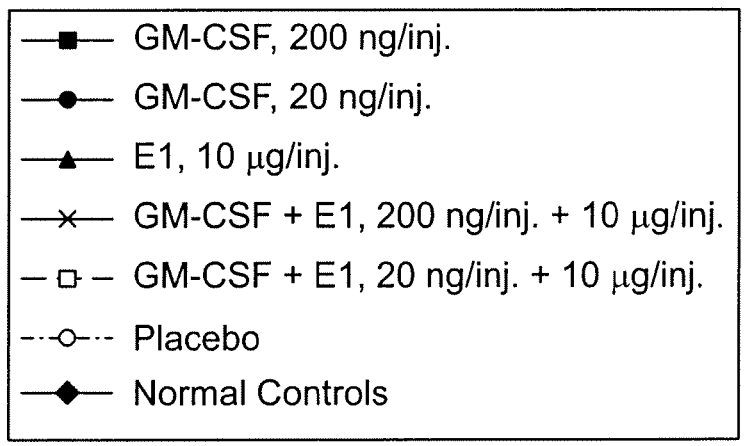
FIG. 16

*P<0.05 Compared to 0.1% BSA/PBS-Treated Controls.

***P<0.001 Compared to 0.1% BSA/PBS-Treated Controls.

*P<0.05 Compared to 0.1% BSA/PBS-Treated Controls.

*P<0.05; ***P<0.001 Compared to 0.1% BSA/PBS-Treated Controls.

```
SEQUENCE LISTING

<160> NUMBER OF SEQ ID NOS: 20

<210> SEQ ID NO 1
<211> LENGTH: 169
<212> TYPE: PRT
<213> ORGANISM: Eimeria tenella

<400> SEQUENCE: 1

Met Gly Glu Ala Asp Thr Gln Ala Trp Asp Thr Ser Val Arg Glu Trp
1               5                   10                  15

Leu Val Asp Thr Gly Arg Val Phe Ala Gly Gly Val Ala Ser Ile Ala
                20                  25                  30

Asp Gly Cys Arg Leu Phe Gly Ala Ala Val Glu Gly Glu Gly Asn Ala
            35                  40                  45

Trp Glu Glu Leu Val Lys Thr Asn Tyr Gln Ile Glu Val Pro Gln Glu
    50                  55                  60

Asp Gly Thr Ser Ile Ser Val Asp Cys Asp Glu Ala Glu Thr Leu Arg
65                  70                  75                  80

Gln Ala Val Val Asp Gly Arg Ala Pro Asn Gly Val Tyr Ile Gly Gly
                85                  90                  95

Thr Lys Tyr Lys Leu Ala Glu Val Lys Arg Asp Phe Thr Phe Asn Asp
                100                 105                 110

Gln Asn Tyr Asp Val Ala Ile Leu Gly Lys Asn Lys Gly Gly Gly Phe
            115                 120                 125

Leu Ile Lys Thr Pro Asn Glu Asn Val Val Ile Ala Leu Tyr Asp Glu
    130                 135                 140

Glu Lys Glu Gln Asn Lys Ala Asp Ala Leu Thr Thr Ala Leu Asn Phe
145                 150                 155                 160
```

Ala Glu Tyr Leu His Gln Ser Gly Phe
            165

<210> SEQ ID NO 2
<211> LENGTH: 170
<212> TYPE: PRT
<213> ORGANISM: Eimeria acervulina

<400> SEQUENCE: 2

Met Gly Glu Glu Ala Asp Thr Gln Ala Trp Asp Thr Ser Val Lys Glu
1               5                   10                  15

Trp Leu Val Asp Thr Gly Lys Val Tyr Ala Gly Ile Ala Ser Ile
                20                  25                  30

Ala Asp Gly Cys Arg Leu Phe Gly Ala Ala Ile Asp Asn Gly Glu Asp
            35                  40                  45

Ala Trp Ser Gln Leu Val Lys Thr Gly Tyr Gln Ile Glu Val Leu Gln
        50                  55                  60

Glu Asp Gly Ser Ser Thr Gln Glu Asp Cys Asp Ala Glu Thr Leu
65                  70                  75                  80

Arg Gln Ala Ile Val Asp Gly Arg Ala Pro Asn Gly Val Tyr Ile Gly
                85                  90                  95

Gly Ile Lys Tyr Lys Leu Ala Glu Val Lys Arg Asp Phe Thr Tyr Asn
            100                 105                 110

Asp Gln Asn Tyr Asp Val Ala Ile Leu Gly Lys Asn Lys Gly Gly Gly
        115                 120                 125

Phe Leu Ile Lys Thr Pro Asn Asp Asn Val Val Ile Ala Leu Tyr Asp
    130                 135                 140

Glu Glu Lys Glu Gln Asn Lys Ala Asp Ala Leu Thr Thr Ala Leu Ala
145                 150                 155                 160

Phe Ala Glu Tyr Leu Tyr Gln Gly Gly Phe
                165                 170

<210> SEQ ID NO 3
<211> LENGTH: 20
<212> TYPE: PRT
<213> ORGANISM: Bovine

<400> SEQUENCE: 3

Glu Trp Leu Val Asp Thr Gly Lys Val Phe Ala Gly Gly Val Ala Ser
1               5                   10                  15

Ile Ala Asp Gly
            20

<210> SEQ ID NO 4
<211> LENGTH: 31
<212> TYPE: PRT
<213> ORGANISM: Bovine

<400> SEQUENCE: 4

Arg Met Phe Gly Ala Ser Thr Asp Ser Gly Gly Asp Pro Asn Ala Glu
1               5                   10                  15

Leu Val Lys Ala Gly Tyr Gln Ile Glu Ser Val Gln Glu Asp Asn
                20                  25                  30

<210> SEQ ID NO 5
<211> LENGTH: 4
<212> TYPE: PRT
<213> ORGANISM: Bovine

```
<400> SEQUENCE: 5

Gln Ala Ile Val
1

<210> SEQ ID NO 6
<211> LENGTH: 11
<212> TYPE: PRT
<213> ORGANISM: Bovine

<400> SEQUENCE: 6

Ala Pro Asp Gly Val Tyr Ile Gly Gly Val Lys
1               5                   10

<210> SEQ ID NO 7
<211> LENGTH: 42
<212> TYPE: PRT
<213> ORGANISM: Bovine

<400> SEQUENCE: 7

Gly Gly Gly Phe Leu Ile Lys Thr Pro Asn Glu Asn Ile Ala Ile Ala
1               5                   10                  15

Leu Tyr Asp Glu Glu Lys Glu Gln Asn Lys Ala Asp Ala Leu Thr Thr
            20                  25                  30

Ala Leu Asn Phe Ala Asp Phe Leu Tyr Gln
        35                  40

<210> SEQ ID NO 8
<211> LENGTH: 131
<212> TYPE: PRT
<213> ORGANISM: Hevea brasiliensis

<400> SEQUENCE: 8

Met Ser Trp Gln Thr Tyr Val Asp Asp His Leu Met Cys Asp Ile Asp
1               5                   10                  15

Gly His Arg Leu Thr Ala Ala Ile Ile Gly His Asp Gly Ser Val
            20                  25                  30

Trp Ala Gln Ser Ser Ser Phe Pro Gln Phe Lys Ser Asp Glu Val Ala
        35                  40                  45

Ala Val Met Lys Asp Phe Asp Glu Pro Gly Ser Leu Ala Pro Thr Gly
    50                  55                  60

Leu His Leu Gly Gly Thr Lys Tyr Met Val Ile Gln Gly Glu Pro Gly
65                  70                  75                  80

Ala Val Ile Arg Gly Lys Lys Gly Ser Gly Gly Ile Thr Val Lys Arg
                85                  90                  95

Thr Gly Gln Ala Leu Ile Ile Gly Ile Tyr Asp Glu Pro Leu Thr Pro
            100                 105                 110

Gly Gln Cys Asn Met Ile Val Glu Arg Leu Gly Asp Tyr Leu Leu Asp
        115                 120                 125

Gln Gly Leu
    130

<210> SEQ ID NO 9
<211> LENGTH: 130
<212> TYPE: PRT
<213> ORGANISM: Arabidopsis thaliana
<220> FEATURE:
<221> NAME/KEY: MISC_FEATURE
<222> LOCATION: (1)..(130)
<223> OTHER INFORMATION: Xaa is any naturally-occurring amino acid

<400> SEQUENCE: 9
```

```
Ser Trp Gln Ser Tyr Val Asp Asp His Leu Xaa Cys Asp Val Glu Gly
 1               5                  10                  15

Asn His Leu Thr Ala Ala Ala Ile Leu Gly Gln Asp Gly Ser Val Trp
             20                  25                  30

Ala Gln Ser Ala Lys Phe Pro Gln Leu Lys Pro Gln Glu Ile Asp Gly
         35                  40                  45

Ile Lys Lys Asp Phe Glu Glu Pro Gly Phe Leu Ala Pro Thr Gly Leu
 50                  55                  60

Phe Leu Gly Gly Glu Lys Tyr Xaa Val Ile Gln Gly Glu Gln Gly Ala
65                   70                  75                  80

Val Ile Arg Gly Lys Lys Gly Pro Gly Val Thr Ile Lys Lys Lys Thr
                 85                  90                  95

Asn Gln Ala Leu Val Phe Gly Phe Tyr Asp Glu Pro Xaa Thr Gly Gly
            100                 105                 110

Gln Cys Asn Leu Val Val Glu Arg Leu Gly Asp Tyr Leu Ile Glu Ser
            115                 120                 125

Glu Leu
    130
```

<210> SEQ ID NO 10
<211> LENGTH: 133
<212> TYPE: PRT
<213> ORGANISM: Betula pendula

<400> SEQUENCE: 10

```
Met Ser Trp Gln Thr Tyr Val Asp Glu His Leu Met Cys Asp Ile Asp
 1               5                  10                  15

Gly Gln Gly Glu Glu Leu Ala Ala Ser Ala Ile Val Gly His Asp Gly
             20                  25                  30

Ser Val Trp Ala Gln Ser Ser Ser Phe Pro Gln Phe Lys Pro Gln Glu
         35                  40                  45

Ile Thr Gly Ile Met Lys Asp Phe Glu Glu Pro Gly His Leu Ala Pro
 50                  55                  60

Thr Gly Leu His Leu Gly Gly Ile Lys Tyr Met Val Ile Gln Gly Glu
65                   70                  75                  80

Ala Gly Ala Val Ile Arg Gly Lys Lys Gly Ser Gly Gly Ile Thr Ile
                 85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
            115                 120                 125

Ile Asp Gln Gly Leu
    130
```

<210> SEQ ID NO 11
<211> LENGTH: 131
<212> TYPE: PRT
<213> ORGANISM: Arabidopsis thaliana

<400> SEQUENCE: 11

```
Met Ser Trp Gln Ser Tyr Val Asp Asp His Leu Met Cys Asp Val Glu
 1               5                  10                  15

Gly Asn His Leu Thr Ala Ala Ala Ile Leu Gly Gln Asp Gly Ser Val
             20                  25                  30

Trp Ala Gln Ser Ala Lys Phe Pro Gln Leu Lys Pro Gln Glu Ile Asp
         35                  40                  45
```

```
Gly Ile Lys Lys Asp Phe Glu Glu Pro Gly Phe Leu Ala Pro Thr Gly
        50                  55                  60

Leu Phe Leu Gly Gly Glu Lys Tyr Met Val Ile Gln Gly Glu Gln Gly
 65                  70                  75                  80

Ala Val Ile Arg Gly Lys Lys Gly Pro Gly Val Thr Ile Lys Lys
                85                  90                  95

Thr Asn Gln Ala Leu Val Phe Gly Phe Tyr Asp Glu Pro Met Thr Gly
            100                 105                 110

Gly Gln Cys Asn Leu Val Val Glu Arg Leu Gly Asp Tyr Leu Ile Glu
        115                 120                 125

Ser Glu Leu
    130

<210> SEQ ID NO 12
<211> LENGTH: 999
<212> TYPE: DNA
<213> ORGANISM: Eimeria acervulina

<400> SEQUENCE: 12
tgtttctctt cattgtttgt agtttctttg tatttcctta ctcagttaaa atgggtgaag      60
aggctgatac tcaggcgtgg gatacctcag tgaaggaatg gctcgtggat acggggaagg    120
tatacgccgg cggcattgct agcattgcag atgggtgccg cctgtttggc gctgcaatag    180
acaatgggga ggatgcgtgg agtcagttgg tgaagacagg atatcagatt gaagtgcttc    240
aagaggacgg ctcttcaact caagaggact gcgatgaagc ggaaaccctg cggcaagcaa    300
ttgttgacgg ccgtgcccca acggtgtttt atattggagg agttaaatat aaactcgcag    360
aagttaaacg tgatttcacc tataacgacc agaactacga cgtggcgatt ttggggaaga    420
acaagggtgg cggtttcctg attaagactc cgaacgacaa tgtggtgatt gctctttatg    480
acgaggagaa ggagcagaac aaagcagatg cgctgacaac ggcacttgcc ttcgctgagt    540
acctgtacca gggcggcttc taattgatct ccagtgcaca accacttgat gagaaggaaa    600
aacctttcat aacaacgact ccccccagt gttaccacac agggagaaga gagacgcaca    660
acttctctac aaatagcgga cagcgtattg cacaccctga cctttgttta ttgaagaggg    720
tgtaggggga ggagcatcag caggcagcag ctttgggcgg tctggacagt cgccatgga    780 gggagagctg tgtagacact cgagagcagc agcagcagca cggttaagtg gcagacgcag    840
agacgccttt gttgtacaac ttctctctca cccgcgtttg ttgtagagag gagtatttat    900
tatgaatgca tatccagcaa acaacgaggc aaacagcggg tgcttactgc cgtgcaaatg    960
atacgcacac caccaaccat ttaataagtg cttttctta                            999

<210> SEQ ID NO 13
<211> LENGTH: 977
<212> TYPE: DNA
<213> ORGANISM: Eimeria acervulina

<400> SEQUENCE: 13
cgtttctttg tatttcctta ctcagttaaa atgggtgaag aggctgatac tcaggcgtgg     60
gatacctcag tgaaggaatg gctcgtggat acggggaagg tatacgccgg cggcattgct   120
agcattgcag atgggtgccg cctgtttggc gctgcaatag acaatgggga ggatgcgtgg   180
agtcagttgg tgaagacagg atatcagatt gaagtgcttc aagaggacgg ctcttcaact   240
caagaggact gcgatgaagc ggaaaccctg cggcaagcaa ttgttgacgg ccgtgcccca   300
```

```
aacggtgttt atattggagg aattaaatat aaactcgcag aagttaaacg tgatttcacc      360
tataacgacc agaactacga cgtggcgatt ttggggaaga acaagggtgg cggtttcctg      420
attaagactc cgaacgacaa tgtggtgatt gctctttatg acgaggagaa agagcagaac      480
aaagcagatg cgctgacaac ggcacttgcc ttcgctgagt acctgtacca gggcggcttc      540
taattgatct ccagtgcaca accacttgat gagaaggaaa aacctttcat aacaacaact      600
tcccccagtg ttgccacaca gggagaagag agacgcacaa cttctctaca aatagcggac      660
agcgtattgc acaccctgac ctttgtttat tgaagagggt gtaggggag gagcatcagc       720 aggcagcagc tttgggcggt ctggacagtt cgccatggag ggagagctgt gtagacactc      780
gagagcagca gcagcagcac ggttaagtgg cagacgcaga gacgcctttg ttgtacaact      840
tctctctcac ccgcgtttgt tgtagagagg agtatttatt atgaatgcat atccagcaaa      900
caacgaggca acagcgggt gcttactgcc gtgcaaatga tacgcacacc accaaccatt       960
taataagtgc ttttctt                                                     977

<210> SEQ ID NO 14
<211> LENGTH: 1074
<212> TYPE: DNA
<213> ORGANISM: Eimeria acervulina

<400> SEQUENCE: 14
ggcacgagtc ttcattgttt gtagtttctt tgtatttcct tactcagtta aaatgggtga      60
agaggctgat actcaggcgt gggatacctc agtgaaggaa tggctcgtgg atacggggaa      120
ggtatacgcc ggcggcattg ctagcattgc agatgggtgc cgcctgtttg gcgctgcaat      180
agacaatggg gaggatgcgt ggagtcagtt ggtgaagaca ggatatcaga ttgaagtgct      240
tcaagaggac ggctcttcaa ctcaagagga ctgcgatgaa gcggaaaccc tgcggcaagc      300
aattgttgac ggccgtgccc caaacggtgt ttatattgga ggaattaaat ataaactcgc      360
agaagttaaa cgtgatttca cctataacga ccagaactac gacgtggcga ttttggggaa      420
gaacaagggt ggcggttttcc tgattaagac tccgaacgac aatgtggtga ttgctctctta     480 tgacgaggag aaagagcaga acaaagcaga tgcgctgaca acggcacttg ccttcgctga     540
gtacctgtac cagggcggct tctaattgat ctccagtgca caaccacttg atgagaagga      600
aaaacctttc ataacaacaa cttccccag tgttgccaca cagggagaag agagacgcac       660
aacttctcta caaatagcgg acagcgtatt gcacaccctg acctttgttt attgaagagg      720
gtgtaggggg aggagcatca gcaggcagca gctttgggcg gtctggacag ttcgccatgg      780
agggagagct gtgtagacac tcgagagcag cagcagcagc acggttaagt ggcagacgca      840
gagacgcctt tgttgtacaa cttctctctc acccgcgttt gttgtagaga ggagtattta      900
ttatgaatgc atatccagca acaacgagg caaacagcgg gtgcttactg ccgtgcaaat       960
gatacgcaca ccaccaacca tttaataagt gcttttctta atatggcttg acgctcccag     1020
cgaaaaaaaa aaaaaaaaaa aaaaaaaaaa aaaaaaaaaa aaaaaaaaaa aaaa           1074

<210> SEQ ID NO 15
<211> LENGTH: 460
<212> TYPE: DNA
<213> ORGANISM: Eimeria acervulina
<220> FEATURE:
<221> NAME/KEY: misc_feature
<222> LOCATION: (240)..(241)
<223> OTHER INFORMATION: n is a, c, t, or g

<400> SEQUENCE: 15
```

```
tgttgacggc cgtgccccaa acggtgttta tattggagga gttaaatata aactcgcaga      60
agttgtaagt ttccttcata ctctagaaga atagcgcttg ctcatccatg gtgtcgtgca     120
gtgggatgca atcgccacgc ggggctgtac agacacctca aagttgaatg gtagtaataa     180
tagtcatgtt cttcatgatg atggaataag tgaataatta gggtgttttg tgacggcgtn     240 ntcgctttt tgtcattttc gtcgtttctc ttttgtttat ttcgggccga tgatgcagaa      300
acgtgatttc acctataacg accagaacta cgacgtggcg attttgggga agaacaaggg     360
tggcggtttc ctgattaaga ctccgaacga caatgtggtg attgctcttt atgacgagga     420
gaaggagcag aacaaagcag atgcgctgac aacgcacccc                           460

<210> SEQ ID NO 16
<211> LENGTH: 529
<212> TYPE: DNA
<213> ORGANISM: Eimeria tenella
<220> FEATURE:
<221> NAME/KEY: misc_feature
<222> LOCATION: (406)..(406)
<223> OTHER INFORMATION: n is a, c, t, or g

<400> SEQUENCE: 16
ttattttcta tttagtttgc aaaatgggag aagcagacac ccagcctggg acacttcggt      60
ccgcgagtgg ctggttgaca ccggcagggt cttcgccggc ggcgttgcta gcatagccga     120
cggctgccgg ctcttcggag cagcagtgga gggcgagggc aacgcctggg aagaactcgt     180
caagaccaac taccaaattg aagtccccca ggaagacgga acctccattt cagtggattg     240
cgacgaggcc gagactctgc ggcaggcggt ggtggacggc cgcgcgccca acggcgtcta     300
catcggcggc accaagtaca agctcgccga agtcaaaagg gacttcacct tcaacgacca     360
aaactatgat gtggcgattc tgggaaaaaa caaaggcgga gggttnttga ttaaaactcc     420
aaacgaaaat gttgttatag ctttgtatga tgaagaaaaa gaacataaca aagctgatgc     480
tctcacaaca gctcttaact cgcggagta tctgtaccaa ggaagcttc                  529

<210> SEQ ID NO 17
<211> LENGTH: 558
<212> TYPE: DNA
<213> ORGANISM: Eimeria tenella

<400> SEQUENCE: 17
tccagttttt gctttctttt ccaaattatt ttctatttag tttgcaaaat gggagaagca      60
gacacccagg cctgggacac ttcggtccgc gagtggctgg ttgacaccgg cagggtcttc     120 gccgcggcg ttgctagcat agccgacggc tgccggctct tcggagcagc agtggagggc     180
gagggcaacg cctgggaaga actcgtcaag accaactacc aaattgaagt cccccaggaa     240 gacgaacct ctatttcagt ggattgcgac gaggcggaga ctctgcggca ggcggtggtg     300
gacggccgcg cgcccaacgg cgtctacatc ggcggcacca agtacaagct cgccgaagtc     360 aaagggact tcaccttcaa cgaccaaaac tatgatgtgg cgattctggg aaaaaacaaa     420
ggcggagggt ttttgattaa aactccaaac gaaaatgttg ttatagcttt gtatgatgaa     480 gaaaagaac aaaacaaagc tgatgctctc acaacagctc ttaacttcgc ggagtacctt     540
caccagtccg gcttctaa                                                  558

<210> SEQ ID NO 18
<211> LENGTH: 513
<212> TYPE: DNA
```

<213> ORGANISM: Eimeria tenella

<400> SEQUENCE: 18

```
atgggtgaag aggctgatac tcaggcctgg gacacttcgg tccgcgagtg gctggttgac    60
accggcaggg tcttcgccgg cggcgttgct agcatagccg acggctgccg gctcttcgga   120
gcagcagtgg agggcgaggg caacgcctgg aagaactcg tcaagaccaa ctaccaaatt    180
gaagtccccc aggaagacgg aacctctatt tcagtggatt gcgacgaggc ggagactctg   240
cggcaggcgg tggtggacgg ccgcgcgccc aacggcgtct acatcggcgg caccaagtac   300
aagctcgccg aagtcaaaag ggacttcacc ttcaacgacc aaaactatga tgtggcgatt   360
ctgggaaaaa acaaaggcgg agggtttttg attaaaactc caaacgaaaa tgttgttata   420
gctttgtatg atgaagaaaa agaacaaaac aaagctgatg ctctcacaac agctcttaac   480
ttcgctgagt acctgtacca gggcggcttc taa                                513
```

<210> SEQ ID NO 19
<211> LENGTH: 170
<212> TYPE: PRT
<213> ORGANISM: Eimeria tenella

<400> SEQUENCE: 19

```
Met Gly Glu Glu Ala Asp Thr Gln Ala Trp Asp Thr Ser Val Arg Glu
  1               5                  10                  15

Trp Leu Val Asp Thr Gly Arg Val Phe Ala Gly Gly Val Ala Ser Ile
             20                  25                  30

Ala Asp Gly Cys Arg Leu Phe Gly Ala Ala Val Glu Gly Glu Gly Asn
         35                  40                  45

Ala Trp Glu Glu Leu Val Lys Thr Asn Tyr Gln Ile Glu Val Pro Gln
     50                  55                  60

Glu Asp Gly Thr Ser Ile Ser Val Asp Cys Asp Glu Ala Glu Thr Leu
 65                  70                  75                  80

Arg Gln Ala Val Val Asp Gly Arg Ala Pro Asn Gly Val Tyr Ile Gly
                 85                  90                  95

Gly Thr Lys Tyr Lys Leu Ala Glu Val Lys Arg Asp Phe Thr Phe Asn
            100                 105                 110

Asp Gln Asn Tyr Asp Val Ala Ile Leu Gly Lys Asn Lys Gly Gly Gly
        115                 120                 125

Phe Leu Ile Lys Thr Pro Asn Glu Asn Val Val Ile Ala Leu Tyr Asp
    130                 135                 140

Glu Glu Lys Glu Gln Asn Lys Ala Asp Ala Leu Thr Thr Ala Leu Asn
145                 150                 155                 160

Phe Ala Glu Tyr Leu Tyr Gln Gly Gly Phe
                165                 170
```

<210> SEQ ID NO 20
<211> LENGTH: 169
<212> TYPE: PRT
<213> ORGANISM: Eimeria tenella

<400> SEQUENCE: 20

```
Gly Glu Glu Ala Asp Thr Gln Ala Trp Asp Thr Ser Val Arg Glu Trp
  1               5                  10                  15

Leu Val Asp Thr Gly Arg Val Phe Ala Gly Gly Val Ala Ser Ile Ala
             20                  25                  30

Asp Gly Cys Arg Leu Phe Gly Ala Ala Val Glu Gly Glu Gly Asn Ala
         35                  40                  45
```

-continued

```
Trp Glu Glu Leu Val Lys Thr Asn Tyr Gln Ile Glu Val Pro Gln Glu
    50                  55                  60

Asp Gly Thr Ser Ile Ser Val Asp Cys Asp Glu Ala Glu Thr Leu Arg
65                  70                  75                  80

Gln Ala Val Val Asp Gly Arg Ala Pro Asn Gly Val Tyr Ile Gly Gly
                85                  90                  95

Thr Lys Tyr Lys Leu Ala Glu Val Lys Arg Asp Phe Thr Phe Asn Asp
            100                 105                 110

Gln Asn Tyr Asp Val Ala Ile Leu Gly Lys Asn Lys Gly Gly Gly Phe
        115                 120                 125

Leu Ile Lys Thr Pro Asn Glu Asn Val Val Ile Ala Leu Tyr Asp Glu
    130                 135                 140

Glu Lys Glu Gln Asn Lys Ala Asp Ala Leu Thr Thr Ala Leu Asn Phe
145                 150                 155                 160

Ala Glu Tyr Leu Tyr Gln Gly Gly Phe
                165
```

METHODS OF TREATING OR PREVENTING A DISEASE, DISORDER OR CONDITION ASSOCIATED WITH A VIRAL INFECTION

FIELD OF THE INVENTION

The present invention relates to methods of treating or preventing a disease, disorder or condition associated with a viral infection using a dosing and resting regimen for administering a pharmaceutical composition that provides ARP.

BACKGROUND OF THE INVENTION

A molecule of low abundance from bovine small intestine was identified as a potent immunostimulant and associating with the natural suppression of cancer in the intestinal tract. The protein originates from an endemic gut protozoan, *Eimeria* spp., and is homologous to the antigen 3-1E previously isolated from the avian apicomplexan *E. acervulina* (Rosenberg et al., *Int. J. Cancer* 2005; 114: 756-765). Methods of purifying this molecule and its use in immune stimulation were previously disclosed (see, e.g., PCT publication WO 2005/010163 and PCT publication WO 2005/010040). A similar 19-kDa antigen has been identified as being a profilin-like protein (Fetterer et al., *J. Parasitol.* 2004; 90(6): 1321-8).

Antibiotics have been successfully utilized to treat various bacterial infections in subjects. Viral infections in subjects, however, have been more challenging to treat or prevent. Even though there are several anti-viral agents available on the market, most often these agents do not provide a successful treatment or prevention. There remains a need in the field for a broad-spectrum anti-viral agent that can treat/prevent/cure many different viral infections in subjects through activating the immune system. The present invention addresses this and other needs in the art.

SUMMARY OF THE INVENTION

An object of the present invention is to provide a method for treating or preventing a disease, disorder or condition associated with a viral infection in a subject by administering a therapeutically or prophylactically effective amount of a pharmaceutical composition that provides Apicomplexa related protein (ARP). The invention achieves anti-viral activity by employing a dosing and resting dosage regimen of the ARP. In one embodiment, the therapeutically or prophylactically effective amount of the pharmaceutical composition that provides ARP is in the range of from 0.0001 to 100 μg per kg body weight of the subject. In a specific aspect of the invention, the dosages by weight of an ARP refer to the ARP termed "Barrogen" herein (SEQ ID NO: 20). In embodiments involving another ARP, the dosage can be calculated to be equivalent either in number of molecules or in activity to the stated dose in weight based on Barrogen. According to the invention, the therapeutically or prophylactically effective amount of the pharmaceutical composition that provides ARP is administered using a dosing and resting regimen, e.g., starting on the day of infection or onset of a symptom associated with the viral infection.

In a specific embodiment, the therapeutically or prophylactically effective amount of the pharmaceutical composition that provides ARP is in a range selected from the group consisting of 0.0005-0.001, 0.001-0.01, 0.01-0.1, 0.1-1, 1-10, and 10-100 μg per kg body weight of the subject.

In another specific embodiment, the therapeutically or prophylactically effective amount of the pharmaceutical composition that provides ARP is in the range of from 0.0001-0.001 μg per kg body weight of the subject. In a specific embodiment, the therapeutically or prophylactically effective amount of the pharmaceutical composition that provides ARP is 0.00014 μg per kg body weight of the subject, particularly in an embodiment in which the subject is a human or other primate.

In a specific embodiment, the therapeutically or prophylactically effective amount of the pharmaceutical composition that provides ARP is administered to the subject at least once within a week of the day of infection or the onset of a symptom associated with the viral infection.

In one embodiment, the dosing and resting regimen is once weekly for at least a month starting on the day of infection or the onset of a symptom associated with a chronic-type infection.

In another embodiment, the dosing and resting regimen comprises a first dose administered to the subject daily for a week starting on the day of infection or the onset of a symptom associated with a chronic viral infection, followed by a one week period of no treatment. A further dosage series is administered to the subject daily for a week at least once every other week after administration of the first dose.

In yet another embodiment, the dosing and resting regimen comprises a first dose administered to the subject on the day of infection or the onset of a symptom associated with an acute viral infection and a second and any further doses administered to the subject at least once every 3 days after administration of the first dose.

According to the present invention, the therapeutically or prophylactically effective amount of the pharmaceutical composition that provides ARP is administered to a subject intraperitoneally, intranasally, or subcutaneously.

In one embodiment, the therapeutically or prophylactically effective amount of the pharmaceutical composition that provides ARP is administered conjointly with a therapeutically or prophylactically effective amount of at least one immunostimulatory agent. In a preferred embodiment, at least one immunostimulatory agent is GM-CSF or IL-18. Other Th1 immunostimulatory agents can also be used, such as but not limited to G-CSF, an agonistic anti-CD40 monoclonal antibody ("anti-CD40"), IFN-γ, FLT-3 ligand, IFN α/ß, TNF-α/β, MCP-1, IL-1, IL-2, IL-4, IL-6, and soluble CD40 ligand (i.e., soluble CD 154). In a preferred embodiment, the immunostimulatory agent is a cocktail of at least two, three, or four of the foregoing immunostimulatory molecules. In another preferred embodiment, such a cocktail of agonists administered conjointly with ARP (e.g. Barrogen) comprises or consists of GM-CSF, IL-4, IFN-γ, and anti-CD40.

In one embodiment, the therapeutically or prophylactically effective amount of one or more immunostimulatory agents is in a range selected from the group consisting of 0.001-0.01, 0.01-0.1, 0.1-1, 1-10, 10-100, 100-1000, 1000-10000, and 10000-100000 μg per kg body weight of the subject. Exemplary routes of administration for an immunostimulatory agent according to the present invention are intraperitoneal, intranasal, subcutaneously, intramuscularly, intravenously, orally, or rectally. Any route of administration already employed for the particular immunostimulatory agent is useful in this invention.

In a specific embodiment, the therapeutically or prophylactically effective amount of the pharmaceutical composition that provides ARP is administered to a subject for treating or preventing a disease, disorder or condition associated with a virus in the Orthomyxoviridae family, e.g., an Influenza A infection.

In another specific embodiment, the therapeutically or prophylactically effective amount of the pharmaceutical composition that provides ARP is administered to a subject for treating or preventing a disease, disorder or condition associated with a virus in the Flaviviridae family, e.g., the Flavivirus genus. In one embodiment the virus is Yellow Fever virus, Dengue virus or West Nile virus. In an exemplary embodiment, the virus is Banzi virus.

In yet another specific embodiment, the therapeutically or prophylactically effective amount of the pharmaceutical composition that provides ARP is administered to a subject for treating or preventing a disease, disorder or condition associated with a virus in the Bunyaviridae family, e.g., the Phlebovirus genus. In one embodiment the virus is Rift Valley Fever virus or Sandfly Fever virus. In an exemplary embodiment, the virus is Punta Toro virus.

In another embodiment, the therapeutically or prophylactically effective amount of the pharmaceutical composition that provides ARP is administered to a subject for treating or preventing a disease, disorder or condition associated with a virus in the Paramyxoviridae family, e.g., a parainfluenza-3 virus infection.

In another embodiment, the therapeutically or prophylactically effective amount of the pharmaceutical composition that provides ARP is administered to a subject for treating or preventing a disease, disorder or condition associated with a virus in the Rhabdoviridae family, e.g., a rabies virus infection.

Another object of the present invention is to provide a method for treating or preventing a disease, disorder or condition associated with a viral infection by administering an amount of a pharmaceutical composition that provides ARP using a dosing and resting regimen to effectively cure at least 70% of subjects in a population of at least ten subjects. In one embodiment, at least 90% of subjects in the population of at least ten subjects are cured. In another embodiment, 100% of subjects in the population of at least ten subjects are cured.

In one embodiment, the effective amount of the pharmaceutical composition that provides ARP activates an immune response characterized by IL-12 release from dendritic cells.

In another specific embodiment, subjects having the disease, disorder or condition associated with a virus in the Orthomyxoviridae family are treated. In a specific embodiment, subjects having the disease, disorder or condition associated with Influenza A infection are cured.

In another specific embodiment, subjects having the disease, disorder or condition associated with a virus in the Flaviviridae family are treated. For example, the data show that Flavivirus infections are cured. In one embodiment, the virus is Yellow Fever virus, Dengue virus or West Nile virus. In a specifically exemplified embodiment, the virus is Banzi virus.

In another specific embodiment, subjects having the disease, disorder or condition associated with a virus in the Bunyaviridae family are treated. For example, data show that Phlebovirus infections are cured. In one embodiment, the virus is Rift Valley Fever virus or Sandfly Fever virus. In a specifically exemplified embodiment, the virus is Punta Toro virus.

| Conventions and Abbreviations | |
|---|---|
| ARP | Apicomplexa-related protein |
| GM-CSF | Granulocyte macrophage - colony stimulating factor |
| rBBX-01 or E1 | Barrogen |
| IL-18 | Interleukin 18 |
| i.p. | intraperitoneal or intraperitoneally |

| -continued | |
|---|---|
| Conventions and Abbreviations | |
| i.n. | intranasal or intranasally |
| h | hour or hours |
| spp. | Species |
| SI | small intestine |
| LPS | lipopolysaccharide |
| HIV | Human Immunodeficiency virus |
| PTV | Punta Toro virus |

BRIEF DESCRIPTION OF THE FIGURES

FIGS. 1, 5, 9. Effect of varying i.p. treatment schedules and/or dosages with recombinant rBBX-01 on arterial oxygen saturation ($SaO_2$) decline in Influenza A (H1N1) virus infected mice. Mean Arterial Saturation percentage is shown on the y-axis. Days post-virus exposure is shown on the x-axis. Keys for lines representing normal controls, saline and different concentrations of rBBX-01 are shown. *,  and * represent different P-values.

FIGS. 2, 6, 10. Effect of varying i.p. treatment schedules and/or dosages with rBBX-01 on lung scores in Influenza A (H1N1) virus-infected mice. Mean lung score is shown on the Y-axis. Days post-virus exposure is shown on the x-axis. Keys for lines representing normal controls, saline, different concentrations of rBBX-01 and placebo days, if applicable, are shown. * and ** represent different P-values.

FIG. 3, 7, 11. Effect of varying i.p. treatment dosages and/or schedules with rBBX-01 on lung weight in Influenza A (H1N1) virus-infected mice. Mean lung weight in miligrams is shown on the y-axis. Days post-virus exposure is shown on the x-axis. Keys for lines representing normal controls, saline, different concentrations of rBBX-01 and placebo days, if applicable, are shown.  and * represent different P-values.

FIGS. 4, 8, 12. Effect of varying i.p. treatment dosages and/or schedules with rBBX-01 on lung virus titers in Influenza A (HN1) virus-infected mice. Mean lung virus titer in $log_{10}$/grams is shown on the y-axis. Days post-virus exposure is shown on the x-axis. Keys for lines representing normal controls, saline, different concentrations of rBBX-01 and placebo days, if applicable, are shown. *,  and * represent different P-values.

FIG. 13. Effect of i.p. treatment with E1 alone and combined with GM-CSF on arterial oxygen saturation decline in Influenza virus infected mice. Mean Arterial Saturation percentage is shown on the y-axis. Days post-virus exposure is shown on the x-axis. Keys for lines representing normal controls, placebo and different concentrations of E-1 alone, GM-CSF alone or E-1 and GM-CSF combined are shown. * represents the P-value.

FIG. 14. Effect of i.p. treatment with E1 alone and combined with GM-CSF on lung scores in Influenza A (H1N1) virus-infected mice. Mean lung score is shown on the Y-axis. Days post-virus exposure is shown on the x-axis. Keys for lines representing normal controls, placebo, different concentrations of E1 alone, GM-CSF alone or E1 and GM-CSF combined are shown. * and ** represent different P-values.

FIG. 15. Effect of i.p. treatment with E1 alone and combined with GM-CSF on lung weights in Influenza A (H1N1) virus-infected mice. Mean lung weight in miligrams is shown on the y-axis. Days post-virus exposure is shown on the x-axis. Keys for lines representing normal controls, placebo, different concentrations of E1 alone, GM-CSF alone or E1 and GM-CSF combined are shown.

FIG. 16. Effect of i.p. treatment with E1 alone and combined with GM-CSF on lung virus titers in influenza (H1N1) virus-infected mice. Mean lung virus titer in $\log_{10}$/grams is shown on the y-axis. Days post-virus exposure is shown on the x-axis. Keys for lines representing normal controls, placebo, different concentrations of E1 alone, GM-CSF alone or E1 and GM-CSF combined are shown. *,  and * represent different P-values.

Figure 1:
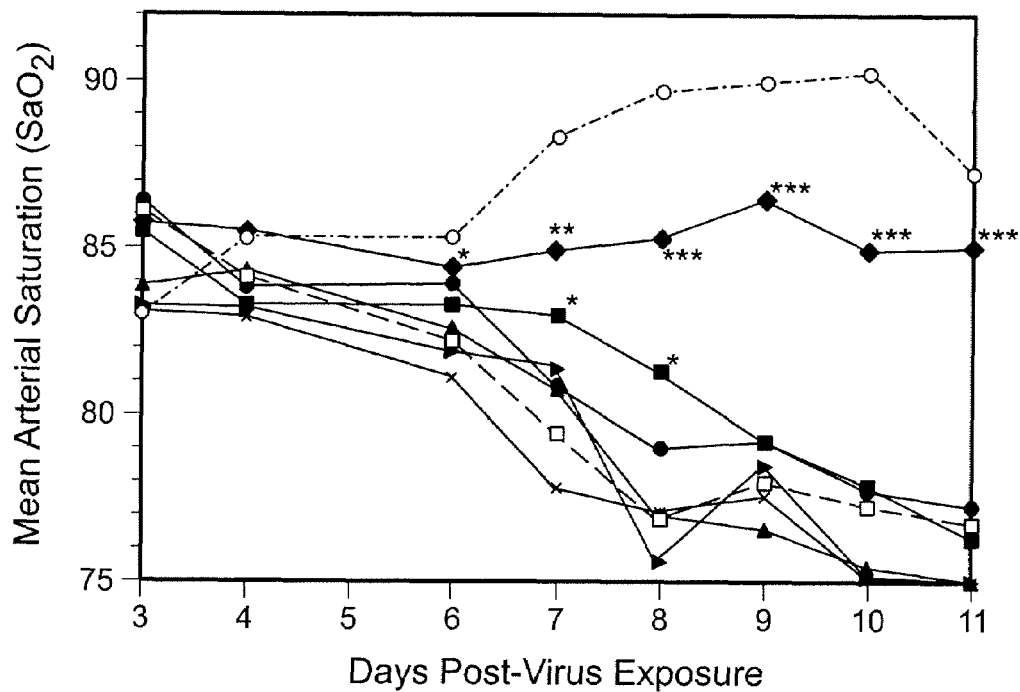
Figure 2:
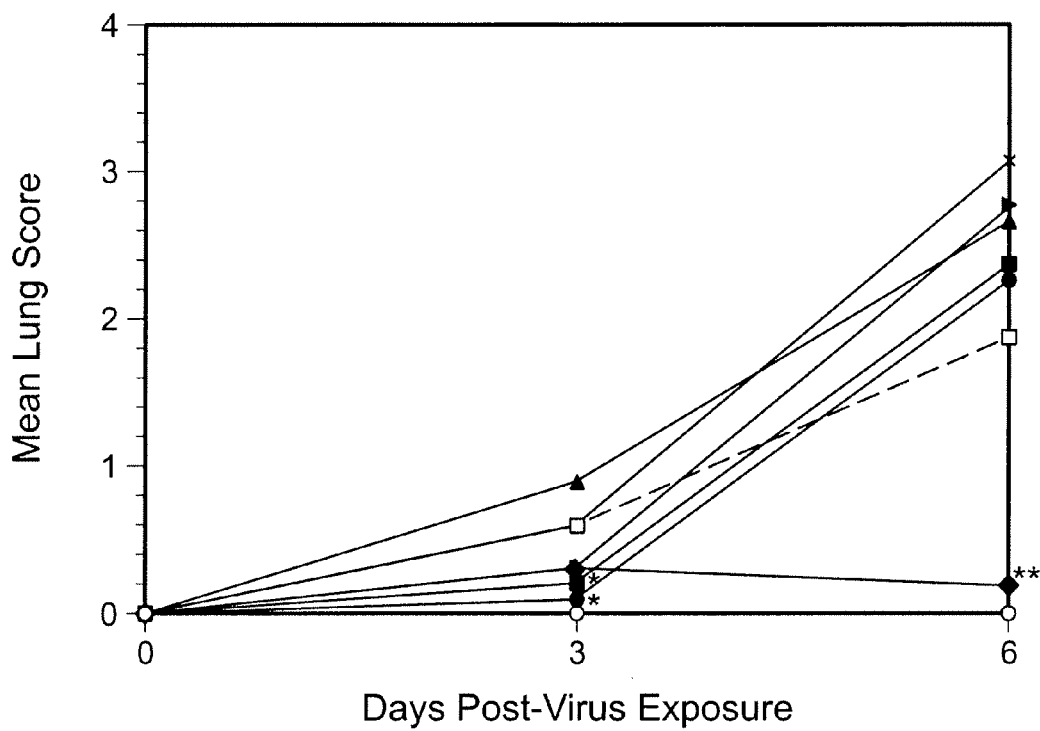
Figure 5:
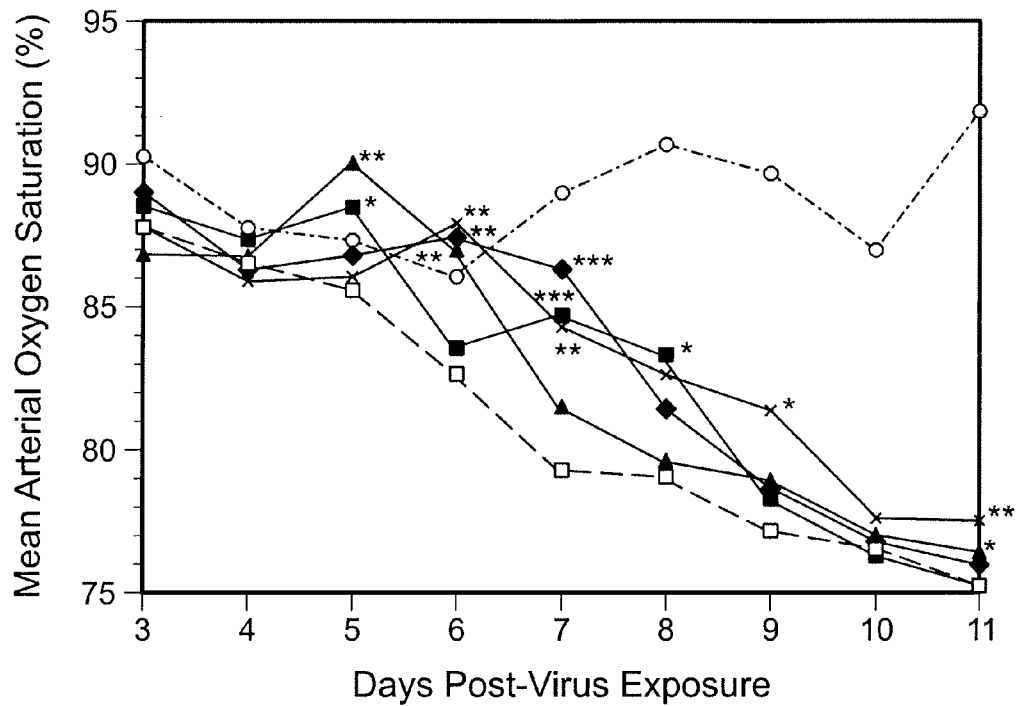
Figure 6:
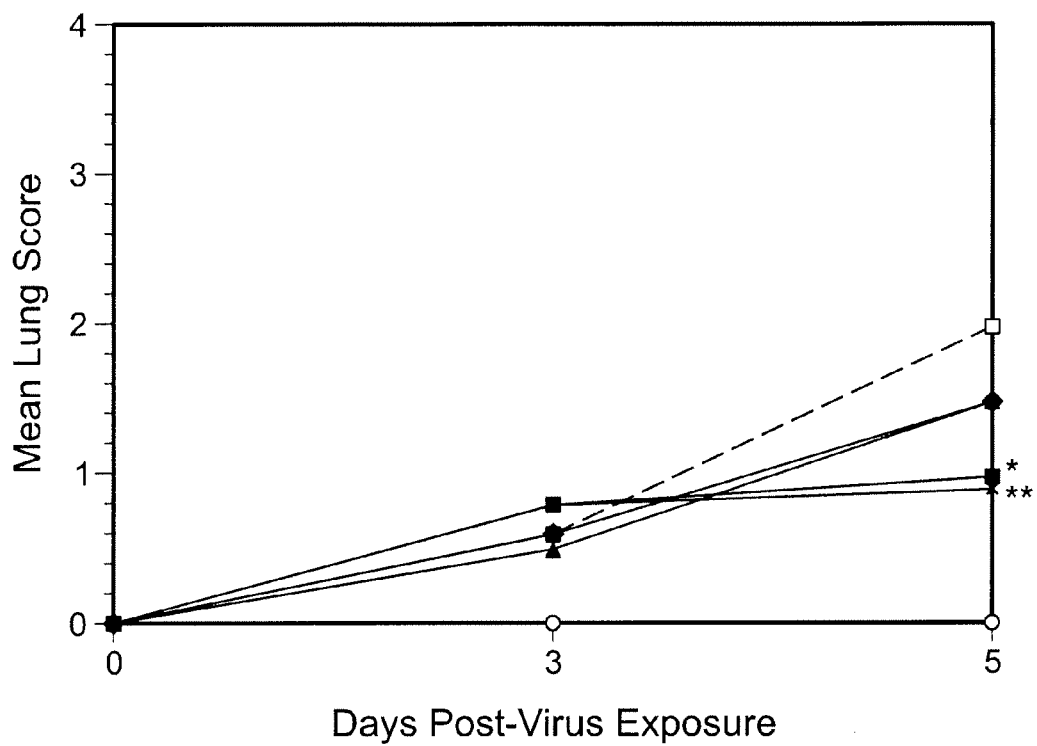
Figure 8:
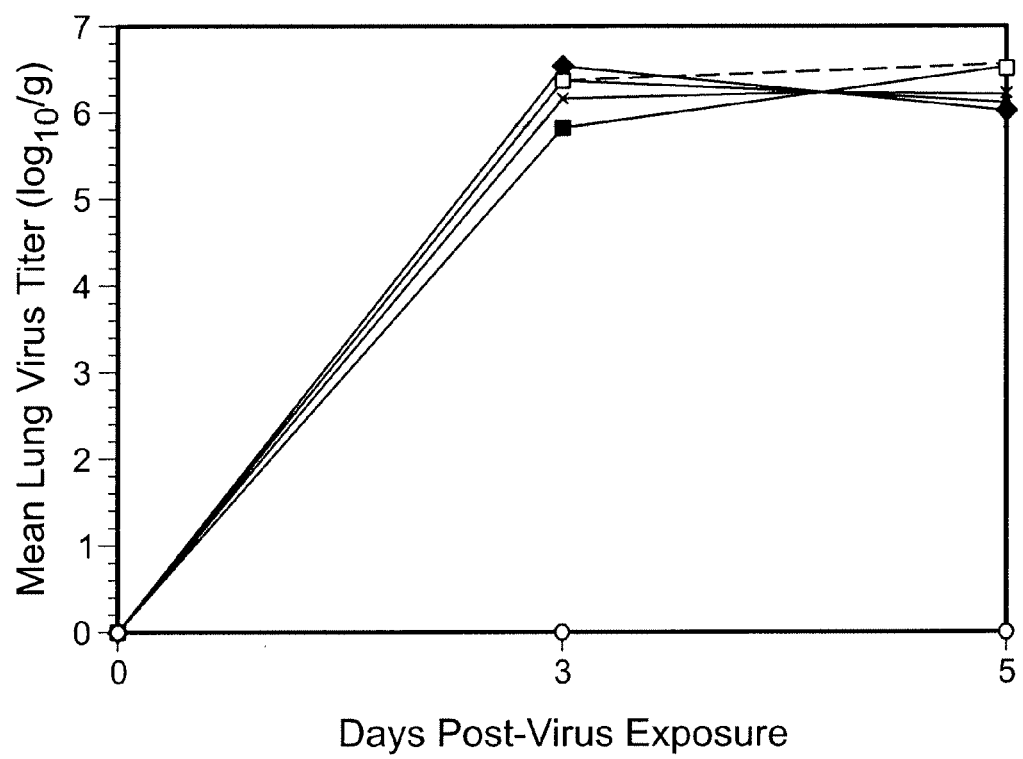
Figure 10:
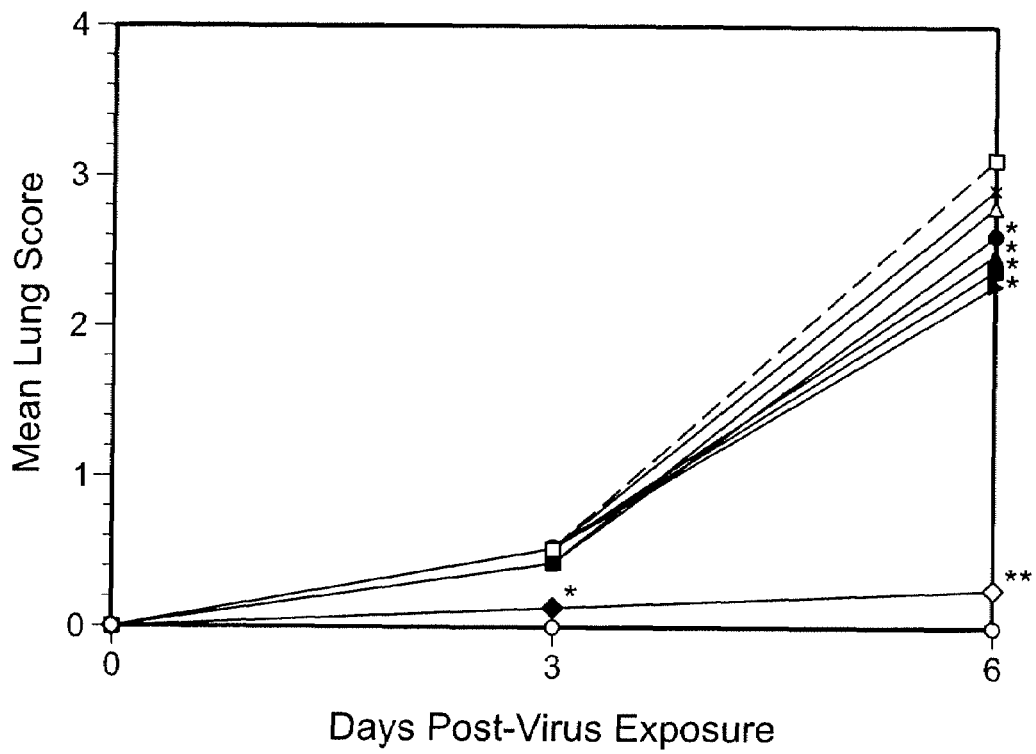
Figure 11:
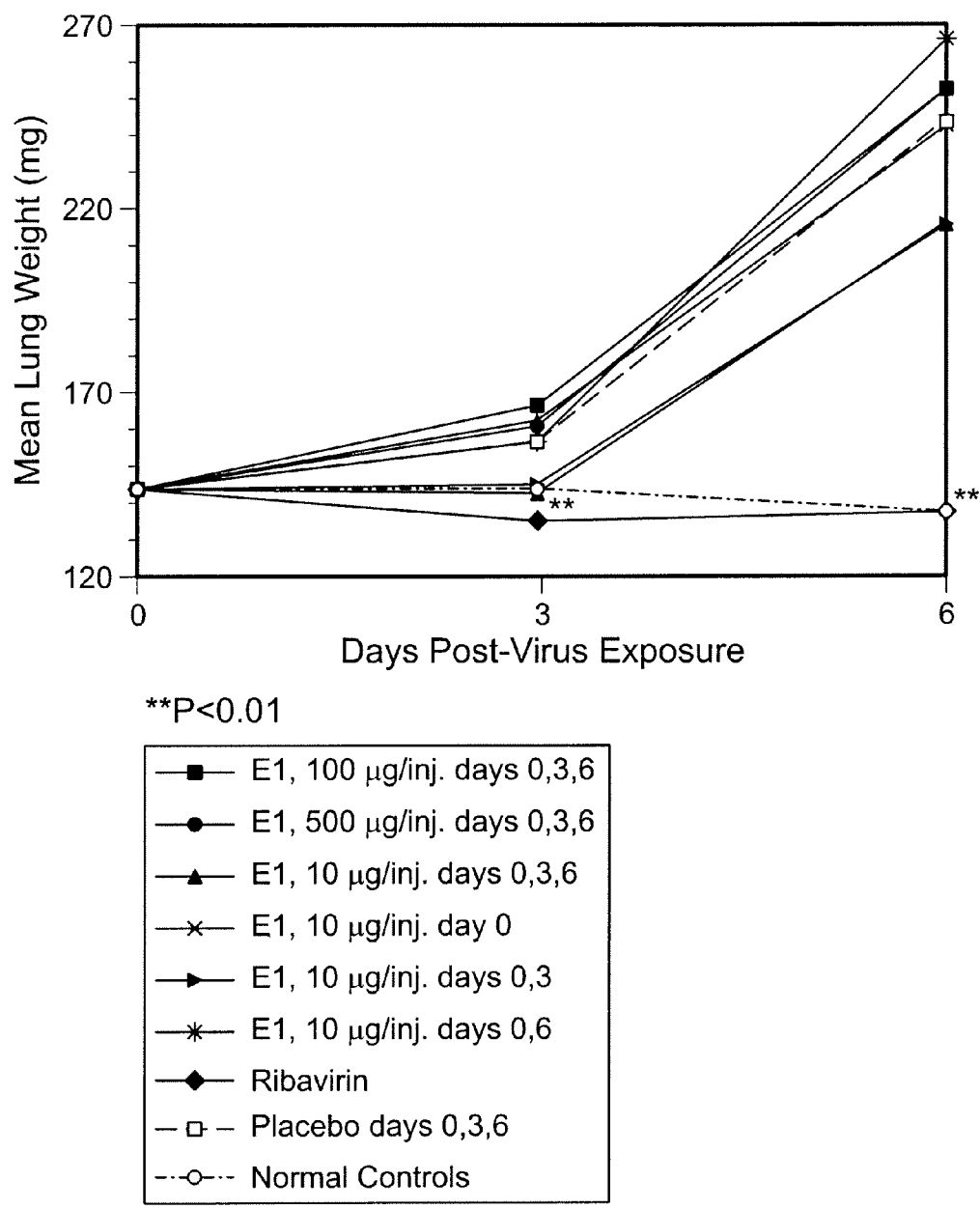
Figure 12:
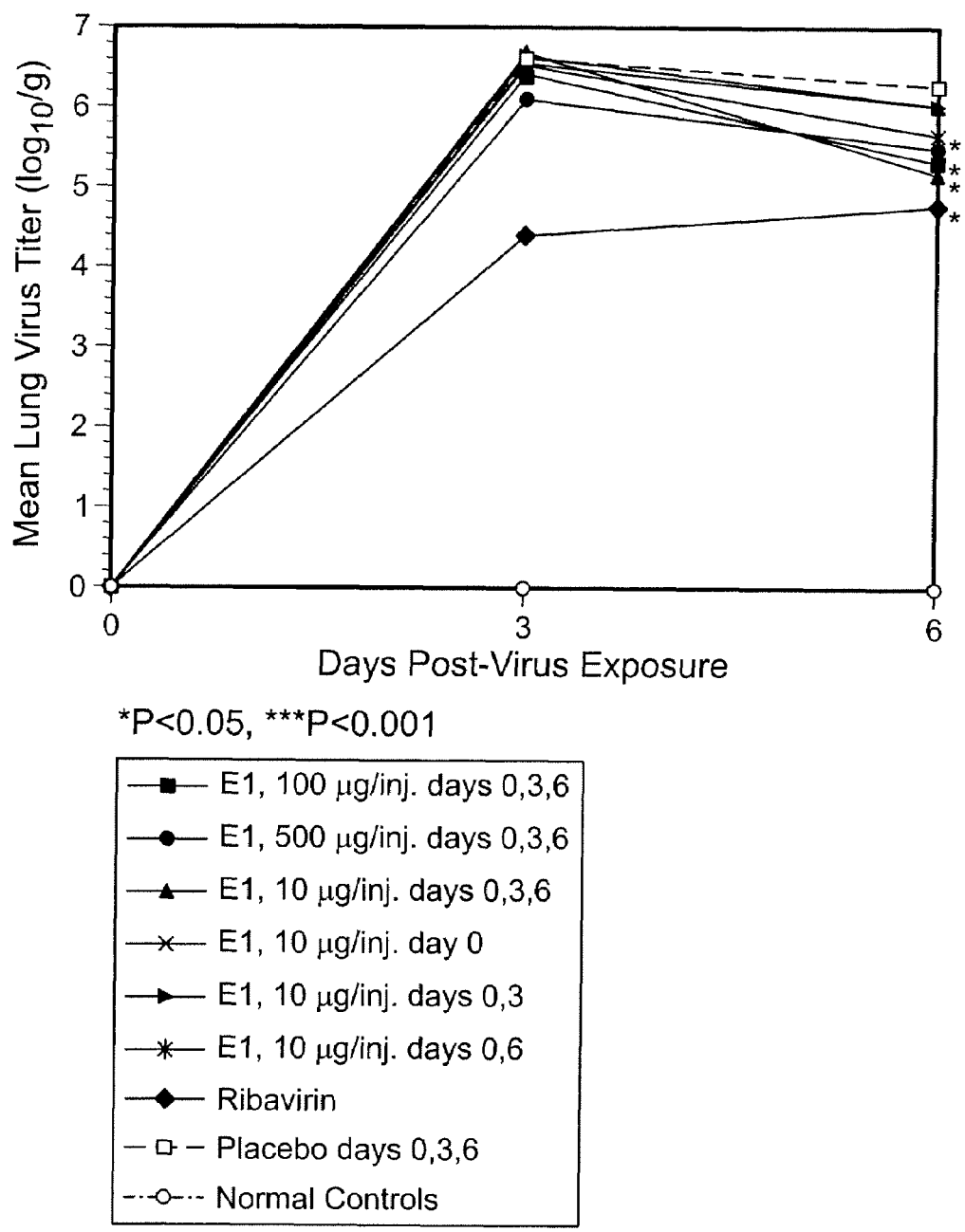

FIG. 18. Comparison of i.n., i.p., and combined i.n./i.p. treatments with E1 on lung scores in influenza (H1N1) virus-infected mice. Mean lung score is shown on the Y-axis. Days post-virus exposure is shown on the x-axis. Keys for lines representing normal controls, BSA/PBS, ribavirin, different concentrations of E1 administered intranasally, intraperitoneally or both intranasally and intraperitoneally are shown. * represents different P-values.

FIG. 19. Comparison of i.n., i.p., and combined i.n., i.p. treatments with E1 on lung weight in influenza (H1N1) virus-infected mice. Mean lung weight in miligrams is shown on the y-axis. Days post-virus exposure is shown on the x-axis. Keys for lines representing normal controls, BSA/PBS, different concentrations of E1 administered intranasally, intraperitoneally are both intranasally and intraperitoneally are shown. * and ** represent different P-values.

FIG. 20. Comparison of i.n., i.p., and combined i.n., i.p. treatments with E1 on lung virus titers in influenza (H1N1) virus-infected mice. Mean lung virus titer ($\log_{10}$/g) is shown on the y-axis. Days post-virus exposure is shown on the x-axis. Keys for lines representing normal controls, BSA/PBS, different concentrations of E1 administered intranasally, intraperitoneally are both intranasally and intraperitoneally are shown. * and ** represent different P-values.

FIG. 21. Mortality of Banzi virus-inoculated mice treated with Barrogen. Survival rate of mice is shown on the y-axis. Days post-virus exposure is shown on the x-axis. Keys for lines representing different concentrations of Barrogen, Ampligen® and placebo are shown. * and *** represent P-values.

FIG. 22. Percent weight change in Banzi inoculated animals treated with Barrogen. Percent weight change is shown on the y-axis. Days post virus inoculation is shown on the x-axis. Keys for lines representing different concentrations of Barrogen, Ampligen®, placebo and normals are shown. *,  and * represent P-values.

FIG. 23. Average viral titer in the brains of mice at 8 dpi. Average titer is shown on the y-axis. Different concentrations of Barrogen, Ampligen® and placebo are represented on the x-axis. Numbers in parentheses indicate number of animals where virus was detected versus number of animals assayed. * and ** represent P-values.

FIG. 24. Effect of Barrogen treatment on day 3 liver Punta Toro virus titers. Mean liver virus titer ($\log_{10}/CCID_{50}$/g) is shown on the y-axis. Different concentrations of Barrogen, ribavirin, normal controls and 0.1% BSA/PBS are represented on the x-axis. * represents P-value.

FIG. 25. Effect of Barrogen treatment on day 3 serum Punta Toro virus titers. Mean serum virus titer ($\log_{10}CCID_{50}$/g) is shown on the y-axis. Different concentrations of Barrogen, ribavirin, normal controls and 0.1% BSA/PBS are represented on the x-axis. * represents P-value.

FIG. 26. Effect of Barrogen treatment on day 3 serum ALT levels. Mean serum ALT (IU/mL) is shown on the y-axis. Different concentrations of Barrogen, ribavirin, normal controls and 0.1% BSA/PBS are represented on the x-axis. *** represents P-value.

FIG. 27. Effect of therapeutic Barrogen treatment on day 3 liver Punta Toro virus titers. Mean liver virus titer ($\log_{10}CCID_{50}$/g) is shown on the y-axis. Different concentrations of Barrogen, ribavirin, normal controls, 0.1% BSA/PBS and placebo are represented on the x-axis. * represents P-value.

FIG. 28. Effect of therapeutic Barrogen treatment on day 3 serum Punta Toro virus titers. Mean serum virus titer ($\log_{10}CCID_{50}$/mL) is shown on the y-axis. Different concentrations of Barrogen, ribavirin, normal controls and placebo are represented on the x-axis. * and *** represent P-value.

FIG. 29. Effect of therapeutic Barrogen treatment on day 3 serum ALT levels. Mean serum ALT (IU/mL) is shown on the y-axis. Different concentrations of Barrogen, ribavirin, normal controls and placebo are represented on the x-axis. *** represents P-value.

FIG. 30. Survival of mice infected with Banzi virus and treated −4 hpi and 2 dpi with Barrogen, Barrogen plus agonist cocktail, Ampligen®, or Placebo. ** represents P-value.

FIG. 31. Mean percentage weight change in mice infected with Banzi virus and treated −4 hpi and 2 dpi with Barrogen, Barrogen plus agonist cocktail, Ampligen®, or Placebo. ** represents P-value.

DETAILED DESCRIPTION OF THE INVENTION

The present invention provides methods for treating or preventing a disease, disorder or condition associated with a viral infection in a subject by administering to the subject a therapeutically or prophylactically effective amount of a pharmaceutical composition that provides ARP using a dosing and resting regimen. The present invention also relates to methods of treating or preventing a disease, disorder or condition associated with a viral infection by administering an amount of a pharmaceutical composition that provides ARP using a dosing and resting regimen to effectively cure at least 70% of subjects in a population of at least ten subjects. While not bound by any theory, the invention is based, in part, on the Applicants' discovery that recombinant Barrogen (rBBX-01) has anti-viral activities in vivo that exceed the antiviral activity expected for an immunostimulatory compound. This discovery with respect to Barrogen applies to ARPs (as defined and described below) in general.

One example of the advantages conferred by the present invention is the ability to effect cures of viral infections in infected subjects, thereby eliminating the disease, disorder, or condition caused by the viral infection. The cure rate achieved with the present invention is remarkably greater than expected just from knowledge of ARP's immunostimulatory activity.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease.

The term "cure" or "curing" as used herein refers to substantially eliminating symptoms of a disease, disorder or condition associated with a viral infection in accordance with the art recognized standard. The term "cured" as used herein refers to the state of being substantially free of symptoms associated with a disease, disorder or condition.

The term "dosing and resting regimen" refers to a systematic dose schedule of a therapeutic or prophylactic substance (e.g., a pharmaceutical composition that provides ARP) with a time period of no administration of the substance.

Within the meaning of the present invention the term "day of infection" refers to day of exposure to infection. An exposure to infection may be suspected by the subject of the invention, e.g., without any limitation, a subject may suspect exposure to a sexually transmitted viral infection after intimate sexual behavior with another.

Within the meaning of the present invention "onset of symptoms" refers to indications observed in or perceived by a subject with a disease, disorder or condition associated with a viral infection. Numerous indications associated with specific diseases, disorders or conditions are well know in the art (see, e.g., Fields et al., eds., *Fields Virology*, Third Edition, Lipincott-Raven Publishers, Philadelphia; Galasso et al., *Practical Diagnosis of Viral Infections,* Third Edition, 1993, Raven Press, New York; Specter et al., *Clinical Virology Manual,* Third Edition, 2000, ASM Press, Washington D.C.).

The term "subject" as used in this application means an animal with an immune system, such as aves and mammals. Mammals include canines, felines, rodents, bovines, equines, porcines, ovines, and primates. Aves include fowls, songbirds, raptors, etc. The invention is therefore useful for treating a disease, disorder or a condition associated with a viral infection in dogs, cats, mice, rats, rabbits, cows, horses, pigs, sheep, goats, apes, monkeys, chickens, turkeys, canaries, eagles, hawks, owls, and, particularly humans. Thus, the invention can be used in veterinary medicine, e.g., to treat companion animals, farm animals, laboratory animals in zoological parks, and animals in the wild. The invention is particularly desirable for human medicine applications.

Within the meaning of the present invention, the term "conjoint administration" is used to refer to administering the immunostimulatory agent and the pharmaceutical composition of the invention within a three day period.

The term "therapeutically effective" applied to dose or amount refers to that quantity of a compound or pharmaceutical composition or vaccine that is sufficient to result in a desired activity upon administration to a mammal in need thereof.

The phrase "pharmaceutically acceptable", as used in connection with compositions of the invention, refers to molecular entities and other ingredients of such compositions that are physiologically tolerable and do not typically produce unwanted reactions when administered to a subject, particularly a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical or vaccine compositions of the invention refers to a diluent, excipient, or vehicle with which a compound (e.g., an antigen and/or a MHC molecule) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

ARPs

An ARP of the present invention is a protein that has immune stimulatory activity, and is structurally related to an immunostimulatory protein of an Apicomplexan organism. An Apicomplexan organism is one of those of the phylum Apicomplexa. In specific embodiments, an ARP of the invention includes, but is not limited to, SEQ ID NO:1 (ARP of *E. tenella*), SEQ ID NO:2 (ARP of *E. acervulina*), and a protein that comprises SEQ ID NOs:3-7 (partial amino acid sequence of bovine *Eimeria* spp. ARP). SEQ ID NOs: 3-7 are not necessarily contiguous, as there may be intervening or adjacent sequences to each fragment. In a specific embodiment, such an ARP protein comprises SEQ ID NOs:3, 4, 5, 6 and 7 in an order of SEQ ID NO:3 to SEQ ID NO:7 from the N terminus to the C terminus.

Preparation and purification of ARPs, purification of soluble ARPs from tissue and cell extracts, purification of membrane-linked ARPs, antibody-affinity purification of ARPs, recombinant expression of ARP, isolation of ARP gene, peptide synthesis of ARP, ARPs of purified Apicomplexa, derivatives and analogs of ARPs, antibodies to ARPs, derivatives and analogs, structure prediction and functional analysis of ARPs and characterization and demonstration of ARP activity are described in PCT/US2004/023231 (published as WO 2005/010163) and PCT/US2004/023113 (published as WO 2005/010040).

The term "ARP" thus encompasses (a) an isolated protein comprising SEQ ID NO:1, (b) an isolated protein comprising SEQ ID NO:2, (c) an isolated protein comprising SEQ ID NO:19, (d) an isolated protein comprising SEQ ID NO:20, (e) an isolated protein comprising SEQ ID NOS: 3, 4, 5, 6 and 7, (f) an isolated protein comprising a variant of SEQ ID NO:1, SEQ ID NO:2, SEQ ID NO:19 or SEQ ID NO:20, wherein said variant has only conservative amino acid substitutions relative to SEQ ID NO:1, SEQ ID NO:2, SEQ ID NO:19 or SEQ ID NO:20, respectively, (g) an isolated protein comprising a variant of SEQ ID NO: 3, 4, 6 or 7, wherein said variant has only conservative amino acid substitutions relative to SEQ ID NO: 3, 4, 6 or 7, respectively, (h) an isolated protein that has at least 25% sequence identity to the sequence of SEQ ID NO:1, SEQ ID NO:2, SEQ ID NO:19 or SEQ ID NO:20 as determined by a BLAST 2.0 algorithm set to default parameters, (i) an isolated protein comprising a PROF (profilin) domain, (j) an isolated Apicomplexan protein comprising an amino acid sequence encoded by a nucleic acid consisting of a nucleotide sequence hybridizable to SEQ ID NO: 12, 13, 14, 15, 16, 17, or 18 or a complement of any of the foregoing SEQ ID NOs, under conditions of low stringency, (k) an isolated Apicomplexan protein comprising an amino acid sequence encoded by a nucleic acid consisting of a nucleotide sequence hybridizable to SEQ ID NO: 12, 13, 14, 15, 16, 17, or 18 or a complement of any of the foregoing SEQ ID NOs, under conditions of high stringency, and (l) an isolated protein that is a product of a process comprising the steps described in PCT/US2004/023231 (published as WO 2005/010163) and PCT/US2004/023113 (published as WO 2005/010040). An ARP of the invention may be provided by an isolated nucleic acid comprising a nucleotide sequence encoding any of (a) to (e) above, or a cell transformed with a nucleic acid comprising a nucleotide sequence encoding any of (a) to (e) above, with the nucleotide sequence being operably linked to a promoter.

In another embodiment, the ARP contains a disulfide bond that is reduced, i.e., subjected to reducing conditions that would disrupt a disulfide bond. In a specific embodiment, ARP protein, e.g., Barrogen, that has been reduced has activity that is 2-5 times greater than the oxidized form.

In some embodiments, an ARP of the invention is post-translationally modified. In other embodiments, an ARP of the invention is not post-translationally modified. In specific embodiments, an ARP of the invention is glycosylated. In other embodiments, an ARP of the invention is unglycosylated.

In some embodiments, an ARP of the invention is membrane-linked. In other embodiments, an ARP of the invention is not membrane-linked. A non-membrane-linked ARP can exist in soluble form. In a specific embodiment, an ARP of the invention is glysosylphosphatidylinositol (GPI)-linked. In specific embodiments, an ARP of the invention is not GPI-linked. In one embodiment, an ARP of the invention is a lipoprotein. In another embodiment, an ARP of the invention is not a lipoprotein.

In a specific embodiment, an ARP of the invention is a native protein. In a specific embodiment, an ARP of the invention is a recombinantly produced protein. In specific embodiments, an ARP of the invention has a molecular weight in the range of 18 kD to 25 kD, and an isoelectric point (pI) between 4.0 and 4.7.

In a specific embodiment, an ARP of the invention is a naturally occurring Apicomplexan protein. In some embodiments, the ARPs of the invention exist in a soluble form. In some embodiments, the ARPs of the invention exist in a membrane-linked form.

In a specific embodiment, an ARP of the invention is an isolated protein that has at least 25% sequence identity to the sequence of SEQ ID NO:1, SEQ ID NO:2, SEQ ID NO:19 or SEQ ID NO:20 as determined by a BLAST 2.0 algorithm set to default parameters.

In another embodiment, an ARP of the invention is an isolated protein comprising SEQ ID NO:1.

In another embodiment, an ARP of the invention is an isolated protein comprising SEQ ID NO:2.

In another embodiment, an ARP of the invention is an isolated protein comprising SEQ ID NO: 19.

In another embodiment, an ARP of the invention is an isolated protein comprising SEQ ID NO:20. The term "Barrogen" has been coined with respect to an ARP having the sequence of SEQ ID NO:20; it is also called rBBX-01. This specific form of ARP may be a protein that is a product of a process comprising steps described in PCT/US2004/023231 (published as WO 2005/010163) and PCT/US2004/023113 (published as WO 2005/010040).

In a specific embodiment, an ARP of the invention is an Apicomplexan protein (encoded by a genome of an Apicomplexan organism) that has at least 25%, at least 30%, at least 35%, at least 40%, at least 45%, at least 50%, at least 55%, at least 60%, at least 65%, at least 70%, at least 75%, at least 80%, at least 85%, at least 90% identity, at least 95% identity, at least 96% identity, at least 97% identity, at least 98% identity, or at least 99% identity to the sequence of SEQ ID NO:1, SEQ ID NO:2, SEQ ID NO:19, or SEQ ID NO:20, as measured by a BLAST algorithm with default parameters using the BLAST 2.0 suite of programs (Altschul et al., *Nucleic Acids Res.* 1977; 2:3389-3402), wherein the ARP protein has anti-viral activity. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Ausubel, et al., Eds., *Current Protocols in Molecular Biology,* Chapter 19, 1995, Greene Publishing and Wiley-Interscience, New York. New versions of the above programs or new programs altogether will undoubtedly become available in the future, and can be used with the present invention. It is to be understood that default settings of the parameters can be readily changed as needed in the future.

In a specific embodiment, an ARP of the invention is a protein that contains a conserved PROF (profilin) domain, wherein the protein has anti-viral activity. Conserved domains are defined based on recurring sequence patterns or motifs. The search for a known conserved domain can be done, e.g., at the website ncbi.nlm.nih.gov/Structure/cdd/wrpsb.cgi. In one embodiment, the conserved PROF (profilin) domain is determined by using Conserved Domain Database (CDD v. 1.60) and a RPS-BLAST (Reverse Position-Specific BLAST) algorithm set to default parameters. Current CDD database contains domains derived from two popular collections, Smart and Pfam, plus contributions from National Center for Biotechnology Information (hereinafter "NCBI"). In Conserved Domain Database, the PROF (profilin) domain is also identified as smart 00392 or cd 00148 domain, or pfam 00235 domain (PSSM Id's 14983, 14824 and 801 correspondingly). To identify conserved domains in a protein sequence, the RPS-BLAST algorithm can be used. The query sequence is compared to a position-specific score matrix prepared from the underlying conserved domain alignment. Hits may be displayed as a pairwise alignment of the query sequence with a representative domain sequence, or as a multiple alignment. See, Marchler-Bauer et al., *Nucleic Acids Research* 2003; 31:383-387; Marchler-Bauer et al., *Nucleic Acids Research* 2002; 30:281-283. The "PROF" domain is represented by profilin, which is ubiquitous in nature, occurring in organisms from amoeba to mammals. Profilin is involved in the regulation of actin polymerization and may link the cytoskeleton with major signaling pathways by interacting with components of the phosphatidylinositol cycle and Ras pathway. See e.g., Korenbaum et al., *Biochemistry* 1998; 37(26):9274-83; Schluter et al., *Biochim Biophys Acta.* 1997; 1359(2):97-109. In a specific embodiment, an ARP of the invention contains the profiling domain of a plant profilin, e.g., SEQ ID NO: 8, 9, 10 or 11.

In a specific embodiment, an ARP of the invention is an Apicomplexan protein whose encoding nucleic acid (Apicomplexan cDNA or genomic nucleic acid) hybridizes under stringent conditions (high, moderate or low stringent condition) to an ARP nucleic acid (e.g., having a sequence as set forth in SEQ ID NO:12, SEQ ID NO:13, SEQ ID NO:14, SEQ ID NO:15, SEQ ID NO:16, SEQ ID NO:17, or SEQ ID NO:18 or to its reverse complement, or to a nucleic acid encoding an ARP derivative, or to its reverse complement), wherein the Apicomplexan protein has anti-viral activity. Stringent conditions are sequence-dependent and circumstance-dependent, for example, longer sequences hybridize specifically at higher temperatures. An extensive guide to the hybridization of nucleic acids is found in Tijssen, *Techniques in Biochemistry and Molecular Biology-Hybridization with Nucleic Probes,* "Overview of principles of hybridization and the strategy of nucleic acid assays", 1993. See also Martin et al., *EMBO J* 1985; J 4:1625-1630; Davies et al., *Methods in Molecular Biology* Vol 28: Protocols for nucleic acid analysis by non-radioactive probes; Isaac, P. G. (ed) pp 9-15, Subjecta Press Inc., Totowa N.J., USA.

In a specific embodiment, a nucleic acid that is hybridizable to an ARP nucleic acid or its reverse complement under conditions of low stringency is provided. By way of example but not limitation, procedures using such conditions of low stringency are as follows (see also Shilo and Weinberg, *Proc. Natl. Acad. Sci. U.S.A.* 1981; 78, 6789-6792): filters containing DNA are pretreated for 6 hours at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20× 106 cpm $^{32}$P-labeled probe is used; filters are incubated in hybridization mixture for 18-20 hours at 40° C. and then washed for 1.5 hours at 55° C. in a solution containing 2×SSC, 25 mM Tris-HCl (pH7.4), 5 mM EDTA, and 0.1% SDS; the wash solution is replaced with fresh solution and incubated an additional 1.5 hours at 60° C.; filters are blotted dry and exposed for autoradiography. If necessary, filters are washed for a third time at 65-68° C. and re-exposed to film. In another example, low stringency hybridization is carried out at 62° C. without formamide. Other conditions of low stringency which may be used are well known in the art (e.g., as employed for cross-species hybridizations).

In another specific embodiment, a nucleic acid that is hybridizable to an ARP nucleic acid, or its reverse complement, under conditions of high stringency is provided. By way of example but not limitation, procedures using such conditions of high stringency are as follows: prehybridization of filters containing DNA is carried out for 8 hours to overnight at 65° C. in buffer composed of 6×SSC, 50 mM Tris-HCl (pH7.5), 1 mM EDTA, 0.02% PVP, 0.02% Ficoll, 0.02% BSA, and 500 µg/ml denatured salmon sperm DNA; filters are hybridized for 48 h at 65° C. in prehybridization mixture containing 100 µg/ml denatured salmon sperm DNA and 5-20×10$^6$ cpm of $^{32}$P-labeled probe; washing of filters is done at 37° C. for 1 hour in a solution containing 2×SSC, 0.01% PVP, 0.01% Ficoll, and 0.01% BSA; this is followed by a wash in 0.1×SSC at 50° C. for 45 min before autoradiography. In another example, high stringency hybridization is carried out at 62° C. with 50% formamide. Other conditions of high stringency which may be used are well known in the art.

In another specific embodiment, a nucleic acid that is hybridizable to an ARP nucleic acid, or its reverse complement, under conditions of moderate stringency is provided. Selection of appropriate conditions for such stringencies is well known in the art (see e.g., Sambrook et al., 1989, *Molecular Cloning, A Laboratory Manual*, 2d Ed., Cold Spring Harbor Laboratory Press, Cold Spring Harbor, N.Y.; see also, Ausubel et al., eds., in the *Current Protocols in Molecular Biology* series of laboratory technique manuals, ©1987-1997, Current Protocols, ©1994-1997 John Wiley and Sons, Inc.). In one non-limiting example, moderate stringency hybridization can be carried out at 62° C. with 20% formamide.

Therapeutic ARPs of the invention can be tested in vitro for the desired activity by any one or more assays known in the art.

An ARP of the invention has anti-viral activity. In specific embodiments, a therapeutic or prophylactic composition of the invention for the prevention and treatment of a disease, disorder or condition associated with a viral infection comprises an enriched ARP.

As used herein, the term "enriched" in reference to a protein (e.g., a peptide, polypeptide or fusion protein) means that the protein constitutes a higher fraction of the total amount of protein present in the composition of interest, relative to the natural or original state from which the protein is derived. The enrichment can be achieved by preferential reduction in the amount of other protein present, or by a preferential increase in the amount of the specific protein of interest, or by a combination of the two. It should be noted that "enriched" does not imply that there are no other proteins present. The term also does not imply that there are no proteins present from other sources. The other source proteins may, for example, comprise protein(s) encoded by a genome of another species, or of a cloning vector. The term is meant to cover only those situations in which man has intervened to elevate the proportion of the desired protein. In specific embodiments, an ARP is greater than 0.001%, greater than 0.003%, greater than 0.01%, greater than 0.05%, greater than 0.1%, greater than 0.5%, greater than 1%, greater than 10%, greater than 20%, greater than 30% of total protein by weight.

The term "enriched" in reference to a molecule, such as a protein (ARP protein) or nucleic acid, means that the molecule constitutes a higher fraction of the total amount of molecules present in the composition of interest, relative to the natural or original state from which the molecule is derived. The enrichment can be achieved by preferential reduction in the amount of other molecules present, or by a preferential increase in the amount of the specific molecule of interest, or by a combination of the two. It should be noted that "enriched" does not imply that there are no other molecules present. The term also does not imply that there are no molecules present from other sources. The other source nucleic acids may, for example, comprise nucleic acid(s) encoded by a genome of another species, or of a cloning vector. The term is meant to cover only those situations in which man has intervened to elevate the proportion of the desired molecule.

In a preferred embodiment, an ARP of the invention is purified. The term "purified" in reference to a protein or a nucleic acid preferably means at least one order of magnitude of purification is achieved, more preferably two or three orders of magnitude, most preferably four or five orders of magnitude of purification of the starting material or of the natural material. Thus, the term "purified" as used herein does not mean that the material is 100% purified and thus does not mean that a purified protein or a nucleic acid excludes any other material. In specific embodiments, a purified ARP is at least 60%, at least 80%, or at least 90% of total protein or nucleic acid, as the case may be, by weight. In a specific embodiment, a purified ARP is purified to homogeneity as assayed by, e.g., sodium dodecyl sulfate polyacrylamide gel electrophoresis, or agarose gel electrophoresis.

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

In a specific embodiment, an ARP of the invention is present in the form of purified viable or inactivated Apicomplexan organisms at any developmental stage or a protein fraction thereof (e.g., a protein-containing membrane preparation thereof, or a storage granule preparation thereof). In a specific embodiment, an Apicomplexan organism is an Eimeria, which is species-specific and usually cannot cause symptomatic infection in a host of a different species from its native host. In another specific embodiment, an inactivated Apicomplexan organism is a life cycle defective Apicomplexan organism.

METHODS OF THE INVENTION

In one aspect, the present invention provides a method for treating or preventing a disease or condition associated with a viral infection in a subject by administering to the subject a therapeutically or prophylactically effective amount of a pharmaceutical composition that provides ARP, wherein the therapeutically or prophylactically effective amount of the pharmaceutical composition that provides ARP is in the range of from 0.0001 to 100 μg per kg body weight of the subject; and the therapeutically or prophylactically effective amount of the pharmaceutical composition that provides ARP is administered using a dosing and resting regimen starting on day of infection or onset of a symptom associated with the viral infection.

Another aspect of the present invention is to provide a method for treating or preventing a disease, disorder or condition associated with a viral infection by administering an amount of a pharmaceutical composition that provides ARP using a dosing and resting regimen to effectively cure at least 70% of subjects in a population of at least ten subjects.

Cure rates of the present invention include, but are not limited to, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% of subjects having a disease, disorder or condition associated with a viral disease in a population of at least 100 subjects.

ARP has been shown to be a very potent stimulator of IL-12 release from dendritic cells, up regulates inflammatory modulators in vivo (IL-12, MCP-1, IL-6, TNF-α and IFN-γ) and has anti tumor properties in mice. In addition, it is synergistic in vitro with anti-CD40 antibody, IFN-γ, IL-4 and GM-CSF; is active across species barriers in vivo; and has no observable toxicity. Based on these activities, it has been speculated to be an inducer of protozoan-targeted innate immunity, which may explain its potential benefit to the intestinal tract and potency as an agent in cancer immunotherapy (Rosenberg et al., *Int. J. Cancer* 2005; 114: 756-765). The immune activation property of ARP is utilized in this invention to treat/prevent or cure diseases, disorders or conditions associated with viral infections.

Diseases, disorders or conditions of the present invention include, but are not limited to those associated with viral infections of Hepatitis type A virus, Hepatitis type B virus, Hepatitis type C virus, Influenza virus, Varicella virus, Adenovirus, Herpes simplex type I virus (SHV-1), Herpes simplex type II virus (SHV-II), Rinderpest virus, Rhinovirus, Echovirus, Rotavirus, Respiratory syncytial virus, Papilloma virus, Papova virus, Cytomegalovirus, Echinovirus, Arbovirus, Huntavirus, Coxsackie virus, Mumps virus, Measles virus, Rubella virus and Polio virus.

In one embodiment, the viruses of the present invention include, but are not limited to, RNA viruses (e.g., viruses which belong in the Arenaviridae, Astroviridae, Bimaviridae, Bunyaviridae, Calicoviridae, Coronaviridae, Filoviridae, Flaviviridae, Orthomyxoviridae, Paramyxoviridae, Picomaviridae, Reoviridae, Retroviridae, Rhabdoviridae and Togaviridae families).

In another embodiment, the viruses of the present invention include, but are not limited to, negative strand segmented RNA viruses (e.g., viruses which belong in the Arenaviridae, Bunyaviridae and Orthomyxoviridae families).

The genuses of viruses in the Bunyaviridae family include, but are not limited to, Orthobunyavirus, Hantavirus, Nairovirus, Phlebovirus and Tospovirus. In particular embodiments, the viruses of the present invention include, but are not limited to, Punta Toro virus, Rift Valley Fever virus and Sandfly Fever virus in the Phlebovirus genus.

The genuses of the viruses in the Orthomyxoviridae family include, but are not limited to, Influenzavirus A, Influenzavirus B, Influenzavirus C, Thogotovirus and Isavirus, In one embodiment, the virus of the present invention includes, but is not limited to, Influenza A virus in the Influenzavirus A genus.

In a particular embodiment, a disease, disorder or condition associated with a virus in the Orthomyxoviridae family treatable/preventable or curable by the present invention excludes Influenza A virus.

In another embodiment, the viruses of the present invention include, but are not limited to, positive strand RNA viruses (e.g., viruses which belong in the Flaviviridae, Picornaviridae, Coronaviridae and Togaviridae families). The genuses of viruses in the Flaviviridae family include, but are not limited to, Flavivirus, Pestivirus and Hapecivirus. In specific embodiments, the viruses of the present invention include, but are not limited to, Banzi virus, Yellow fever virus, Dengue virus and West Nile virus in the Flavivirus genus.

In another specific embodiment, the present invention discloses a method of treating/preventing or curing a subject (e.g., a human) having a disease, disorder or condition associated with a Influenza A/NWS/33 virus infection. See Examples 1-5. For example, as disclosed in Example 5, BALB/C mice infected with Influenza A virus are treated by administering to the mice i.p. with Barrogen in dosages of 10, 1, or 0.1 μg/injection on days 0 (4 h post—virus exposure), 3 and 6. Treatment was evaluated by the marked lessening of $SaO_2$ decline, survival of virally infected animals, maintained lung weight and lung scores as compared to positive control mice treated with ribavirin and sham infected mice.

In yet another embodiment, the present invention discloses a method of treating/preventing or curing a subject having a disease, disorder or condition associated with Punta Toro virus infection. See Example 6. For example, as disclosed in Example 6, female C57B1/6 mice infected with Punta Toro virus are treated by administering to the mice i.p. with a single dose of Barrogen. Treatment was evaluated by the marked lessening of $SaO_2$ decline, survival of infected mice (100% of infected mice were cured), maintained hepatic icterus score, liver virus titer determination and alanine aminotransferase determination as compared to positive control mice treated with ribavirin and sham infected mice.

In another embodiment, the present invention discloses a method of treating/preventing or curing a subject (e.g., a human) having a disease, disorder or condition associated with Banzi virus infection. As disclosed in Example 7, female BALB/C mice infected with Banzi virus are treated by administering to the mice i.p. with two doses of 10, 1, or 0.1 Ig/mouse of Barrogen. Treatment was evaluated by the survival of infected mice, percent weight change in Banzi virus infected mice and viral titer in the brains of Banzi virus infected mice as compared to positive control mice treated with Ampligen® and sham infected mice.

In another embodiment, the present invention discloses a method of treating/preventing or curing a subject (e.g., human) having a disease, disorder or condition associated with Influenza virus infection by administering to the subject a combination of Barrogen and Oseltamivir.

In another specific embodiment, the invention discloses a method for treating or preventing a disease, disorder or condition associated with a viral infection in a subject comprising administering to the subject a therapeutically or prophylactically effective amount of Barrogen wherein the Barrogen is administered conjointly with a therapeutically or prophylactically effective amount of an immunostimulatory agent. In a specific embodiment, the immunostimulatory agent is a cytokine; the examples show the benefit of combining an ARP, Barrogen, with the cytokine GM-CSF. See Example 4, infra.

The immunostimulatory agents of the present invention include, but are not limited to, GM-CSF, G-CSF, anti-CD40, IFN-γ, FLT-3 ligand, IFNα/β, TNF-α/β, MCP-1, IL-1, IL-2, IL-4, IL-6, IL-1 8, and other Th1-type immune activating agents.

Gene Therapy

In one embodiment, ARP is administered to a subject to prevent or treat or cure a disease, disorder or condition associated with an infectious disease by way of gene therapy. Gene therapy refers to therapy performed by the administration to a subject of an expressed or expressible nucleic acid.

Any of the methods for gene therapy available in the art can be used according to the present invention. Exemplary methods are described below.

For general reviews of the methods of gene therapy, see Goldspiel et al., *Clinical Pharmacy* 1993; 12:488-505; Wu and Wu, *Biotherapy* 1991; 3:87-95; Tolstoshev, *Ann. Rev. Pharmacol. Toxicol.* 1993; 32:573-596; Mulligan, *Science,* 1993; 260:926-932; and Morgan and Anderson, *Ann. Rev. Biochem.* 1993; 62:191-217; May, 1993, TIBTECH 11 (5): 155-215. Methods commonly known in the art of recombinant DNA technology which can be used are described in Ausubel et al. (eds.), *Current Protocols in Molecular Biology,* 1993, John Wiley & Sons, N.Y.; and Kriegler, *Gene Transfer and Expression,* 1990, A Laboratory Manual, Stockton Press, NY.

In a gene therapy embodiment, the pharmaceutical composition of the invention comprises nucleotide sequences encoding one or more ARPs, said nucleic acid sequences being part of expression vectors that express ARPs in a suitable host. In particular, such nucleic acids have promoters, preferably heterologous (non-native) promoters, operably linked to the ARP coding region, said promoter being inducible or constitutive, and, optionally, tissue-specific. In another particular embodiment, nucleic acid molecules are used in which the ARP coding sequences and any other desired sequences are flanked by regions that promote homologous recombination at a desired site in the genome, thus providing for intrachromosomal expression of the ARP nucleic acids (Koller and Smithies, *Proc. Natl. Acad. Sci. USA* 1989; 86:8932-8935; Zijlstra et al., *Nature* 1989; 342:435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* 1987; 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g, PCT Publications WO 92/06180, WO 92/22635, WO92/20316, WO93/14188, WO 93/20221. Alternatively, the nucleic acid can be introduced intracellularly and incorporated within host cell DNA for expression, by homologous recombination (Koller and Smithies, *Proc. Natl. Acad. Sci. USA* 1989; 86:8932-8935; Zijlstra et al., *Nature* 1989; 342:435-438).

In one embodiment, viral vectors that contain nucleic acids encoding one or more ARPs are used in accordance with the invention (see Miller et al., *Meth. Enzymol.* 1993; 217:581-599). A retroviral vector, for example, can be used in gene therapy to deliver a pharmaceutical composition that provides ARP to a subject. These retroviral vectors have been modified to delete retroviral sequences that are not necessary for packaging of the viral genome and integration into host cell DNA. More detail about retroviral vectors can be found in Boesen et al., *Biotherapy* 1994; 6:291-302; Clowes et al., *J. Clin. Invest.* 1994; 93:644-651; Kiem et al., *Blood* 1994; 83:1467-1473; Salmons and Gunzberg, *Subject Gene Therapy* 1993; 4:129-141; and Grossman and Wilson, *Curr. Opin. in Genetics and Devel.* 1993; 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 1993; 3:499-503) present a review of adenovirus-based gene therapy. Bout et al., *Subject Gene Therapy* 1994; 5:3-10) demonstrated the use of adenovirus vectors to transfer genes to the respiratory epithelia of rhesus monkeys. Other instances of the use of adenoviruses in gene therapy can be found in Rosenfeld et al., *Science* 1991; 252:431-434; Rosenfeld et al., *Cell* 1992; 68:143-155; Mastrangeli et al., *J. Clin. Invest.* 1993; 91:225-234; PCT Publication WO94/12649; and Wang et al., *Gene*

*Therapy* 1995; 2:775-783. For example, adenovirus vectors can be used in gene therapy to deliver ARPs to a subject to prevent or treat a disease, disorder or condition associated with a viral infection. Adeno-associated virus (AAV) has also been proposed for use in gene therapy (Walsh et al., *Proc. Soc. Exp. Biol. Med.* 1993; 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 1993; 217:599-618; Cohen et al., *Meth. Enzymol.* 1993; 217: 618-644; Cline, *Pharmac. Ther.* 1985; 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes; blood cells such as T lymphocytes, B lymphocytes, NK cells, dendritic cells, monocytes, macrophages, neutrophils, eosinophils, megakaryocytes, granulocytes, autologous cancer cells, various stem or progenitor cells, in particular hematopoietic stem or progenitor cells, e.g, as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, the pharmaceutical composition of the invention is introduced into the cells such that the nucleotide sequences are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, Stemple and Anderson, *Cell* 1992; 71:973-985; Rheinwald, Meth. *Cell Bio.* 1980; 21A:229; and Pittelkow and Scott, *Mayo Clinic Proc.* 1986; 61:771). In another specific embodiment, transformed cells are used.

In a specific embodiment, the nucleic acid to be introduced for purposes of gene therapy comprises a constitutive, tissue-specific, or inducible promoter operably linked to the coding region. In one embodiment, the nucleic acid to be introduced for purposes of gene therapy comprises an inducible promoter operably linked to the coding region, such that expression of the nucleic acid is controllable by controlling the presence or absence of the appropriate inducer of transcription.

Other Anti-Infection Agents

The present invention provides methods of preventing/treating or curing a disease, disorder or condition associated with a viral infection in a subject, by administering to the subject a pharmaceutical composition that provides ARP alone or in combination with one or more prophylactic or therapeutic agents other than the pharmaceutical composition that provides ARP. Any agent or therapy which is known to be useful, or which has been used or is currently being used for the prevention or treatment of diseases, disorders or conditions associated with viral infections can be used in combination with a pharmaceutical composition that provides ARP in accordance with the invention described herein.

Examples of antiviral agents that can be used in combination with a pharmaceutical composition that provides ARP to treat/prevent or cure a disease, disorder or condition associated with a viral infection include, but are not limited to, idoxuridine, vidarabine, trifluridine, acyclovir, famciclovir, penciclovir, valacyclovir, ganciclovir, foscarnet, ribavirin, amantadine, rimantadine, cidofovir, oseltamivir, zanamivir, didanosine (ddI), stavudine (d4T), zalcitabine (ddC), zidovudine (AZT), lamivudine, abacavir, delavirdine, neviapine, efavirenz, saquinavir, ritonavir, indinavir, nelfinavir, amprenavir, lopinavir, and interferon.

Dosage Regimens

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The amount of the composition of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances.

The dosage of a pharmaceutical composition that provides ARP for administration in a human patient provided by the present invention is preferably less than 100 µg/kg body weight, less than 50 µg/kg body weight; less than 10 µg/kg body weight, less than 5 µg/kg body weight, less than 1 µg/kg body weight, less than 0.5 µg/kg body weight, less than 0.1 µg/kg body weight, less than 0.05 µg/kg body weight, less than 0.01 µg/kg body weight, or less than 0.001 µg/kg body weight. In a specific embodiment, the pharmaceutical composition that provides ARP is given at a dosage of 1 µg per person per day (or about 0.14 ng per kg body weight).

In one embodiment, a dose administered by a subcutaneous injection is ten times higher than a dose administered interperitoneally to the subject.

Prior to administering the first full dose, each patient preferably receives a subcutaneous injection of a small amount (e.g., 1/100 to 1/10 of the prescribed dose) of a composition of the invention to detect any acute intolerance. The injection site is examined one and two hours after the test. If no reaction is detected, then the full dose is administered. ARPs can also be administered orally. In one embodiment, intact sporulated oocysts of an Apicomplexan genus (e.g., *Eimeria tenella*) are given orally with drinking water. The dosage can be, by way of example, 100 to 10,000 oocysts in a single administration depending on the cross-species infectivity of the protozoan.

Dosage Schedule

The dose schedule of the pharmaceutical composition that provides ARP of the present invention for the treatment, prevention or cure of a disease, disorder or condition associated with a viral infection may depend on the nature of the infection. Chronic viral infections (e.g., HIV, Herpes) may have a different treatment schedule than acute viral infections (e.g., Influenza A, Punta Toro virus).

Frequent repetition of treatment with a pharmaceutical composition that provides ARP (e.g., Barrogen) may overstimulate the host immune state, leading to a hypo responsiveness that may adversely affect the progress of the disease. A dosing and resting regimen may be used to overcome the hypo responsiveness of the host immune response.

In one embodiment, the pharmaceutical composition that provides ARP is administered to the subject at least once within a week of the day of infection or the onset of a symptom associated with the infection.

In another embodiment, the dosing and resting regimen is once weekly for at least a month starting on the day of infection or the onset of a symptom associated with a chronic viral infection.

In another embodiment, the dosing and resting regimen comprises a first dose administered to the subject daily for a week starting on the day of infection or the onset of a symptom associated with a chronic viral infection and a second dose administered to the subject daily for a week at least once every other week after administration of the first dose.

In yet another embodiment, the dosing and resting regimen comprises a first dose administered to the subject on the day of infection or the onset of a symptom associated with an acute viral infection and a second dose administered to the subject at least once every 3 days after administration of the first dose. In one embodiment, the second dose is administered at least once every other day after administration of the first dose. In another embodiment, the second dose is administered at least once every four days after administration of the first dose. In yet another embodiment, the second dose is administered at least once every six days after administration of the first dose.

In a specific embodiment, a first dose of 5 µg per kg body weight of a pharmaceutical composition that provides ARP (e.g., Barrogen) is administered to a subject on the day of infection or the onset of a symptom associated with an acute infection and a second dose of 5 µg per kg body weight of a pharmaceutical composition that provides ARP (e.g., Barrogen) is administered at least once every three days after administration of the first dose.

Administrations, Formulations and Kits

Various delivery systems are known and can be used to administer a pharmaceutical composition that provides ARP, e.g., encapsulation in liposomes, microparticles, microcapsules, expression by recombinant cells, receptor-mediated endocytosis (see, e.g., Wu and Wu, *J. Biol. Chem.* 1987, 262:4429-4432), construction of an ARP nucleic acid as part of a retroviral or other vector, etc. Methods of introduction include, but are not limited to, intradermal, intramuscular, intraperitoneal, intravenous, subcutaneous, intranasal, rectal/anal and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved by, for example, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, a chimeric construction of the pharmaceutical composition of the present invention is used to target a specific area, i.e., even systemic administration of the composition would direct the composition to the organ of choice.

In a specific embodiment, the pharmaceutical composition of the present invention can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 1991; 88:1864-1868), etc. Alternatively, the pharmaceutical composition of the present invention can be introduced intracellularly and incorporated within host cell DNA for expression, by homologous recombination.

The present invention also provides pharmaceutical compositions which provide ARPs. Such compositions can comprise a pharmaceutically acceptable carrier or excipient. The composition, if desired, can also contain minor amounts of wetting or emulsifying agents, or pH buffering agents. The composition can be a liquid solution, suspension, emulsion, tablet, pill, capsule, sustained release formulation, or powder.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The composition can be formulated in accordance with routine procedures as a pharmaceutical composition adapted for intravenous administration to a subject. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In one embodiment, purified Apicomplexan organisms are given orally. In a specific embodiment, intact sporulated oocysts of an Apicomplexa genus (e.g., *Eimeria* species, such as *E. tenella*) are given orally with drinking water.

In addition to the formulations described previously, the compositions may also be formulated as a depot preparation. Such long acting formulations may be administered by implantation (for example, subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the composition of the invention in pharmaceutically acceptable form. The composition in a vial of a kit of the invention may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a container a pharmaceutically acceptable solution (e.g., saline, dextrose solution, etc.), preferably sterile, to reconstitute the composition to form a solution for injection purposes.

In another embodiment, a kit of the invention further comprises a needle or syringe, preferably packaged in sterile form, for injecting the formulation, and/or a packaged alcohol pad. Instructions are optionally included for administration of the formulations of the invention by a clinician or by the patient.

In some embodiments, the present invention provides kits comprising a plurality of containers each comprising a pharmaceutical formulation or composition comprising a dose of the composition of the invention sufficient for a single administration.

In a specific embodiment, a kit comprises a first container containing a pharmaceutical composition that provides ARP; and a second container containing a different treatment modality in an amount that, when administered before, concurrently with, or after the administration of the pharmaceutical composition that provides ARP in the first container, is effective to improve overall treatment effectiveness over the effectiveness of the administration of each component alone, or is effective to decrease side effects of the treatment when each component is used alone. In a specific embodiment, the invention provides a kit comprising in a first container, a composition of the invention; and in a second container, a composition comprising a purified immunostimulatory agent.

The appropriate and recommended dosages, formulation and routes of administration for treatment modalities such as chemotherapeutic agents, radiation therapy and biological/immunotherapeutic agents such as cytokines are known in the art and described in such literature as the Physician's Desk Reference (56th ed., 2002).

EXAMPLES

Example 1

.rBBX-01 is Well Tolerated in Toxicity Control Animals

Materials and Methods:

Animals: Specific pathogen-free female BALB/c mice weighing 18-21 g were obtained from Charles River Laboratories (Wilmington, Mass.). They were caged in shoebox-style polycarbonate cages with stainless steel tops and fed standard mouse chow and tap water ad libitum. They underwent a 24 h quarantine before being used in this study.

Virus: Influenza A/NWS/33 (H1N1) virus was originally obtained from the University of Michigan (Ann Arbor). It was passaged through MDCK cells and titrated in mice prior to use in this study.

Compounds: rBBX-01 (Barrogen; see PCT/US2004/023113 (published as WO 2005/010040)) was provided in dosages of 5000, 500, 50, 5 and 0.5 ng/kg/day; assuming a 20 g mouse weight. Ribavirin, used as a positive control drug, was obtained from ICD Pharmaceuticals, Inc. (Costa Mesa, Calif.); it was prepared at a dosage of 75 mg/kg/day in sterile physiological saline. All materials were stored at 4° C. until used.

Arterial Oxygen Saturation (SaO2) Determination: ($SaO_2$) was determined using the Ohmeda Biox 3800 pulse oximeter (Ohmeda, Louisville, Ohio). The ear probe attachment was used, the probe placed on the thigh of the animal. Readings were made after a 30 sec stabilization time on each animal. Use of such an instrument for measuring effects of influenza virus on $SaO_2$ in mammals has been previously described (Sidwell et al., *Antimicrob. Ag. Chemother.* 1992; 36:473-476).

Lung Virus Titer Determination: Each mouse lung was homogenized and varying dilutions assayed in triplicate for infectious virus in MDCK cells as described (Sidwell et al. *Antiviral Res.*, 1985, 6:343-353. Each lung homogenate was centrifuged at 2000 g for 5 min and the supernatants used in these assays. Development of viral cytopathic effect in the cells after 72 h incubation was considered indicative of virus titer.

Lung Score and Weight Determination: Lungs were taken form the mice and assigned a score ranging from 0 to 4, based on the degree of plum coloration seen: 0=normal lungs (standard pink color), 1=~25% of lung showing plum coloration; 2=~50% of lung showing plum coloration; 3=~75% of lung showing plum coloration; 4=100% of lung showing plum coloration. The lungs were also weighed at the same time; as the lung becomes more consolidated due to fluid accumulation, it gains weight. Normal lungs may weigh as little as 100-150 mg; lungs with 4+ consolidation may weigh up to 400 mg. (Sidwell et al., *Anitriviral Research* 1998; 37:107-120; Sidwell et al., *Antimicrob. Agents Chemother.* 2001; 45: 749-757)

Experiment Design: Mice were infected intranasally (i. n.) with an LD95 dose of influenza virus after anesthetization with i.p. injection of Ketamine (100 m.g./kg). Groups of 20 infected mice were treated i.p. with rBBX-01 at doses of 5000, 500, 50, 5, and 0.5 ng/kg/day once daily for 5 days beginning 24 h post-virus exposure. A similar group of mice was treated i.p. with ribavirin (75 mg/kg/day) twice daily for 5 days beginning 4 h pre-virus exposure. A group of 30 infected mice was treated with sterile saline in parallel with the rBBX-01-treated animals to act as placebo controls. Ten mice in each drug-treated group and 20 saline-treated mice were observed daily for 21 days with deaths recorded daily. These animals were also assayed for $SaO_2$ decline on days 3-11, when this parameter traditionally exhibited the greatest changes. From the remaining animals, 5 were killed on days 3 and 5 and their lungs assigned a consolidation score ranging from 0 (normal) to 4 (maximal plum coloration), weighed, and assayed for virus titer. As toxicity controls, 3 uninfected mice were treated in parallel to the above with each drug dosage; these animals were weighed immediately prior to initial treatment and again 18 h after final treatment and observed for death for 21 days. Three normal controls were also weighed and SaO2 determined in parallel with the above, and 3 additional were killed and their lungs taken as above to provide background data.

Statistical Analysis: Increases in total survivors were evaluated by chi square analysis with Yates' correction. Increases in mean day to death, differences in mean $SaO_2$ values, mean lung weight, and mean lung virus titers were analyzed by t test. The Wilcoxon ranked sum analysis was used for mean lung score comparisons.

Results:

The results of this study are summarized in Table 1 and in FIGS. 1-4. 95% of the saline-treated animals were killed by the viral challenge with a mean day to death of 9.5 days. Delay in mean day to death was 0.8 days (P>0.05) with the highest dosage-treated animals. Arterial oxygen saturation decline was inhibited by treatment with this drug (FIG. 1), and a dose-response effect was seen. The SaO2 decline was significantly inhibited on days 7 and 8 when the highest dose, i.e., 5000 ng/kg/day, was used. However, by the end of the assay times, on day 11, no differences were seen between the drug-treated and the saline-treated groups. Lung scores on day 3 were significantly inhibited by the 5000 and 500 ng/kg/day doses (FIG. 2), but by day 5, the lung scores were greater than seen in the placebo-treated animals. Modest lessening of lung weight increased (FIG. 3), which is a good measure of lung consolidation as the lungs fill with fluid, was seen in some of the drug-treated groups on day 2; this effect was observed to persist on day 6 at the 500 ng/kg/day dose only. No inhibition of lung virus titers was observed at either time the lungs were assayed (FIG. 4).

TABLE 1

| | | Tox Controls | | Infected, Treated Mice | | |
|---|---|---|---|---|---|---|
| Compound* | Dosage (ng/kg/day) | Surv/ Total | Mean Host Weight change[b](g) | Surv/ Total | Mean Day to Death[c] ± SD | Mean Day 11 SaO$_2$ (% ± SD) |
| rBBX-01 | 5000 | 3/3 | 0.3 | 0/10 | 10.3 ± 1.6 | 76.3 ± 2.6 |
| | 500 | 3/3 | 0.8 | 0/10 | 9.9 ± 2.3 | 77.3 ± 4.8 |
| | 50 | 3/3 | 1.2 | 0/10 | 8.7 ± 1.2 | 75.0 ± 0.0 |
| | 5 | 3/3 | 0.3 | 0/10 | 8.9 ± 1.6 | 75.0 ± 0.0 |
| | 0.5 | 3/3 | 0.0 | 0/10 | 9.1 ± 1.1 | 75.0 ± 0.0 |
| Ribavirin | 75 (mg/kg/day) | 3/3 | −0.8 | 10/10*** | >21.0 ± 0.0*** | 85.1 ± 2.6*** |
| Saline | — | — | — | 1/20 | 9.5 ± 2.1 | 76.8 ± 3.6 |
| Normal Controls | — | 3/3 | 1.1 | — | — | 87.3 ± 4.0 |

[a]rBBx: pd × 5 beg. 24 h post-virus exposure; Ribavirin: bid × 5 beg. 4 h pre-virus exposure.
[b]Difference between initial weight and weight 18 hours after final treatment.
[c]Mean day to death of mice dying prior to day 21.
[d]Arterial Oxygen Saturation
*P > 0.05,
**P > 0.01,
***P > 0.001

The striking antiviral effect of ribavirin, run as a positive control drug, was exerted as expected, with 100% protection from death and statistically significant inhibition of $SaO_2$ decline, lung scores, lung weights, and lung virus titers. rBBX-01 was well tolerated by the toxicity control animals, with the treated animals all surviving and gaining weight during therapy. By contrast, ribavirin was slightly toxic as indicated by a 0.8 g weight loss during the treatment period. Ribavirin was used at a dose approaching the maximum tolerated in order to achieve the antiviral effect desired.

Conclusion:

rBBX-01 was evaluated against an influenza A/NWS/33 (H1N1) virus infection in young adult mice utilizing an intraperitoneal treatment route with the material administered once daily for 5 days beginning 24 h post-virus exposure. Death or significant delay in mean day to death of the mice was not prevented, but the highest doses (5000, 500 ng/kg/day) were inhibitory to arterial oxygen saturation decline and lung consolidation relatively early in the infection. The compound was well tolerated in toxicity control animals. Ribavirin, run as a positive control, was markedly inhibitory to the infection as expected. The latter drug was administered intraperitoneally twice daily for 5 days beginning 4 h pre-virus exposure.

Example 2
rBBX-01 has a Significant Influenza-Inhibitory Effect

Materials and Methods:
Animals and Virus used and Arterial Oxygen saturation, Lung Virus Titer Determination, Lung Score Determination, Results:

This study is summarized in Table 2, with $SaO_2$ effects, lung scores, lung weights, and lung virus titers shown in FIGS. 5-8, respectively. The column in Table 2 labeled "Dosage (ng/kg/day)" should read "Dosage (ng/mouse/day)." 90% of the placebo treated animals were killed by the viral challenge, with a mean day to death of 11.3 days. This was considered within the range of lethality expected to acceptably evaluate the antiviral efficacy of test materials.

TABLE 2

| | | | Tox Controls | | Infected, Treated Mice | | |
|---|---|---|---|---|---|---|---|
| Compound* | Dosage (ng/kg/day) | Treatment Schedule* | Surv/ Total | Mean Host Weight Change[b](g) | Surv/ Total | Mean Day to Death[c] ± SD | Mean Day 11 $SaO_2$ (% ± SD) |
| rBBX-01 | 100 | d-2, 0, 3, 6 | 3/3 | 0.8 | 0/10 | 12.3 ± 1.2* | 75.3 ± 0.7 |
| | 100 | d0, 3, 6 | 3/3 | 0.7 | 2/10 | 12.1 ± 1.6 | 76.0 ± 1.9 |
| | 1,000 | d0, 3, 6 | 3/3 | 1.0 | 3/10 | 12.7 ± 2.7 | 76.5 ± 1.9* |
| | 10,000 | d0, 3, 6 | 3/3 | 1.2 | 5/10* | 12.0 ± 1.4* | 77.6 ± 3.0** |
| Placebo | — | d0, 3, 6 | — | — | 2/20 | 11.3 ± 1.2 | 75.2 ± 0.7 |
| Normal Controls | — | — | 3/3 | 1.2 | — | — | 92.0 ± 4.0 |

[a]Day 0: 4 h post-virus exposure.
[b]Difference between initial weight and weight 18 hours after final treatment.
[c]Mean day to death of mice dying prior to day 21.
*$P < 0.05$,
**$P < 0.01$,
***$P < 0.001$ Lung Weight Determination and Statistical Analysis were as described in Example 1, supra.

Compounds: rBBX-01 was in dosages of 10,000, 1,000, and 100 ng/mouse/injection. The materials were stored at 4° C. until used.

Experiment Design: Mice were infected intranasally (i.n.) with an LD90 dose of influenza virus after anesthetization with i.p. injection of Ketamine (100 mg/kg). A group of 20 infected mice were treated i.p. with rBBX-01 at a dose of 100 ng/mouse/day on day −2 (48 h pre-virus exposure), 0 (4 h post-virus exposure), 3, and 6. Groups of 20 infected mice were also treated with the compound at doses of 10,000, 1,000, or 100 ng/mouse/day on day 0 (4 h post-virus exposure), 3, and 6. A group of 30 infected mice were treated with placebo BSA (in phosphate-buffered saline) in parallel with the rBBX-01-treated animals to act as placebo controls. Ten mice in each drug-treated group and 20 saline-treated mice were observed daily for 21 days with deaths recorded daily. These animals were also assayed for $SaO_2$ decline on days 3-11. From the remaining animals, 5 were killed on days 3 and 5 and their lungs assigned a consolidation score ranging from 0 (normal) to 4 (maximal plum coloration), weighed, and assayed for virus titer. As toxicity controls, 3 uninfected mice were treated in parallel to the above with each drug dosage; these animals were weighed immediately prior to initial treatment and again 18 h after final treatment and observed for death for 21 days. Three normal controls were also weighed and $SaO_2$ determined in parallel with the above, and 3 additional were killed and their lungs taken as above to provide background data.

Treatment with rBBX-01 on days 0, 3, and 6, particularly with the highest (10,000 ng) dosage, was significantly inhibitory to the infection as seen by a 50% prevention of death, a delay in mean day to death, lessened $SaO_2$ decline, and inhibition of day 5 lung scores. A slight (0.2 loglo) inhibition of lung virus titer was seen on both days 3 and 5. The efficacy of the compound was dose responsive, with moderate inhibitory effects seen using 1,000 and 100 ng dose. Use of 1,000 and 100 ng doses was less efficacious in preventing deaths of the mice, although a one day delay in mean day to death was seen. $SaO_2$ decline was significantly lessened, lung scores and lung weight increases were inhibited, and a 0.5 $log_{10}$ inhibition of lung virus titer was seen on day 3.

rBBX-01 was well tolerated at every dose used in the toxicity control mice; indeed, the animals were to gain more weight as the dosage increased. Since rBBX-01 is apparently acting as an immune modulator, such observations are not unusual since compounds may exert different immune effects as dosages are changed.

Conclusion:
rBBX-01 was administered i.p. to mice infected with influenza A/NWS/33 (H1N1) virus using either a day −2, 0, 3, and 6 or at day 0, 3, and 6 treatment schedule. The latter schedule employed three doses: 10,000, 1,000, or 100 ng/mouse/injection, whereas in the pre-treatment schedule only 100 ng/mouse/injection was used. It was concluded that treatments were moderately efficacious in inhibiting the progress of the infection, with the later treatment schedule being most effective. A dose responsive effectiveness was seen, the highest dosage preventing deaths in 50% of the infected animals. All dosages were tolerated in toxicity control mice.

These data suggest rBBX-01 to have a significant influenza-inhibitory effect; this effect may be associated with an inhibition of lung virus titer, since some reductions in these titers were seen at all doses. A reduction of lung virus by one-half $\log_{10}$ is often sufficient to afford significant prevention of the usual lethal effects of the virus. It was unclear whether this virus titer-inhibitory effect, which could have been greater at earlier times in the infection, was due to a direct antiviral effect of the compound or to stimulated immunological mechanisms that were acting on the virus.

In Example 1, treatment was i.p. once daily for 5 days beginning 24 h pre-virus exposure. Such a frequent repetition of treatment may have over-stimulated the host immune state, leading to a hypo responsiveness that would have adversely affected the progress of the disease; indeed, the anti-influenza effects seen in the experiment were much less than those observed in the present study where the repetitions in treatment were more delayed. Schedules used in Example 2 would allow the host immune state to return to near normal conditions after each stimulation had occurred.

Example 3

Specific Dose of rBBX-01 has an Inhibitory Effect of Influenza A

Materials and Methods:

Virus used and Arterial Oxygen saturation, Lung Virus Titer Determination, Lung Score Determination, Lung Weight Determination and Statistical Analysis were as described in Example 1, supra.

with rBBX-01 at dosages of 10, 100, or 500 μg/injection on days 0, 3, and 6, the day 0 treatment being 4 h post-virus exposure. Additional groups of 20 infected mice were treated with rBBX-01 at a dose of 10 μg/injection on day 0, days 0 and 3, or days 0 and 6. Ribavirin at dose of 75 mg/kg/day was administered i.p. twice daily for 5 days beginning 4 h pre-virus exposure. Placebo was administered to 30 infected mice on days 0, 3, and 6. Ten mice in each drug-treated group and 20 placebo-treated controls were observed daily for death through 21 days, and $SaO_2$ was determined on them from days 3 through 11. Of the remaining animals, 5 were killed on days 3 and 6 and their lungs were weighed, assigned a consolidation score, and assayed for virus titer. As toxicity controls, 3 uninfected mice were treated on the 3 day schedule with the two high doses of rBBX-01, and with ribavirin, in parallel to these drugs' treatment in the above infected mice. All toxicity controls were observed for death through 21 days and were weighed immediately prior to the initial treatment and 18 h after the final treatment. Five normal controls were weighed and $SaO_2$ determined as above. Three additional normal mice were killed on days 3 and 6 to provide background lung data.

Results:

The infection induced in this experiment was 100% lethal to the placebo-treated mice, with the mean day to death being 10.5±1.3 days (Table 3). This pattern of death was considered ideal for evaluation of antiviral agents.

TABLE 3

Animals: Female 18-21 g BALB/c mice
Virus: Influenza A/NWS/33 (H1N1)
Drug diluent: Vehicle supplied by Barros Res. Inst.
Treatment schedule: See below.
Treatment route: i.p.
Expt. duration: 21 days

| | | | Tox Controls | | Infected, Treated Mice | | |
|---|---|---|---|---|---|---|---|
| Compound* | Dosage (Dose/Injection) | Treatment Schedule* | Surv/Total | Mean Host Weight Change[a](g) | Surv/Total | Mean Day to Death[b] ± SD | Mean Day 11 $SaO_2$ (% ± SD) |
| EI | 100 μg | days 0, 3, 6 | 3/3 | 1.2 | 1/10 | 11.3 ± 2.6 | 76.3 ± 2.6 |
| | 500 μg | days 0, 3, 6 | 3/3 | 1.1 | 1/10 | 10.6 ± 2.9 | 75.9 ± 2.8 |
| | 10 μg | days 0, 3, 6 | nr[c] | nr | 3/10* | 11.1 ± 0.9 | 78.9 ± 5.0* |
| | 10 μg | day 0 | nr | nr | 1/10 | 13.3 ± 3.0** | 78.3 ± 4.3 |
| | 10 μg | days 0, 3 | nr | nr | 6/10*** | 15.5 ± 4.0*** | 79.6 ± 3.7** |
| | 10 μg | days 0, 6 | nr | nr | 0/10 | 12.2 ± 2.9* | 77.8 ± 3.7** |
| Ribavirin | 37.5 mg | bid × 5 beg. −4 h | 3/3 | −0.9 | 8/8*** | >21.0 ± 0.0*** | 83.5 ± 1.9*** |
| Placebo | — | days 0, 3, 6 | nr | nr | 0/20 | 10.6 ± 1.1 | 76.4 ± 2.4 |
| Normal Controls | — | — | 3/3 | 0.8 | — | — | 88.8 ± 1.9 |

[a]Difference between initial weight and weight 18 h after final treatment.
[b]Mean day to death of mice dying prior to day 21.
[c]Not run.
*$P < 0.05$,
**$P < 0.01$,
***$P < 0.001$ compared to saline-treated controls.

Animals: Female 18-21 g BALB/c mice were obtained from Charles River Laboratories (Wilmington, Mass.) for this study. They were maintained on Wayne Lab Blox and tap water ad libitum. They were quarantined for 24 h prior to use.

Compounds: rBBX-01 was provided at dosages of 500, 100, and 10 μg/0.1 ml. Ribavirin was obtained from ICN Pharmaceuticals, Inc. (Costa Mesa, Calif.).

Experiment Desigun: Mice were infected i.n. with an LD 100 dose of influenza A virus; groups of 20 were treated i.p.

rBBX-01 used at dosages of 500 and 100 μg/injection on the 3 day treatment schedule was not considered efficacious in this experiment (Table 3, FIGS. 9-12). However, the 10 μg/injection dose used in the 3 days treatment was moderately inhibitory, preventing death in 30% of the infected mice, moderately lessening $SaO_2$ decline, inhibiting lung consolidation, and inhibiting lung virus titers, the latter seen only on day 6. When this dose of rBBX-01 was administered on days 0 and 3, 60% of the animals survived with significant delay in mean day to death and inhibition of the other disease parameters (Table 3, FIGS. 9-12). Treatments with this dose on day 0 only or on days 0 and 6 only were less efficacious than the days 0 and 3 treatment schedule.

The expected activity of ribavirin was exhibited at the dosage used, preventing all infected mice from dying and inhibiting all other disease parameters.

rBBX-01 was well tolerated at the dosages used, as seen by no deaths or weight loss in toxicity controls. Ribavirin was used at approximately its maximum tolerated dose, since a weight loss of 0.9 g was seen during treatment (Table 3).

Conclusion:

Mice infected with influenza A/NWS/33 (H1N1) virus and treated i.p. with the immunomodulator E1 (rBBX-01) used at a dose of 10 µg/injection given 4 h post-virus exposure and again 3 days after virus exposure was able to prevent 60% of the mice from dying and to reduce lung consolidation and lung virus titers. Treatments with 100 or 500 µg/injection on days 0, 3, and 6 were less effective, as was use of 10 µg/injection given on day 0 or on days 0 and 6. Ribavirin, used i.p. at 75 mg/kg/day twice daily for 5 days, was highly effective against this virus infection.

These data confirm and extend our previous findings that compound rBBX-01 has a moderate inhibitory effect on influenza A virus infections in mice (see, Example 1 and 2). It was observed that two treatments spaced 3 days apart were the most efficacious to date; and the optimum dosage was 10 µg/injection. Too frequent dosing may result in a hypostimulation of the immune system a "wearing out" of the function (Sousa et al., *Immunity*, 1999; 11:637-647; Julio et al., *Immunological Reviews*, 2004; 201:26-34). Utilizing higher doses, while not apparently toxic from a clinical viewpoint, may again cause an over-stimulation of the immune function, also eventually resulting in a lessening of the needed immune response.

Many immunomodulatory substances were evaluated for efficacy against experimentally induced influenza in mice; these include ImuVert™ (sterile preparation from *Seratia marcescens*), BCH-527 (lipophilic HCl salt of octadecyl D-alanine L-glutamine), methionine-enkephalin Met-Enk, (an endogenous opioid peptide composed of a five amino acid chain), IM-862 (a natural product peptide), poly ICLC, Ampligen® (poly I · poly C12u), and a polyprenol from the Siberian silver fir (*Abies sibirica*). The efficacy of these materials were ranked as: Met-Enk>polyprenol>polyICLC>Ampligen®>IM-862=Imu Vert>BCH 527 (Sidwell et al. *Proc. Vi Int'l Symps. On Respiratory Viral Infections* 2004; Abs II-1). The efficacy of rBBX-01 was determined to be approximately the same as Met-Enk and polyprenol. It was determined in previous studies that Met-Enk in combination with an antiviral, such as ribavirin, has greater efficacy than either materials used above. It was hypothesized that such synergistic effects were due to the different mechanisms of action of each material. Such data suggest that rBBX-01 should be considered for use in combination with compounds having a more direct antiviral effect. The work done with polyprenol utilized that material administered intranasally to the infected animals; it is possible that such a treatment route may further enhance the efficacy of rBBX-01 as well.

Example 4

Combination of GM-CSF and rBBX-01 may have an Additive or Synergistic Effect on Influenza Infection in Mice Materials and Methods:

Animals and Virus used and Arterial Oxygen saturation, Lung Virus Titer Determination, Lung Score Determination, Lung Weight Determination and Statistical Analysis were described as in Example 1, supra.

Compounds: rBBX-01 was provided in dosages of 10 µg/injection. GM-CSF was provided in dosages of 200 and 20 ng/injection. All materials were stored at 4° C. until used.

Experiment Design: Mice were infected intranasally (i. n.) with an LD85 dose of influenza virus after anesthetization with i. p. injection of Ketamine (100 mg/kg). Groups of 20 infected mice were treated i. p. with GM-CSF at doses of 200 or 20 ng/mouse 4 h pre- and 3 days post-virus exposure. A similar group of mice was treated i. p. at a dose of 10 µg/mouse on the same treatment schedule. Groups of 20 mice were also treated with the combination of 200 ng/mouse of GM-CSF and 10 µg/mouse of rBBX-01 or 20 ng/mouse of GM-CSF and 10 µg/mouse of rBBX-01. A group of 30 infected mice were treated with sterile saline in parallel with the above treated animals to act as placebo controls. Ten mice in each drug-treated group and 20 saline-treated mice were observed daily, for 21 days with deaths recorded daily. These animals were also assayed for $SaO_2$ decline on days 3-11, when this parameter traditionally exhibited the greatest changes. From the remaining animals, 5 were killed on days 3 and 5 and their lungs assigned a consolidation score ranging from 0 (normal) to 4 (maximal plum coloration), weighed, and assayed for virus titer. As toxicity controls, 3 uninfected mice were treated in parallel to the above with each drug dosage; these animals were weighed immediately prior to initial treatment and again 18 h after final treatment and observed for death for 21 days. Three normal controls were also weighed and $SaO_2$ determined in parallel with the above, and 3 additional were killed and their lungs taken as above to provide background data.

Results:

The results of this study are summarized in Table 4 and in FIGS. 13-16. 85% of the saline-treated animals were killed by the viral challenge, with a mean day to death of 11.0 days. This was considered satisfactory for evaluation of antivirals.

TABLE 4

| Treatment | Dosage | Tox Controls | | Infected, Treated Mice | | |
|---|---|---|---|---|---|---|
| | | Surv/Total | Mean Host Weight change[b](g) | Surv/Total | Mean Day to Death[c] ± SD | Mean Day 11 SaO$_2$ (% ± SD) |
| GM-CSF | 200 ng | 3/3 | 0.3 | 3/10 | 9.6 ± 0.8 | 76.4 ± 2.5 |
| | 20 ng | 3/3 | 0.0 | 0/10 | 9.9 ± 1.2 | 75.0 ± 0.0 |
| E1 | 10 µg | 3/3 | 0.1 | 6/10* | 10.8 ± 2.4 | 79.5 ± 4.6 |
| GM-CSF + E1 | 200 ng + 10 µg | 3/3 | 0.6 | 7/10** | 14.0 ± 4.6 | 80.5 ± 5.3 |
| | 20 ng + 10 µg | 3/3 | 0.1 | 3/10 | 12.6 ± 4.2 | 80.1 ± 5.3 |
| Placebo | — | — | — | 3/20 | 11.0 ± 2.3 | 77.3 ± 3.6 |
| Normal Controls | — | 3/3 | 0.1 | — | — | 86.8 ± 5.3 |

[a]Treatment given 4 h pre-and 3 days post-virus exposure.
[b]Difference between initial weight and weight 18 h after final treatment.
[c]Mean day to death of mice dying prior to day 21.
*P < 0.05;
**P < 0.01;
***P < 0.001. compared to placebo-treated controls.

Figure 15:
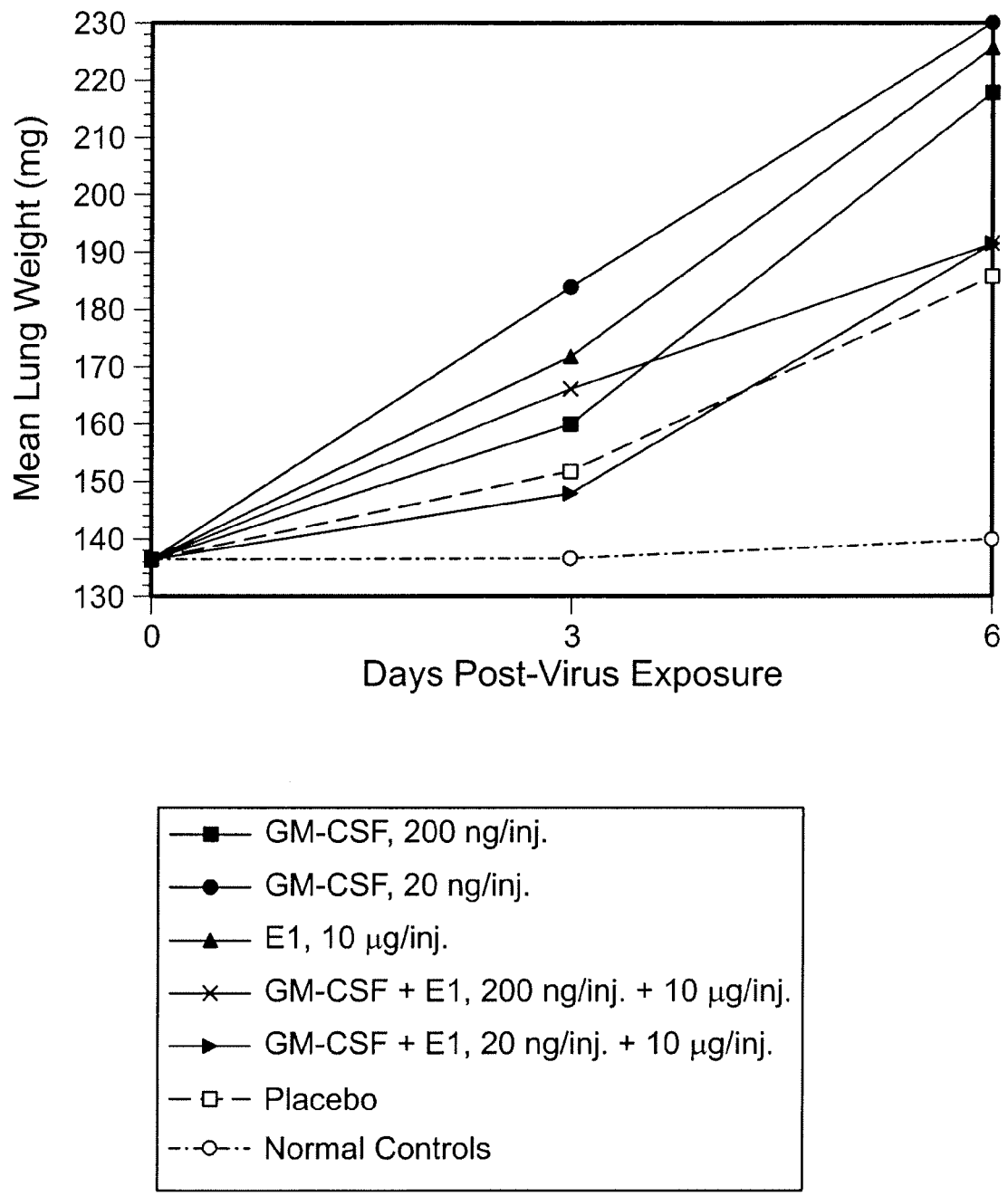
Figure 17:
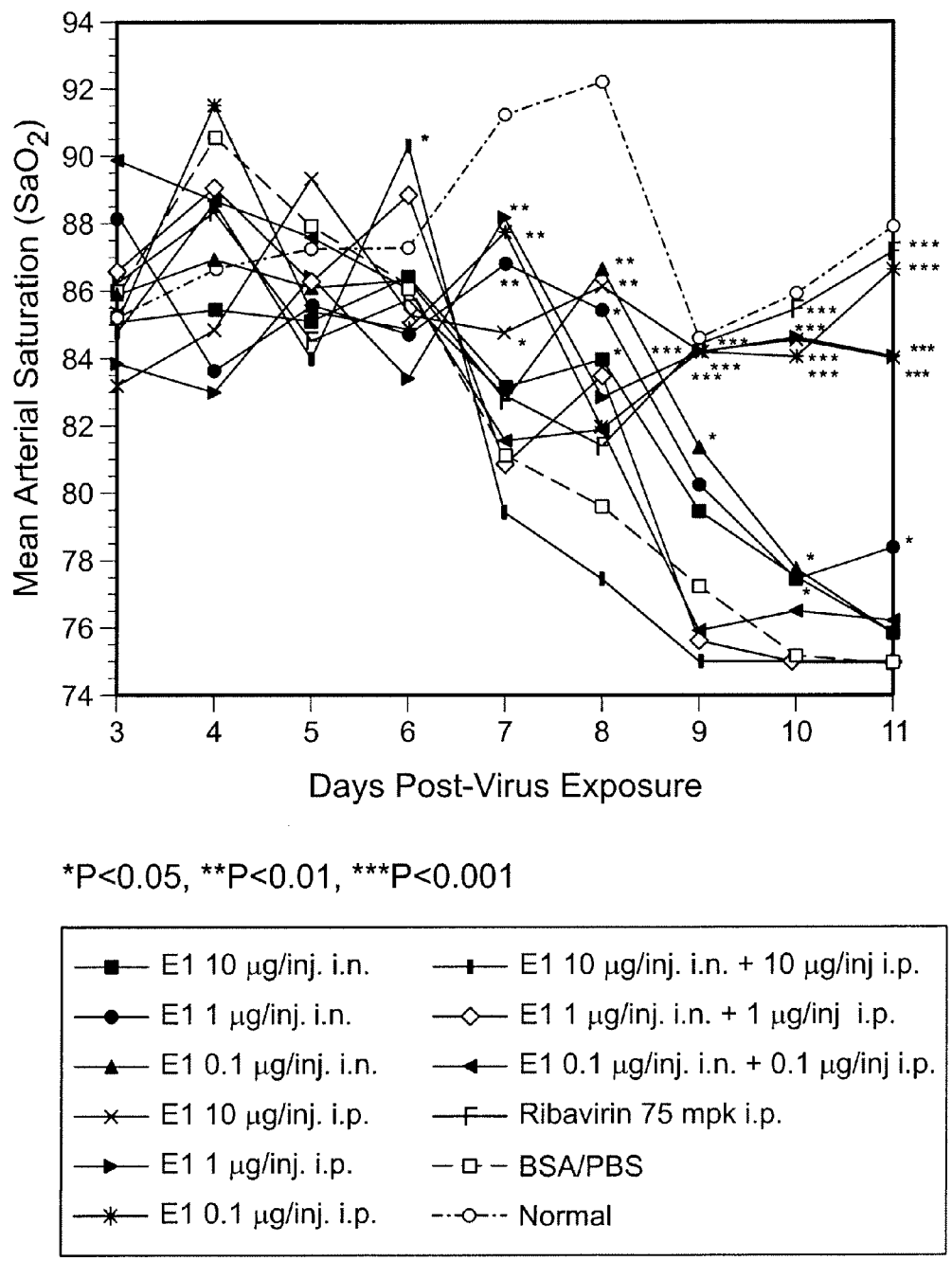
FIG. 17. Comparison of i.n., i.p., and combined i.n./i.p. treatments with E1 on the arterial oxygen saturation decline in influenza (H1N1) virus-infected mice. Mean Arterial Saturation percentage is shown on the y-axis. Days post-virus exposure is shown on the x-axis. Keys for lines representing normal controls, BSA/PBS, ribavirin and different concentrations of E1 administered intranasally, intraperitoneally or both intranasally and intraperitoneally are shown. *,  and * represent different P-values.
Figure 18:
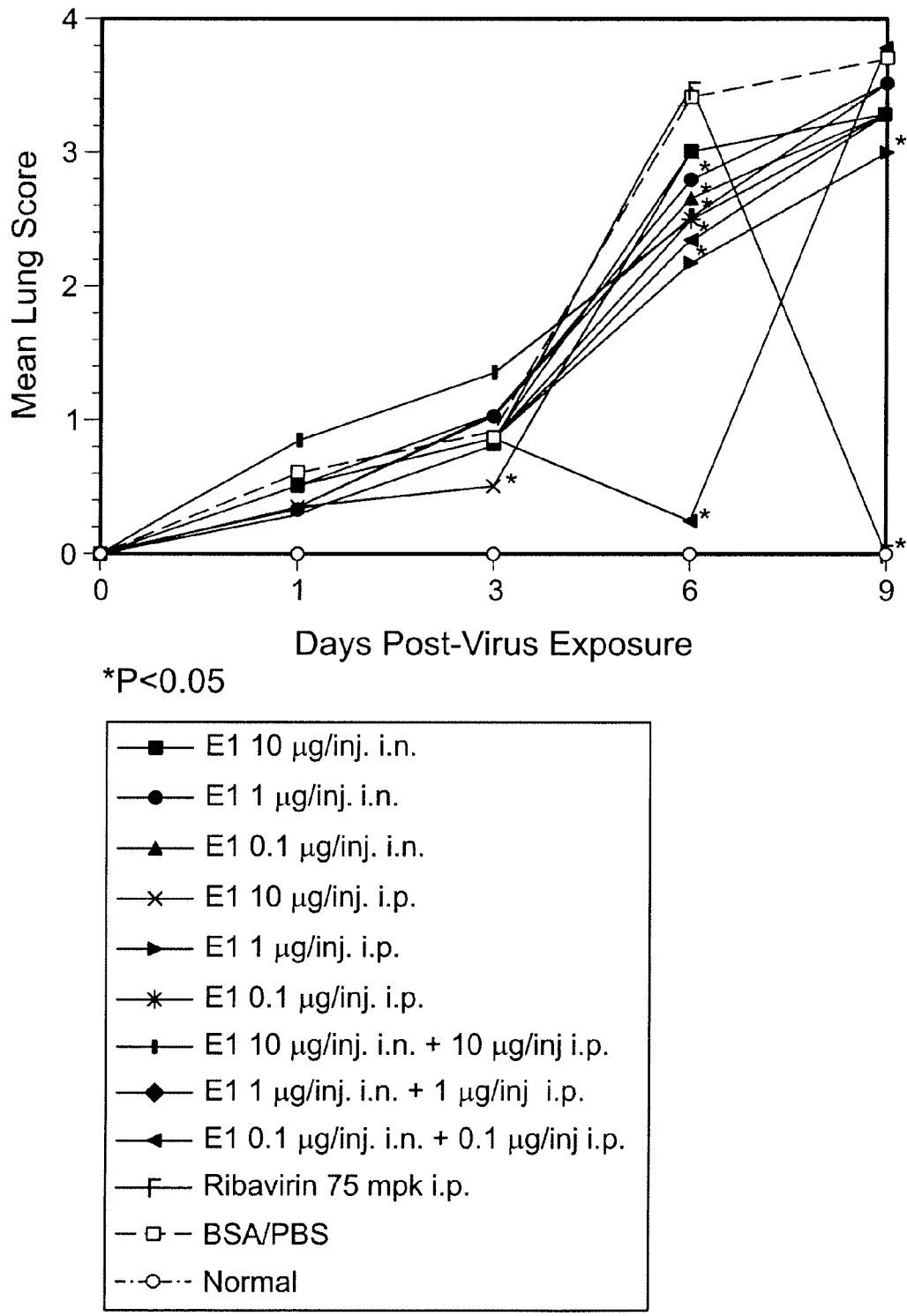
Figure 19:
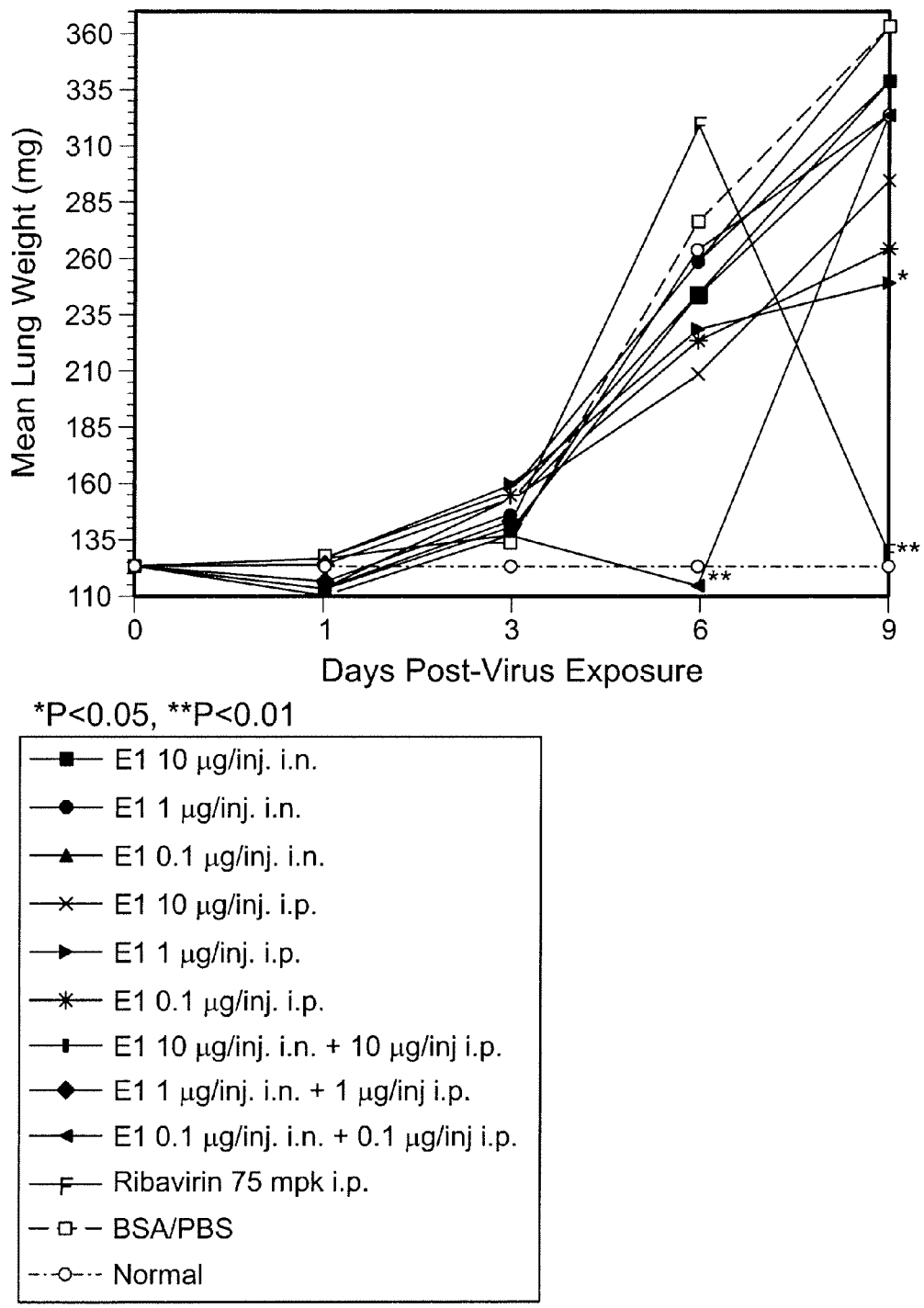
Figure 20:
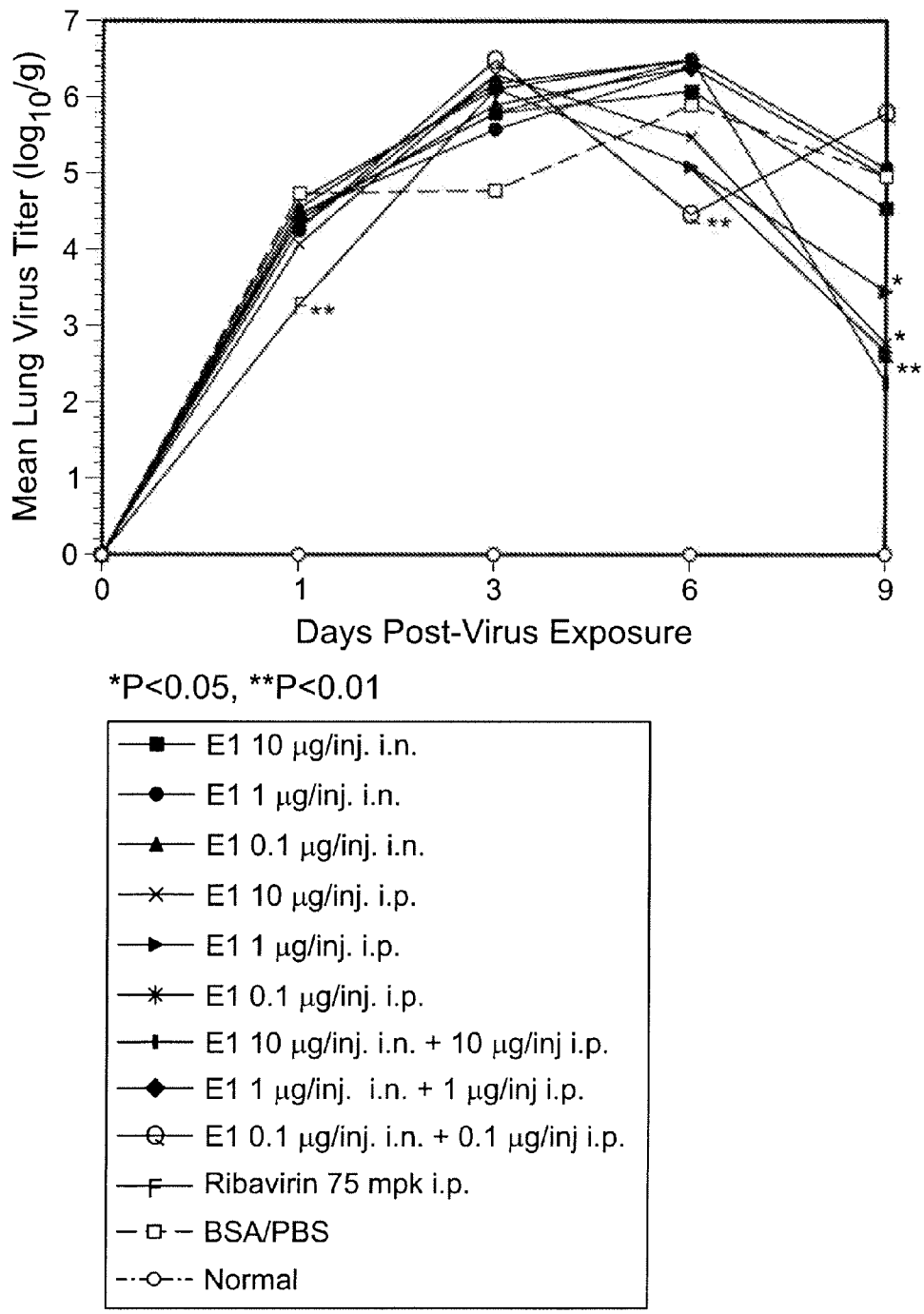

No effect was observed with the treatment of GM-CSF, with no increase in survivors, no delay in mean day to death (Table 4), essentially no inhibition of SaO$_2$ decline (FIG. 13) and no inhibition of lung weight or lung virus titers (FIGS. 15 and 16). Lung scores appeared to be significantly inhibited on day 3, however, but not on day 6 (FIG. 14).

Therapy with rBBX-01 used alone prevented deaths of 60% of the infected mice (P<0.05), although SaO$_2$ decline was not appreciably affected (FIG. 13) and lung scores were lessened only on day 6 (P>0.05). No inhibitory effect was seen on the other lung parameters (FIGS. 15 and 16).

Figure 13:
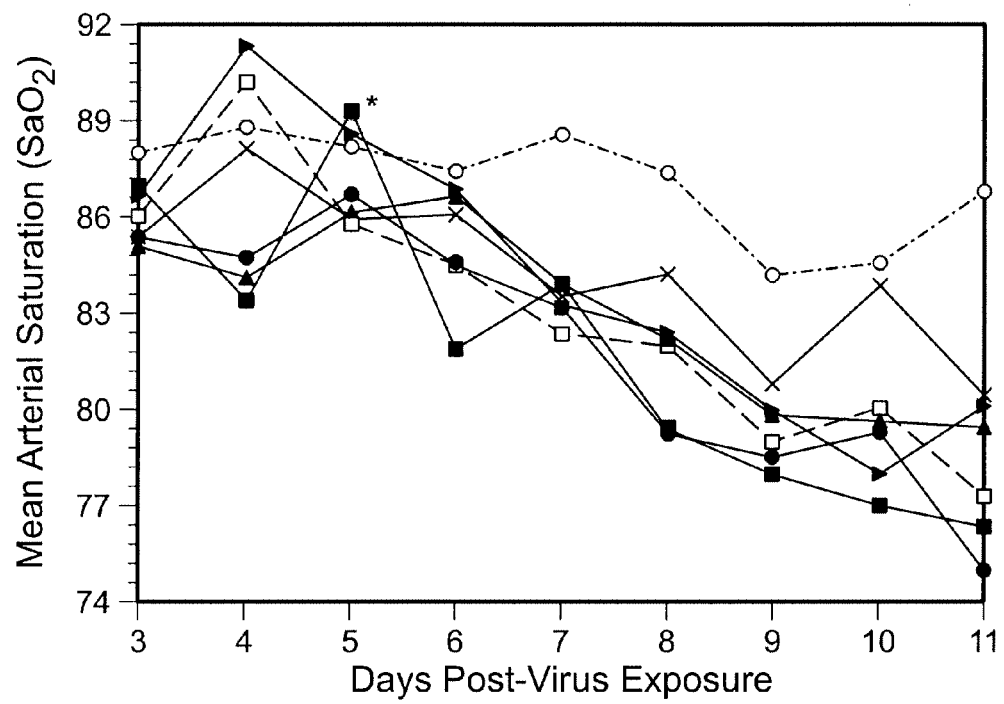

Use of the combination of rBBX-01 and the high dose of GM-CSF was observed to be slightly more effective than rBBX-01 used alone, based on a 70% survival rate of the infected mice and a 3 day extension in mean day to death (Table 4). The daily SaO$_2$ values from the infected animals receiving this drug combination were also generally higher than those using either material alone (FIG. 13). Also, on day 6, less virus titers were seen in the lungs from infected animals receiving this combination treatment than the other groups (FIG. 16), although the titer inhibition (0.3 log$_{10}$) was not statistically significant. No effect was seen on lung consolidation (FIGS. 14 and 15). No synergistic effect was observed when the combination of the lower dose of GM-CSF and rBBX-01 was used.

Both GM-CSF and rBBX-01, and their two combinations, were well tolerated by the toxicity control animals, with the treated animals all surviving and losing no weight during therapy. Higher dosages of rBBX-01 were also well tolerated but are less efficacious. The dosages of GM-CSF were selected based on other studies run in mice, but the lack of toxicity seen would suggest higher dosages could be safely utilized (Rosenberg et al., *Int. J. Cancer* 2005; 114: 756-765).

Conclusion:

rBBX-01 used alone and in combination with GM-CSF was evaluated against an influenza A/NWS/33 (H1N1) virus infection in young adult mice utilizing an intraperitoneal treatment route with the materials administered 4 h pre- and 3 days post-virus exposure. rBBX-01 used alone at 10 µg/mouse was observed to prevent deaths in 60% of the infected mice compared to 15% surviving in placebo controls. The virus infection was not inhibited with GM-CSF used at 200 and 20 ng/mouse; however, deaths of 70% of the animals were prevented by the use of the high dose GM-CSF combined with rBBX-01. SaO$_2$ decline was lessened to a greater extent than using either material alone. Both materials, used alone or in combination, were well tolerated by toxicity controls.

As shown by this Example, it is confirmed that a 10 µg/mouse dose of rBBX-01 used as described in Example 3 is efficacious against influenza A (H1N1) virus infections in mice. As demonstrated in this Example, it can be suggested that combination of the 200 ng/mouse dose of GM-CSF combined with the 10 µg/mouse dose of rBBX-01 may have had an additive or synergistic effect on this infection, although the differences between the effects of rBBX-01 and the combination were not statistically different from each other.

It would be of interest to determine if rBBX-01 would synergistically affect the antiviral activity of the influenza virus neuraminidase inhibitor oseltamivir (TamiFlu™), a clinically useful influenza virus drug. The in vivo efficacy of oseltamivir has been described (Sidwell et al., *Antiviral Res.* 1998; 37:107-120). Oseltamivir, while now used widely, is quite expensive and quantities are limited in the case of a major influenza pandemic.

Example 5 rBBX-01 has an Inhibitory Effect on Influenza A Virus Infections in Mice when Administered i.p Materials and Methods:

Virus used and Arterial Oxygen saturation, Lung Virus Titer Determination, Lung Score Determination, Lung Weight Determination and Statistical Analysis were described as in Example 1, supra.

Animals: Female 18-21 g BALB/c mice were obtained from Charles River Laboratories (Wilmington, Mass.) for this study. They were maintained on Wayne Lab Blox and tap water ad libitum. They were quarantined for 24 h prior to use.

Compounds: rBBX-01 was provided in dosages of 10,1, and 0.1 µg/0.1 ml. Ribavirin was obtained from ICN Pharmaceuticals, Inc. (Costa Mesa, Calif.).

Experiment Design: Mice were infected i.n. with an LD100 dose of influenza A virus; groups of 20 were treated i.n, i.p., or combined i.n.+i.p. with rBBX-01 at dosages of 10, 1 or 0.1 µg/injection on days 0, 3, and 6, the day 0 treatment being 4 h post-virus exposure. Those receiving the combination i.n. and i.p. treatments received a total of double the dose used for each treatment route alone. Ribavirin at a dose of 75 mg/kg/day was administered i.p. twice daily for 5 days beginning 4 h pre-virus exposure. Placebo (BSA/PBS, supplied by Barros Research Institute) was administered to 40 infected mice on days 0, 3, and 6. Ten mice in each drug-treated group and 20 placebo-treated controls were observed daily for death through 21 days, and $SaO_2$ was determined on them from days 3 through 11. Of the remaining animals, 3 were killed on days 1, 3, 6 and 9 and their lungs were weighed, assigned a consolidation store, and assayed for virus titer. As toxicity controls, 3 uninfected mice were treated on the 3 day schedule with the two high doses of rBBX-01, and with ribavirin, in parallel to these drugs' treatment in the above infected mice. All toxicity controls were observed for death through 21 days and were weighed immediately prior to the initial treatment and 18 h after the final treatment. Five normal controls were weighed and $SaO_2$ was determined as above. Three additional normal mice were killed on days 1, 3 and 6 to provide background lung data.

Results:

The infection induced in this experiment was observed to be 100% lethal to the placebo-treated mice; with the mean day to death being 8.6±1.2 days (Table 5). This pattern of death was considered ideal for evaluation of antiviral agents.

to the placebo control. Most of the other treatment groups showed little virus titer reduction, although one anomaly was seen in the i.n.+i.p treated group receiving the lowest drug dosage, which had a 1.4 $\log_{10}$ virus titer reduction. It must be pointed out that the animals from which the lung virus titers were determined were sacrificed during the experiment, and so were not counted towards the total surviving or dying of the infection.

Use of ribavirin was shown to prevent all infected mice from dying and inhibiting all other disease parameters. A 1.5 $\log_{10}$ virus titer reduction on day 1 of the infection was seen in animals treated with this positive control drug. On day 9, a 2.7 $\log_{10}$ virus titer reduction was observed in animals treated with this drug. Interestingly, on days 3 and 6, the virus titers were observed to be higher than in the placebo controls.

rBBX-01 was well tolerated at the dosages used, as seen by no deaths or weight loss in toxicity controls. Ribavirin was used at approximately its maximum tolerated dose, since a weight loss of 0.7 g was seen during treatment (Table 5).

TABLE 5

Animals: Female 18-21 g BALB/c mice
Virus: Influenza A/NWS/33 (H1N1)
Drug diluent: BSA/PBS
Treatment schedule: 4 h pre, day 2, day 5 (Ribavirin: bid × 5 beg 4 h pre)
Treatment route: as noted below
Expt. duration: 21 days

| | | | Tox Controls | | Infected, Treated Mice | |
|---|---|---|---|---|---|---|
| Compound | Dosage | Treatment Route | Surv/Total | Mean Host Weight Change$^a$(g) | Surv/Total | Mean Day to Death$^b$ ± SD | Mean Day 11 $SaO_2$ (% ± SD) |
| E1 (rBBX-01) | 10 µg/inj. | i.n. | 3/3 | 0.9 | 0/10 | 10.2 ± 2.1* | 75.9 ± 2.8 |
| | 1 µg/inj. | " | 3/3 | 0.9 | 0/10 | 11.1 ± 3.1** | 78.4 ± 5.6 |
| | 0.1 µg/inj. | " | 3/3 | 0.8 | 0/10 | 9.9 ± 1.0** | 75.8 ± 2.5 |
| | 10 µg/inj. | i.p | 3/3 | 0.5 | 9/10*** | 18.0 ± 0.0*** | 84.1 ± 4.6*** |
| | 1 µg/inj. | " | 3/3 | 0.6 | 8/10*** | 13.5 ± 0.7*** | 84.1 ± 4.0*** |
| | 0.1 µg/inj. | " | 3/3 | 0.4 | 10/10*** | >21.0 ± 0.0*** | 86.7 ± 7.9*** |
| | 10 µg/inj. | i.p + i.n. | 3/3 | 0.4 | 0/10 | 8.5 ± 0.7 | 75.0 ± 0.0 |
| | 1 µg/inj. | " | 3/3 | 0.6 | 0/10 | 9.0 ± 0.5 | 75.0 ± 0.0 |
| | 0.1 µg/inj. | " | 3/3 | 0.0 | 1/10 | 8.8 ± 0.7 | 76.2 ± 3.8 |
| Ribavirin | 75 mg/kg/day | i.p. | 3/3 | −0.7 | 10/10*** | >21.0 ± 0.0 | 87.2 ± 5.5*** |
| BSA/PBS | — | i.p. + i.n. | — | — | 0/18 | 8.6 ± 1.2 | 75.0 ± 0.0 |
| Normal Controls | — | — | 3/3 | 0.9 | — | — | 88.0 ± 1.0 |

$^a$Difference between initial weight and weight 18 h after final treatment.

All three dosages of rBBX-01 used in this study when used i.p, were highly effective at, with 8 to 10 animals surviving in each treatment group. Marked lessening of $SaO_2$ decline was observed at all doses. Significant inhibition was seen on a scattered basis on lung weights and lung scores as well. The animals treated i.n. or using combined i.n.+i.p: were not observed to survive the infection, with the exception of the combined i.n.+i.p. treated group receiving the lowest dose of rBBX-01, where one animal survived. The i.n. treatments at all dosages did significantly slow the mean time to death of the mice, however, and some inhibition of $SaO_2$ decline was also seen, but to a lesser extent than when the compound was administered i. p. The combined treatments were seen to have little effect on $SaO_2$ decline (Table 5; FIGS. 17-20).

Early in the infection (day 1), a 0.7 $\log_{10}$ titer reduction was seen with the i.p. administered 10 μg dose, although the other dosages had little effect. On day 6, the mean lung virus titers in all groups treated i.p: were reduced 0.4-0.8 $\log_{10}$ compared Conclusion:

In our experience with influenza virus, if the titer can be reduced by as little as 0.5 $\log_{10}$, this can often result in complete protection of the mice.

Mice infected with influenza A/NWS/33 (H1N1) virus and treated i.p. with the immunomodulator E1 (rBBX-01) used at a dose of 10, 1, or 0.1 μg/injection were significantly protected from the virus infection as seen by most of the animals surviving the infection, showing significantly less $SaO_2$ decline, and some scattered lessening of lung consolidation and lung virus titers. Therapy was on days 0 (4 h pre-virus exposure), 3, and 6. Treatment with the same dosages i.n. or i.n.+i.p. were less effective, although no enhancement of toxicity was seen. The material seemed well tolerated by all toxicity control animals. Ribavirin, run in parallel in the study, was administered i. p. at a dose of 75 mg/kg/day twice daily for 5 days beginning 4 h pre-virus exposure; it was also highly effective against this virus infection.

These data confirm and extend the previous findings as demonstrated in Examples 1-4 that rBBX-01 has an inhibitory effect on influenza A virus infections in mice when administered i.p., but these effects are lessened using i.n. and lessened further when used i.n. and i.p. in the same treatment group. At this point, it is unclear why the combination treatment was worse than either treatment used alone; this was apparently not due to enhanced toxicity, since all the toxicity control animals gained weight. It is apparent that the immunomodulatory effects required to protect the animals are in some manner reduced by the combination of treatment routes. It should be pointed out, however, that the actual dosages given to the animals receiving both i.n. and i.p. treatments were double those given by i.p. or i.n. therapy alone. It is possible that the antiviral effects may not have been lessened to the same extent if an equivalent dosage had been given.

Example 6 rBBX-01 Protects 100% of Mice Infected with Punta Toro Virus

Materials and Methods:

Animals: Female 12-14 g C57BL/6 mice were obtained from Charles River Laboratories (Wilmington, Mass.) and quarantined for a minimum 48 hours prior to experimentation. They were fed standard mouse chow and tap water ad libitum.

Virus: Punta Toro virus, Adames strain, was provided by the U. S. Army Medical Research Institute for Infectious Diseases, Ft. Detrick (Frederick, Md.). The virus used in these experiments was from a stock prepared following 4 passages of the original virus stock through LLC-MK2 (rhesus monkey, kidney) cells. Virus was inoculated into mice via the subcutaneous route. Punta Toro virus serves as a model for Rift Valley Fever virus and Sand Fly Fever virus infections in humans (Sidwell et al., *Annals of the New York Academy of Sciences* 1992; 635:344-355).

Compounds: Barrogen and 0.1% BSA/PBS vehicle (placebo) were provided by Barros Research Institute (Holt, Mich.). Ribavirin served as the positive control and was supplied by ICN Pharmaceuticals, Inc. (Costa Mesa, Calif.). Ribavirin was dissolved in sterile saline for these experiments.

Liver and serum virus titers: Virus titers were assayed using an infectious cell culture assay as previously described (Sidwell et al., *Antimicrob Agents Chemother.* 1988; 32:331-336). Briefly, a specific volume of liver homogenate or serum was serially diluted and added to triplicate wells of LLC-MK2 cell monolayers in 96-well microplates. The viral cytopathic effect (CPE) was determined 6 days post-virus exposure and the 50% endpoints were calculated as described (Reed et al., *Am. J. Hyg.* 1938; 27:493-497).

Serum Alanine aminotransferase (ALT) determinations: Detection of ALT in serum is an indirect method for evaluating liver damage. Serum ALT levels were measured using the ALT (SGPT) Reagent Set purchased from Pointe Scientific, Inc. (Lincoln Park, Mich.) following the manufacturer's recommendations. The reagent volumes were adjusted for analysis on 96-well microplates.

Experimental design: Mice were randomly assigned to four treatment groups (group descriptions and the number of animals per group are shown in Table 6). The mice were injected i.p. with placebo, 1 or 0.1 μg of Barrogen 4 h pre- and 48 h post-inoculation. Ribavirin (75 mg/kg/day) treatments were administered twice daily and continued for a total of 5 days. Four hours after the initial treatment, 20 mice from each group (30 for the Placebo group and 15 for the ribavirin group) were challenged s.c. with 2 times $10^4$ $CCID_{50}$ of PTV. Ten animals from each group (five for the ribavirin group) were sacrificed at day 3 and their livers were removed, weighed, and scored on a scale of 0-4 for hepatic icterus; 0 being normal and 4 being maximal yellow coloration. Serum was collected for ALT determinations and virus titers were evaluated for both liver and serum samples as described above. The remaining animals in each group were observed for death out to 21 days. To assess potential toxicity associated with the test drug, 3 uninfected mice from each treatment group were observed for death and their weights measured on day —1 and 5 or 6. For comparison, three sham-infected animals were included as normal controls in order to establish baselines for all parameters tested.

TABLE 6

Animals: Female 12-14 g C57BL/6 mice
Virus: Punta Toro, Adames strain
Drug diluent: 0.1% BSA in PBS (Ribavirin: Saline)
Treatment schedule: 2 treatments, −4 h and 48 h (Ribavirin: bid × 5 beg −4 h)
Treatment route: i.p.
Expt. duration: 21 days

| | | Tox Controls | | Infected, Treated Mice | | |
|---|---|---|---|---|---|---|
| Compound | Dosage | Surv/ Total | Mean Host Weight Change[a] (g) | Surv/ Total | Mean Day to Death[b] ± SD | Mean Liver Score ± SD |
| Barrogen | 1 μg/day | 3/3 | 0.8 | 11/11*** | >21.0 ± 0.0*** | 0.8 ± 0.7* |
| | 0.1 μg/day | 3/3 | 0.2 | 10/10*** | >21.0 ± 0.0*** | 1.8 ± 1.0 |
| Ribavirin | 75 mg/kg/day | 3/3 | 0.6 | 10/10*** | >21.0 + 0.0*** | 0.0 ± 0.0*** |
| 0.1% BSA/PBS | — | 3/3 | 1.2 | 2/21 | 5.3 ± 1.4 | 1.9 ± 1.3 |
| Normal Controls | — | — | — | — | — | 0.0 ± 0.0 |

[a]Difference between initial weight and weight on day 5 post-inoculation.
[b]Mean day to death of mice dying prior to day 21.
*P < 0.05;
***P < 0.001 compared to 0.1% BSA/PBS-treated controls.

Additionally, Barrogen was given as a single dose 24 h post-infection and the number of sacrificed animals was reduced to five animals in all treatment groups but placebo. Dosages used are indicated in Table 7.

inoculum of PTV (Table 7). Hepatic icterus was reduced by 17-43% with Barrogen treatment. As before, the toxicity control mice appeared healthy and gained weight, indicating no overt toxicity resulting from treatment. Analysis of liver virus

TABLE 7

Animals: Female 12-14 g C57BL/6 mice
Virus: Punta Toro, Adames strain
Drug diluent: 0.1% BSA/PBS (Ribavirin: Saline)
Treatment schedule: Single dose, 24 h (Ribavirin: bid × 5 beg −4 h)
Treatment route: i.p.
Expt. duration: 21 days

| | | Tox Controls | | Infected, Treated Mice | | |
|---|---|---|---|---|---|---|
| Compound | Dosage | Surv/Total | Mean Host Weight Change$^a$ (g) | Surv/Total | Mean Day to Death$^b$ ± SD | Mean Liver Score ± SD |
| Barrogen | 1 µg | 3/3 | 2.6 | 11/11*** | >21.0 ± 0.0*** | 2.6 ± 0.2 |
| | 0.1 µg | 3/3 | 2.3 | 11/11*** | >21.0 ± 0.0*** | 2.7 ± 0.3 |
| | 0.01 µg | 3/3 | 1.8 | 11/11*** | >21.0 ± 0.0*** | 2.0 ± 0.6 |
| | 0.001 µg | 3/3 | 2.1 | 11/11*** | >21.0 ± 0.0*** | 2.9 ± 0.5 |
| Ribavirin | 75 mg/kg/day | 3/3 | 2.4 | 11/11*** | >21.0 ± 0.0*** | 1.2 ± 0.4** |
| 0.1% BSA/PBS | — | 3/3 | 3.1 | 3/20 | 5.2 ± 0.8 | 3.5 ± 0.6 |
| Normal Controls | — | — | — | — | — | 0.0 ± 0.0 |

$^a$Difference between initial weight and weight on day 6 post-inoculation.
$^b$Mean day to death of mice dying prior to day 21.
**P < 0.01;
***P < 0.001 compared to 0.1% BSA/PBS-treated controls Statistical analysis: The Fisher's exact test (two-tailed) was used for evaluating increases in total survivors. The Mann-Whitney test (two-tailed) was performed to analyze the differences in mean day to death, virus titers, and serum ALT levels. Wilcoxon ranked sum analysis was used for mean liver score comparisons.

Results:

Barrogen was given as a two-dose regimen (0.1 or 1 µg doses) beginning 4 h prior to PTV challenge and a follow-up treatment 48 h post-infection. As shown in Table 6, both Barrogen treatments protected 100% of mice and the 1 µg dose significantly reduced the hepatic icterus comm Mass.). Mice were allowed to reside at the Laboratory Animal Resource Center (LARC) at Utah State University for 1 week prior to the beginning of the experiment. All animals were fed standard mouse chow and tap water ad libitum.

Virus: Banzi virus (H336 strain) was obtained from ATCC. The virus was passaged 3 times in vero cells.

Compounds: The interferon inducer Ampligen® (HEMI-SPHERx, Philadelphia, Pa.) was served as a positive control. Ampligen® was provided as a viscous 2.4 mg/mL solution (stored at −20°) and was diluted in sterile water to the appropriate concentration. All administrations of Barrogen and Ampligen® were performed via the intraperitoneal (i.p.) route.

Brain virus titers: The virus titer in tissues were assayed using the virus yield assay where a specific volume of tissue homogenate was added to the first tube of a series of dilution tubes (Morrey et al. *Antiviral Res.* 2002; 55:107-116). Serial $\log_{10}$ dilutions were made and added to Vero cells. Five days later the CPE was used to identify the end-point of infection. Four replicates were used to calculate the infectious doses per gram of tissue. Results were reported as $\log_{10}$ infectious units/gram of tissue or milliliter of serum.

Experiment Design: Animals were injected i.p. with either $10^{-3}$ dilution of Banzi virus stocks diluted in minimal essential media (MEM), or were sham-inoculated. This virus concentration had previously produced approximately 90% mortality in mice. Animals were treated with two doses of 10, 1, 0.1 μg/mouse of Barrogen or with drug vehicle (placebo group). The first dose was administered 4-6 h prior to virus inoculation. The second dose was given 48 h later. As a positive control a group of 15 infected mice were treated with a single dose of Ampligen® 24 h prior to virus inoculation at a dose of 1 mg/kg. Groups of 3 sham-inoculated animals used as toxicity controls were treated with identical compounds on identical schedules to the infected animals.

At 8 day post-virus inoculation (dpi) 5 animals from each treatment group were euthanized and brain tissue was weighed and collected for virus titration. Remaining animals were monitored for death until 21 dpi. Additionally, whole body weight was measured on 0, 6-8, and 21 dpi.

Statistical Analysis: Differences in total survivors between the different populations of mice was evaluated by chi square analysis with Yates correction. Differences in tissue titer, mean day to death (MDD), and whole body weight were analyzed by t test.

Figure 21:
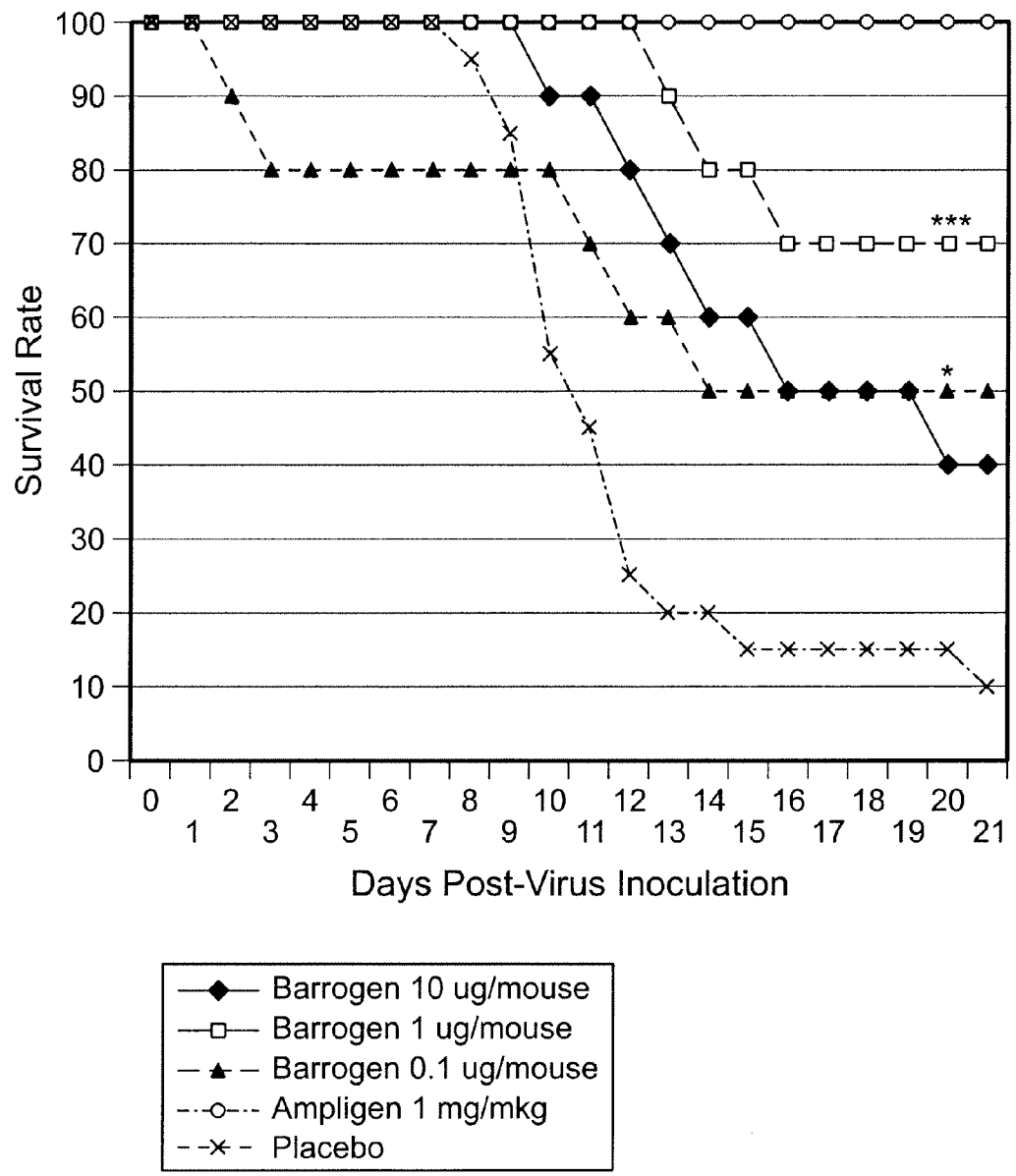

Results:

Treatment with Barrogen was able to significantly improve survival in Banzi virus inoculated mice (see Table 8, FIG. 21). From a survival rate of 10% in placebo treated animals Barrogen treatment increased survival to 70% (p<0.001) in animals receiving a dose of 1 μg/mouse and 50% (p<0.05) in animals receiving 0.1 μg/mouse.

Animals receiving 10 μg/mouse had 40% survival, which was not significantly higher than placebo treated animals. The positive control agent Ampligen® performed as expected, producing 100% survival (p<0.001).

TABLE 8

Animals: Female 18-21 g BALB/c mice
Virus: Banzi virus (strain H336)
Drug diluent: Provided by Sponsor (Sterile Water for Ampligen)
Treatment schedule: an initial dose administered 4-6 h
pre-virus exposure, with one additional dose administered 48
hr later (Ampligen: A single dose administered 24 h
pre-virus exposure)
Treatment route: i.p.
Expt. Duration: 21 days

| Compound | Dose (μg/mouse/day) | Uninfected toxicity control Surv/Total | Infected, treated Surv/Total | MDD[a] ± SD |
|---|---|---|---|---|
| Barrogen | 10 | 3/3 (100%) | 4/10 (40%) | 14.2 ± 3.5 |
| Barrogen | 1 | 3/3 (100%) | 7/10 (70%)*** | 14.3 ± 1.5 |
| Barrogen | 0.1 | 3/3 (100%) | 5/10 (50%)* | 8.4 ± 5.5 |
| Ampligen | 1 mg/kg | 3/3 (100%) | 10/10 (100%)*** | — |
| Placebo | — | 3/3 (100%) | 2/20 (10%) | 11.4 ± 2.9 |
| Normal Controls | — | 3/3 (100%) | — | — |

[a]Mean day to death of mice dying before day 21
*P < 0.05,
***P < 0.001 compared to placebo-treated controls.

Figure 22:
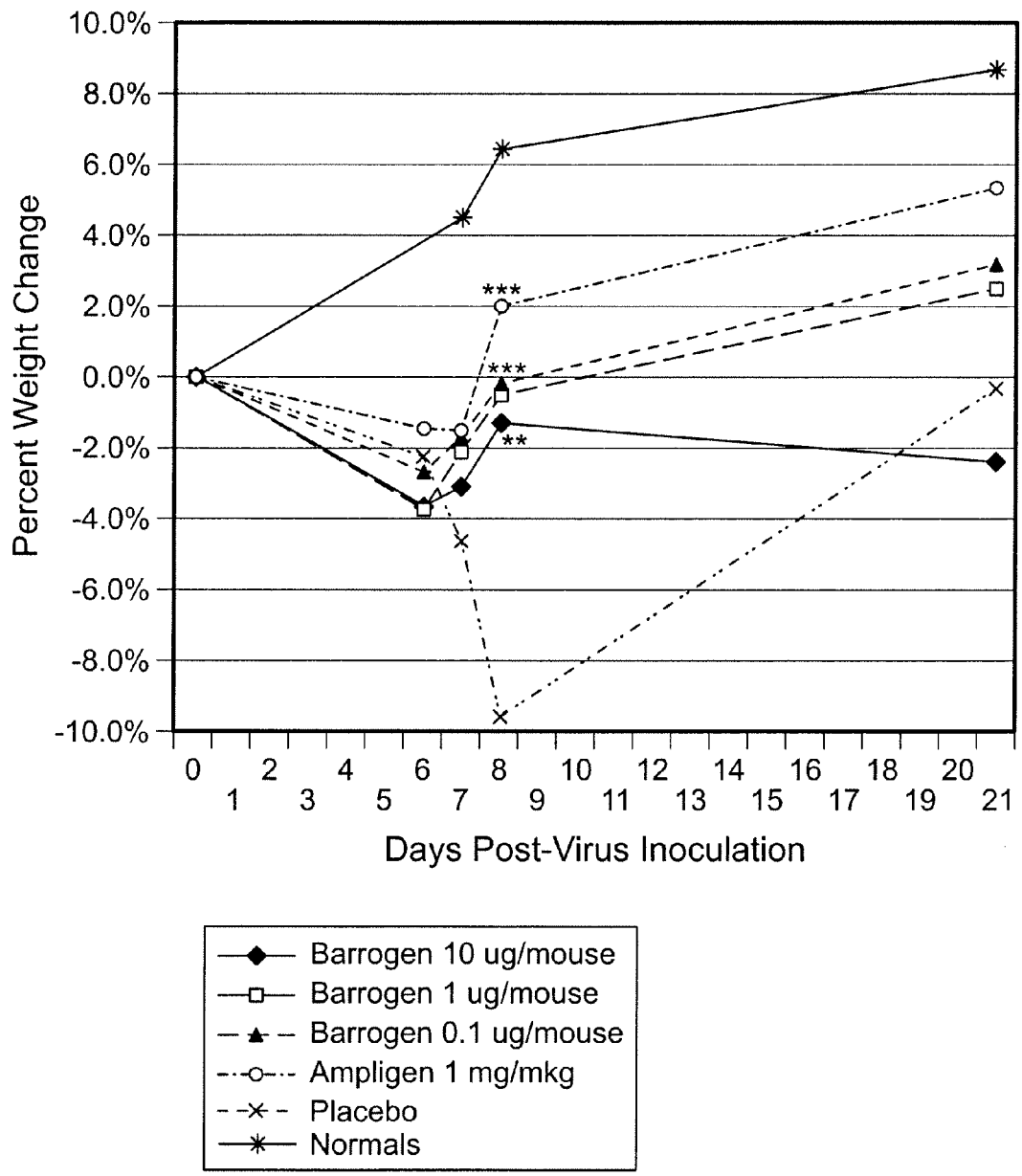
Figure 23:
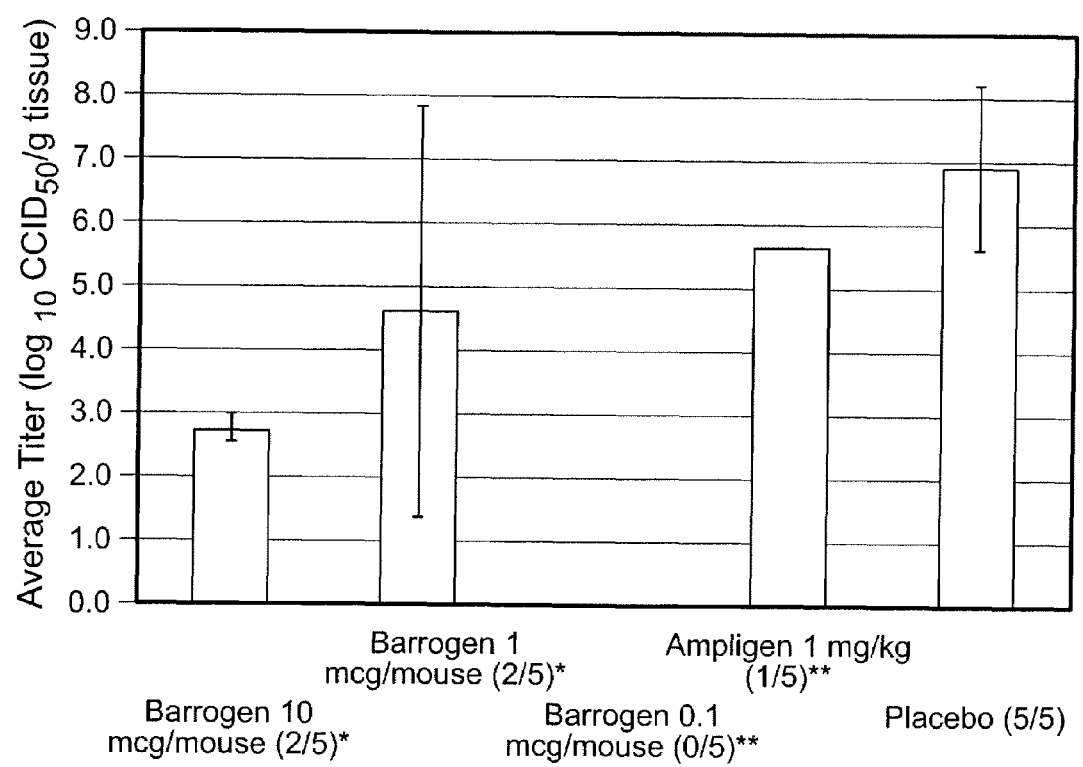
Figure 24:
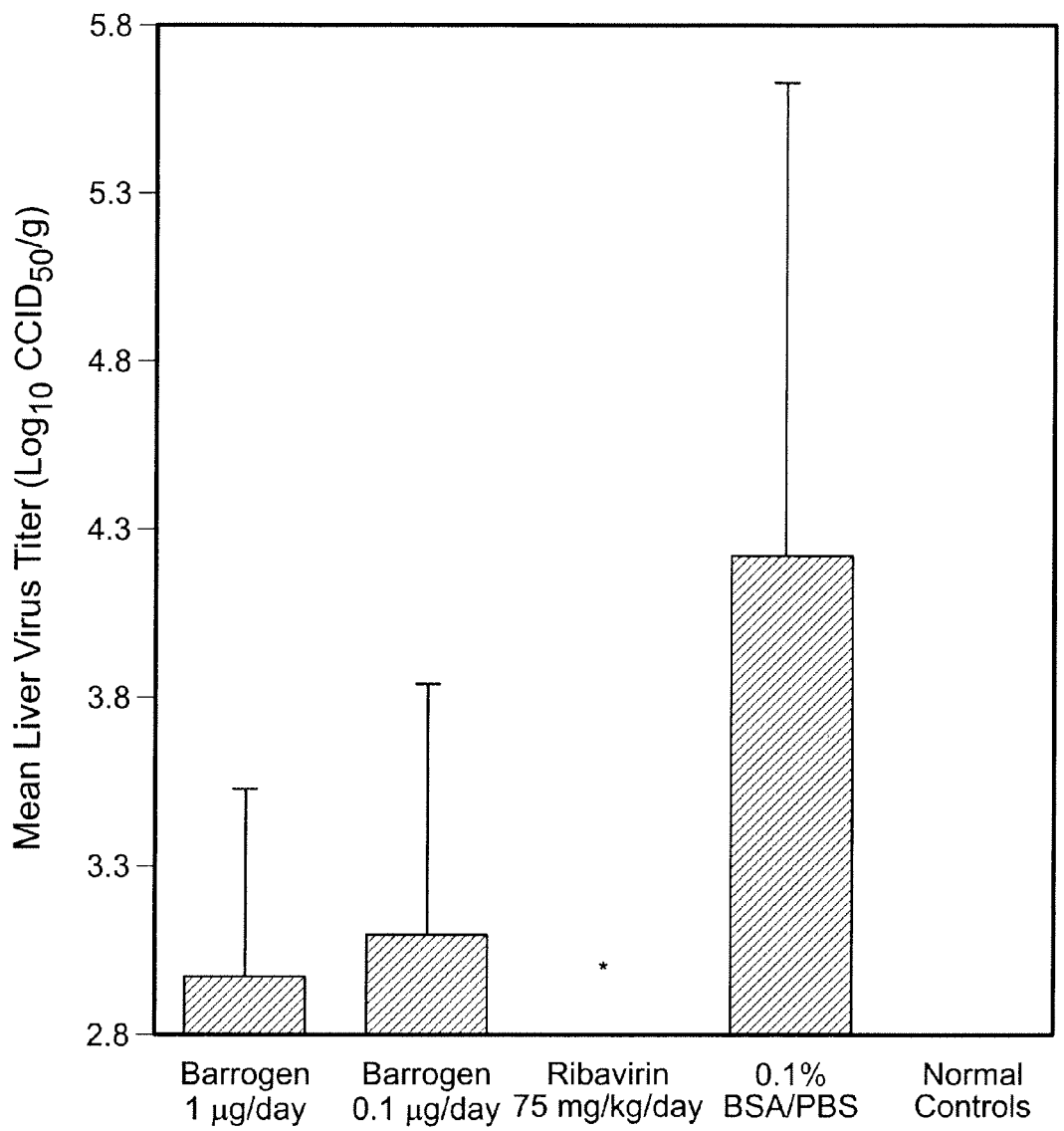
Figure 25:
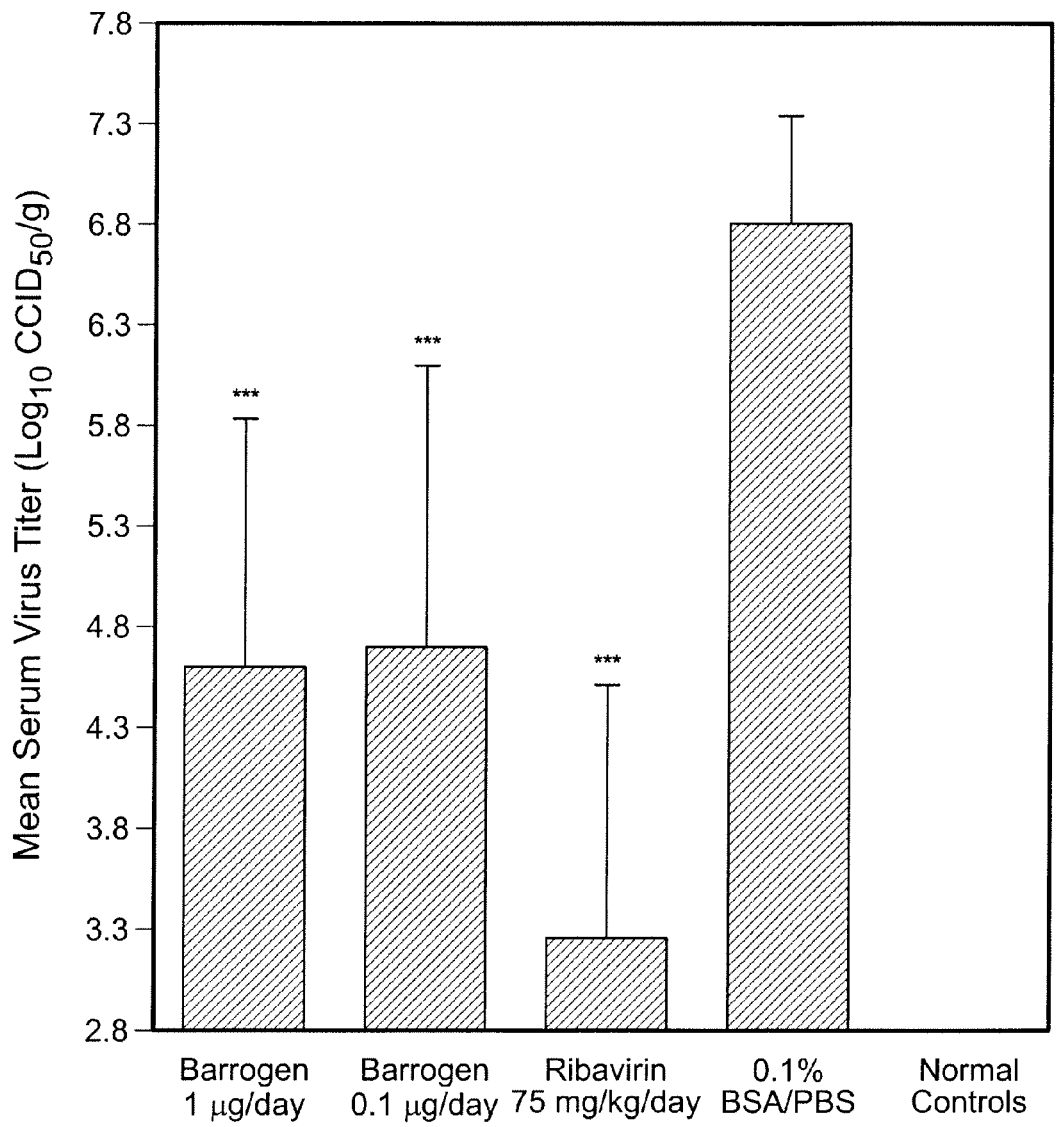
Figure 26:
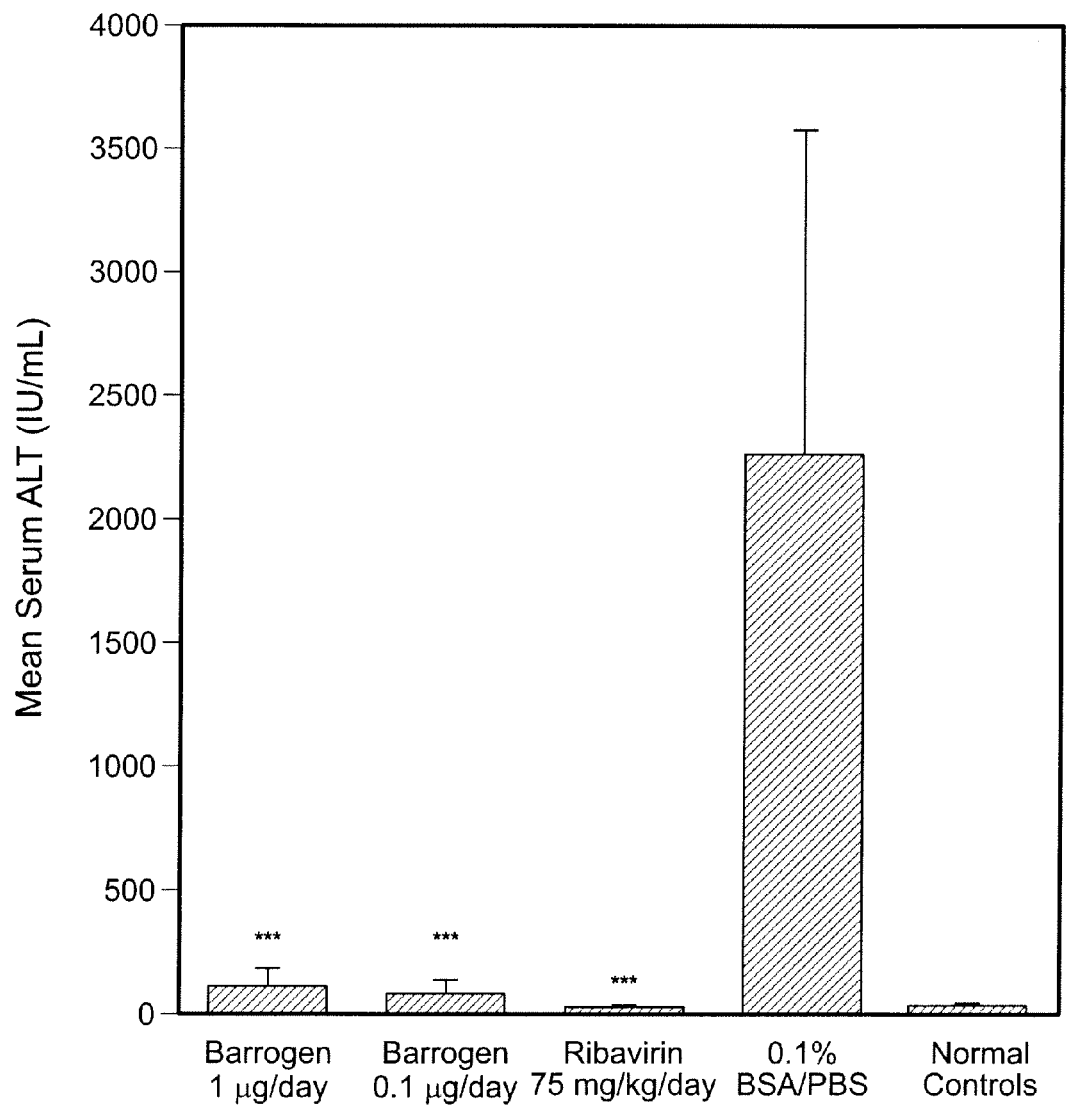
Figure 27:
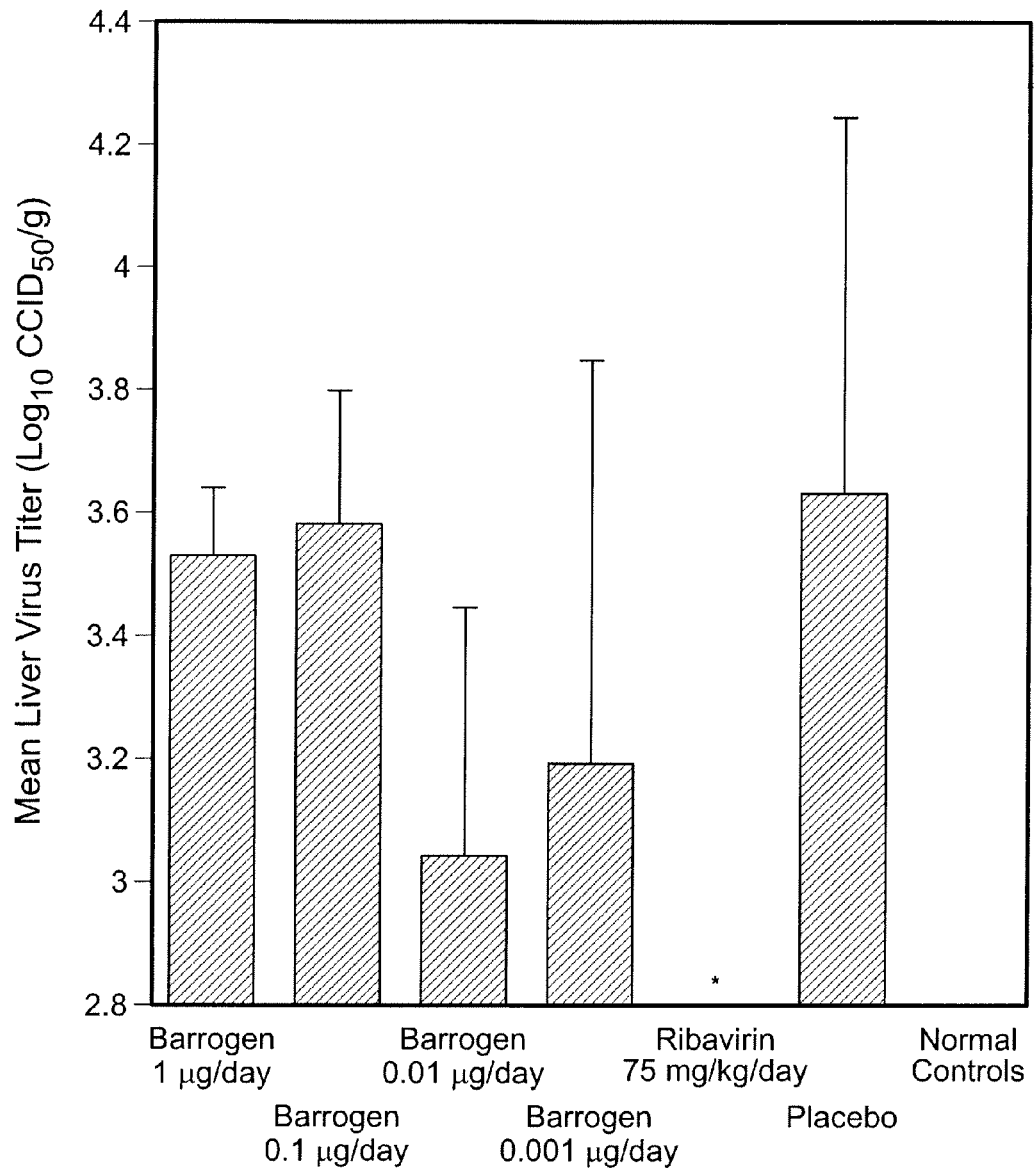
Figure 28:
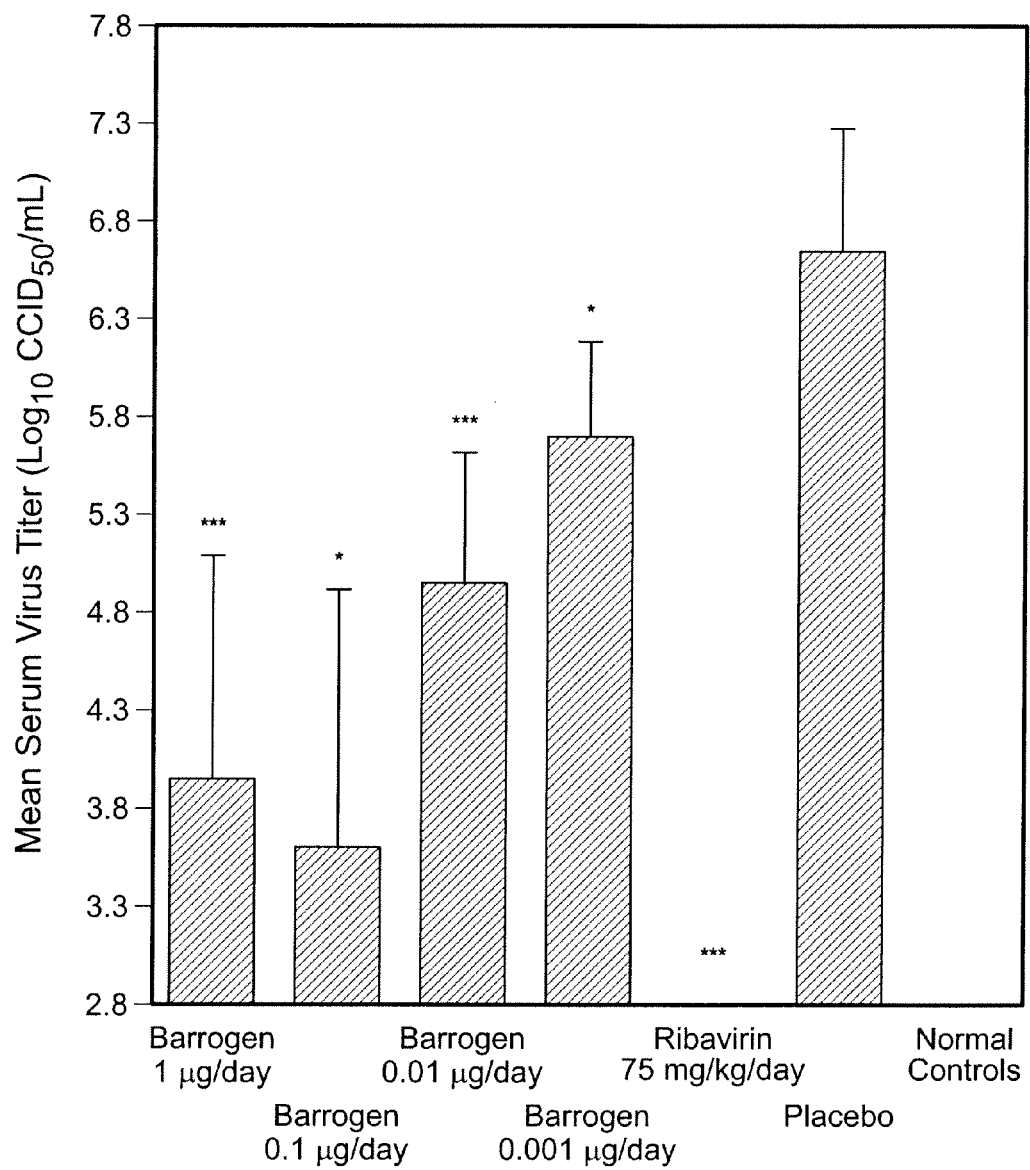
Figure 29:
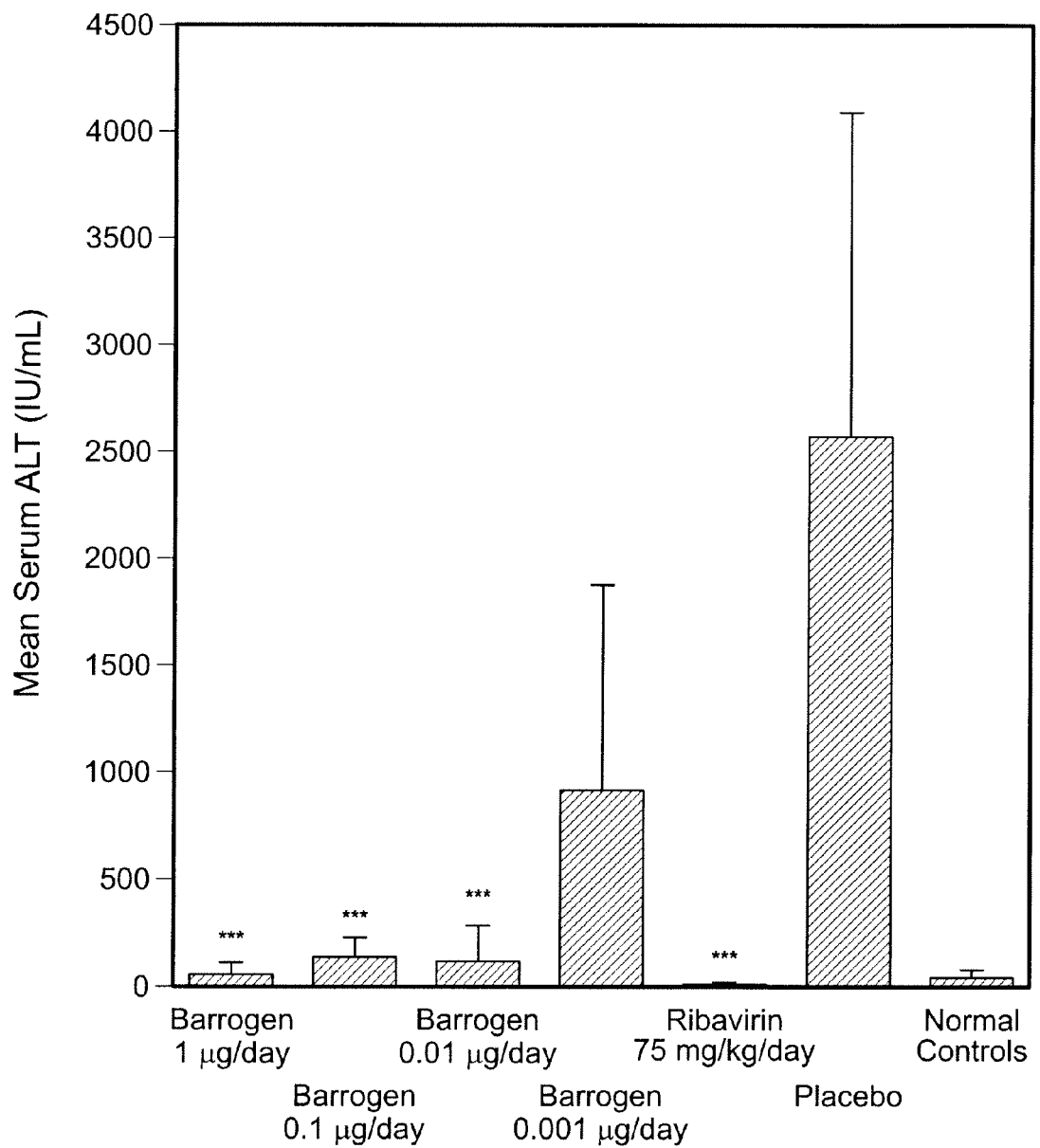
Figure 30:
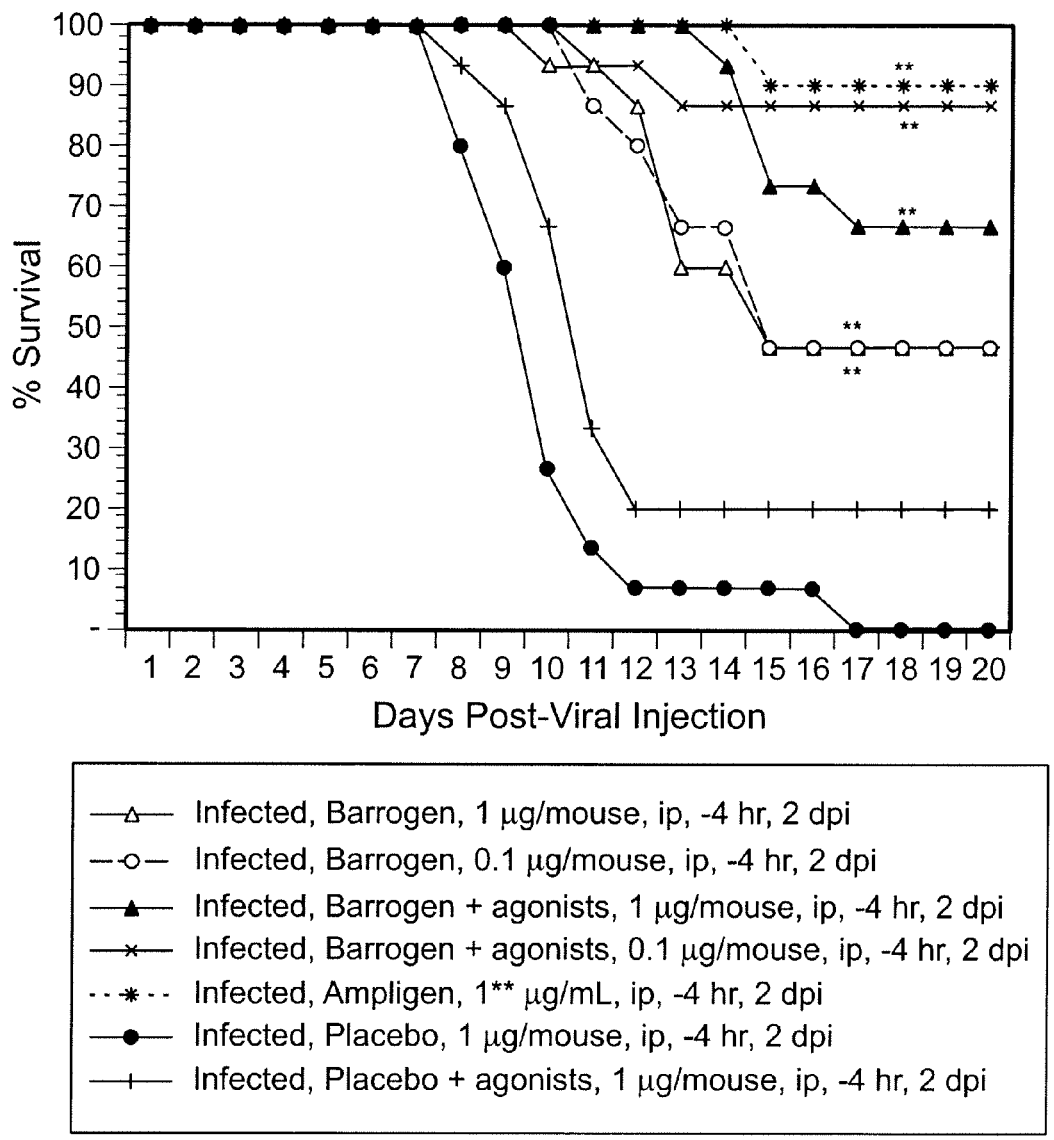
Figure 31:
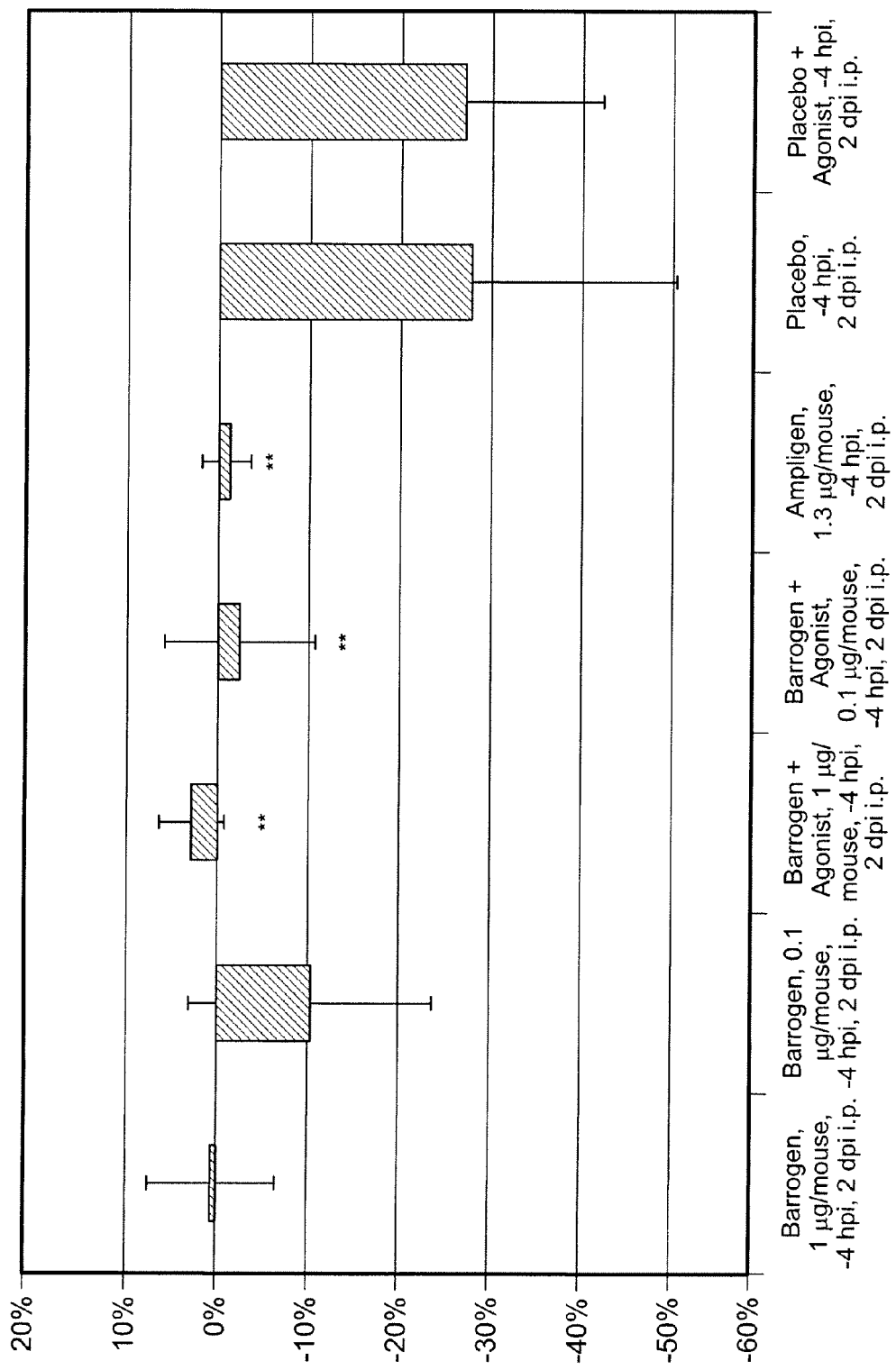

Barrogen treatment was also able to significantly ameliorate weight loss associated with viral infection. On 8 dpi placebo treated animals had lost an average of 9.6% of their initial weight (see FIG. 22). This is in comparison to a weight loss of 1.3% in animals receiving 10 μg/mouse (p<0.05), 0.5% weight loss in animals dosed with 1 μg/mouse (p<0.001), and 0.2% weight loss in animals receiving 0.1 μg/mouse (p<0.001). Ampligen® treated mice had an average weight gain of 1.9% by 8 dpi (p<0.001). In comparison non-infected untreated control mice (i.e. normal mice) had an average weight of 4.6% over the same time period.

Treatment with Barrogen was also able to significantly reduce the number of mice in which virus was detected, as well as reducing viral titers in the brains of mice. Banzi virus was detected in the brains of all 5 placebo mice assayed, with an average titer of 6.9 $\log_{10}$ CCID50/g of tissue. In contrast, virus was detected in 2 out of 5 animals in mice treated with either 10 or 1 μg/mouse of Barrogen (p<0.05). Average brain titers were 2.8 and 4.6 $\log_{10}$ CCID50, respectively. No virus was detected in the brains of mice treated with 0.1 μg/mouse of Barrogen (p<0.01). Ampligen® worked as expected, with virus detected in only 1 of the 5 assayed, with a titer of 5.6 (p<0.01).

Treatment with Barrogen was able to improve the condition of animals in all parameters measured here, namely mortality, viral induced weight loss, and brain viral titers. Treatment with the highest dose used here (10 μg/mouse) did not significantly improve survival, and was not as effective at ameliorating weight loss, indicating that there may be some mild form of toxicity noted at higher doses.

The improvement in weight change seen with treatment of 1 or 0.1 μg/mouse and its association with improved survival is consistent with our previous experience in Banzi virus in which dramatic weight loss is an indicator of a poor outcome.

Therefore, any improvement in viral associated weight change is a potentially positive sign of efficacy.

Example 8

Effect of the Combination of Barrogen and Oseltamivir on Influenza A Virus Infection in Mice Barrogen can be used to enhance the antiviral efficacy of low dosages of Oseltamivir. Barrogen is an immunomodulating agent that has a consistent inhibitory effect against influenza virus infections in mice. Oseltamivir (Tamiflu™) is an orally effective influenza neuraminidase inhibitor that we have shown to be highly active against influenza virus infections in mice down to doses approaching 1 mg/kg/day.

To study the immunomodulatory effect of Barrogen, mice infected with Influenza A/NWS/33 (H1N1) virus can be treated with either Barrogen (1 μg/injection), Oseltamivir (1, 0.32, or 0.1 mg/kg/day) or with a combination of the two drugs. Barrogen can be given i. p. 4 h post-virus exposure. Oseltamivir can be given p. o. bid×5 (by mouth twice a day for five days) beginning 4 h post-virus exposure. Parameters for evaluation can include prevention or slowing of death, and lessening of $SaO_2$ decline.

Example 9

Effect of Barrogen and Barrogen Plus Agonist Cocktail on Survival in Mice Infected with Banzi Virus Introduction Barrogen is a protein produced by the intestinal protozoan Eimeria. This protein stimulates the release of IL-12 from dendritic cells and has antitumor properties. It has also been shown previously to moderately increase survival of mice infected with Banzi virus. Barrogen, injected simultaneously with GM-CSF, has been shown to improve survival in tumor mouse models over Barrogen treatment alone. This example tested whether an agonist cocktail of immunostimulatory agents, containing GM-CSF, IFN-γ, IL-2, and anti-CD40, would also improve survival of Banzi-infected mice.

Materials and Methods

Animals. Female Balb/c mice with aged 5-6 weeks were used. Animals were randomly assigned to cages and individually marked with eartags.

Test Article: Barrogen and Barrogen plus agonist cocktail, along with the respective placebo controls, were supplied by Barros Research Institute as an aqueous solution ready for injection. Barrogen was stored at 4° C. until use. A volume of 0.4 ml/mouse was injected intraperitoneally to provide a maximum dose of 1 μg/treatment for Barrogen. Barrogen diluent consisted of 0.1% BSA in PBS.

The immunostimulatory agents in the agonist cocktail co-administered with Barrogen were all obtained from R&D Systems (Minneapolis, Minn.). All solutions were prepared in 0.1% BSA in PBS. The final dose of each agonist was 20 ng/treatment for GM-CSF, 20 ng/treatment for IL-2, 60 ng/treatment for IFN-γ, and 2 microgram/treatment for anti-CD40.

Banzi virus: The H336 strain of Banzi virus was obtained from ATCC and used after 3 passages in Vero cells. A $10_{-3}$ dilution of the virus was prepared, and animals were injected intraperitoneally with 0.1 ml of the diluted virus.

Experimental design: Mice were treated intraperitoneally 4 hr before viral injection and again 2 days post-viral challenge. Barrogen diluent or Barrogen diluent plus agonist cocktail was used as a placebo control for Barrogen or Barrogen plus agonist cocktail treatment, respectively. Group descriptions and numbers of animals per group are shown in Table 9. Percent survival and mean weight change were calculated based on the number of animals still alive 21 days post-viral injection and the weight difference between days 0 and 10 post-viral injection.

Results and Discussion

Barrogen, at a dose of 1 μg/treatment, when given −4 hpi and 2 dpi, significantly reduced mortality in Banzi-infected female Balb/c mice (Table 9). There was also a significant increase in mean-day-to-death in Barrogen-treated mice, as compared with placebo-treated mice (FIG. 30). Protection was similar to the protection observed in previous experiments with Barrogen. No toxicity was observed in uninfected mice treated with Barrogen as determined by weight loss or fur ruffling. Weight loss in Banzi-infected, Barrogen-treated animals was not significantly reduced as compared with weight loss in placebo-treated animals (FIG. 31), which was probably due to the small number of placebo-treated controls surviving to 10 dpi (n=4).

Mice treated with Barrogen together with an agonist cocktail had a significant increase in survival as compared to mice treated with placebo plus agonist (Table 9) as well as an increase in mean-day-to-death (FIG. 30). Barrogen plus agonist (0.1 μg/treatment) treatment was also moderately significant as compared to Barrogen treatment alone ($P<0.05$, data not shown). Placebo plus agonist treatment also had a moderately significant extension of mean-day-to-death when compared with placebo treatment alone ($P<0.05$, data not shown). Weight loss was also significantly reduced in Barrogen plus agonist-treated mouse groups as compared with placebo plus agonist treatment (FIG. 31).

Barrogen elicits the production of IL-12 as well as other inflammatory cytokines and has been shown to have anti-tumor properties in mice (Rosenberg et al, 2005, Int'l J Cancer 114, 756-65). Production of IL-12 can result in many downstream events including induction of IFN-γ production by NK cells (Ellermann-Eriksen, 2005, Virol J 2, 59) and downregulation of the Th2 response (Rollier et al, 2005, J Infect Dis 192, 920-29). IL-12 may be helpful in clearance of viral infection, but has been shown to not be necessary for the resolution of VSV and MCMV (Dix et al, 2004, Curr HIV Res 2, 333-42; Ireland et al, 2005, Viral Immunol 18, 397-402). Co-treatment with Barrogen and other inflammatory cytokines may allow for a greater stimulation of an early immune response. Stimulation of an early immune response has been shown to be important for clearance of West Nile virus infection (Diamond et al, 2003, J Exp Med 198, 1853-62).

Conclusions

1. Barrogen at 1 and 0.1 μg/treatment (i.p., −4 hpi and 2 dpi) in 6-7 week-old female Balb/c mice infected with Banzi virus significantly improved survival and mean day-to-death.
2. Barrogen at 1 and 0.1 μg/treatment treated in combination with an agonist cocktail (i.p., −4 hpi and 2 dpi) in 6-7 week-old female Balb/c mice infected with Banzi virus significantly improved survival and mean day-to-death, and significantly decreased weight loss.
3. Treatment with agonist cocktail containing GM-CSF, IFN-γ, IL-2, and anti-CD40, resulted in a moderately significant improvement in mean-day-to-death as compared with placebo treatment.

TABLE 9

Effect of Barrogen on survival and weight change of 5-6 week-old Balb/c mice infected with Banzi virus
Animals: Female 17-19 g Balb/c mice.
Virus: Banzi virus (H336 strain), 100 $CCID_{50}$
Virus route: intraperitoneal injection
Duration of experiment: 21 days
Drug diluent: Barrogen diluent**

| | | | Toxicity controls | | Infected, treated | |
|---|---|---|---|---|---|---|
| Treatment | Dosage | Route, schedule | % survival (alive/total) | % Mean wt. change (g)[a] | % survival (alive/total) | % Mean wt. change (g) |
| Barrogen | 1 μg/treatment | i.p. 1 injection −4 hpi and 2 dpi | 100% (3/3) | 0.4 | 47% (7/15)** | −1.0 |
| | 0.1 μg/treatment | i.p. 1 injection −4 hpi and 2 dpi | — | — | 47% (7/15)** | −1.4 |
| Barrogen + agonist | 1 μg/treatment | i.p. 1 injection −4 hpi and 2 dpi | 100% (3/3) | −0.3 | 67% (10/15)* | 0.5*** |
| | 0.1 μg/treatment | i.p. 1 injection −4 hpi and 2 dpi | — | — | 87% (13/15)*** | −0.3*** |
| Placebo | — | i.p. 1 injection −4 hpi and 2 dpi | 100% (3/3) | 1.0 | 0% (0/15) | −3.5 |
| Placebo + agonist | — | i.p. 1 injection −4 hpi and 2 dpi | 100% (3/3) | 0.7 | 20% (3/15) | −3.5 |

[a]Statistics were done by comparing the weights of individual mice on day 0 and day 10 post-viral injection.
***P ≦ 0.001, compared with placebo.
**P ≦ 0.005, compared with placebo.
*P ≦ 0.01, compared with placebo.

REFERENCES CITED AND EQUIVALENTS

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for treating a disease, disorder or condition associated with a Punta Toro virus infection in a subject, or reducing the lethality of a disease, disorder or condition associated with a Punta Toro virus infection in a subject, which method comprises administering to the subject an effective amount of a pharmaceutical composition comprising an Apicomplexa-related protein (ARP) comprising SEQ ID NO:20, wherein the composition is administered according to a dosing and resting regimen.

2. The method of claim 1, wherein the dosing and resting regimen starts after suspected exposure to Punta Toro virus or after onset of a symptom associated with the viral infection.

3. The method of claim 1, wherein the ARP is administered in a range selected from the group consisting of 0.0001 to 100, 0.0005-0.001, 0.001-0.01, 0.01-0.1, 0.1-1, 1-10, and 10-100 μg per kg body weight of the subject.

4. The method of claim 1, wherein the ARP is administered in the range of from 0.0001-0.001 μg per kg body weight of the subject.

5. The method of claim 4, wherein the ARP is administered at 0.00014 μg per kg body weight of the subject and the subject is a human.

6. The method of claim 1, wherein the pharmaceutical composition is administered to the subject at least once within a week of the day of suspected exposure to Punta Toro virus or the onset of a symptom associated with the Punta Toro virus infection.

7. The method of claim 1, wherein the dosing and resting regimen is once weekly for at least a month starting within one week of suspected exposure to Punta Toro virus or the onset of a symptom associated with Punta Toro virus infection.

8. The method of claim 1, wherein the dosing and resting regimen comprises a first dose administered to the subject daily for a week starting on the day of suspected exposure to Punta Toro virus or the onset of a symptom associated with a Punta Toro virus infection and a second dose administered to the subject daily for a week at least once every other week after administration of the first dose.

9. The method of claim 1, wherein the dosing and resting regimen comprises a first dose administered to the subject on the day of suspected exposure to Punta Toro virus or the onset of a symptom associated with a Punta Toro virus infection and a second dose administered to the subject at least once every 3 days after administration of the first dose.

10. The method of claim 1, wherein the pharmaceutical composition is administered intraperitoneally.

11. The method of claim 1, wherein the pharmaceutical composition is administered intranasally, orally, or rectally.

12. The method of claim 1, wherein the pharmaceutical composition is administered subcutaneously.

13. The method of claim 1, wherein the pharmaceutical composition is administered intramuscularly or intravenously.

14. The method of claim 1, wherein the pharmaceutical composition is administered conjointly with an effective amount of at least one immunostimulatory agent.

15. The method of claim 14, wherein at least one immunostimulatory agent is selected from the group consisting of GM-CSF and IL-18.

16. The method of claim 14, wherein at least one immunostimulatory agent is selected from the group consisting of G-CSF, anti-CD40, IFN-γ, FLT-3 ligand, IFN α/β, TNF-α/β, MCP-1, IL-1, IL-2, IL-4, and IL-6.

17. The method of claim 14, wherein the at least one immunostimulatory agent is administered in a range selected from the group consisting of 0.001-0.01, 0.01-0.1, 0.1-1, 1-10, 10-100, 100-1000, 1000-10000, and 10000-100000 μg per kg body weight of the subject.

18. The method of claim 14, wherein the immunostimulatory agent is administered intraperitoneally, intranasally, subcutaneously, intramuscularly, intravenously, orally or rectally.

19. A method of treating a disease, disorder or condition associated with a Punta Toro virus infection, or reducing the lethality of a disease, disorder or condition associated with a Punta Toro virus infection in a subject, which method comprises administering to the subject an effective amount of a pharmaceutical composition comprising an ARP comprising a sequence that is at least 85% identical to SEQ ID NO:20, wherein the composition is administered according to a dosing and resting regimen.

20. The method of claim 19, wherein the ARP comprises a sequence that is at least 90% identical to SEQ ID NO:20.

21. The method of claim 19, wherein the ARP comprises a sequence that is at least 95% identical to SEQ ID NO:20.

22. The method of claim 19, wherein the ARP comprises SEQ ID NO:1 or SEQ ID NO:2.

23. The method of claim 1, wherein the ARP is purified.

24. The method of claim 19, wherein the ARP is purified.

25. A method for treating a disease, disorder or condition associated with a Rift Valley Fever virus infection or Sandfly Fever virus infection in a subject, or reducing the lethality of a disease, disorder or condition associated with a Rift Valley Fever virus infection or Sandfly Fever virus infection in a subject, which method comprises administering to the subject an effective amount of a pharmaceutical composition comprising an Apicomplexa-related protein (ARP) comprising SEQ ID NO:20, wherein the composition is administered according to a dosing and resting regimen.

26. The method of claim 25, wherein the dosing and resting regimen starts within a week of suspected exposure to the Rift Valley Fever virus or Sandfly virus or onset of a symptom associated with the viral infection.

27. The method of claim 25, wherein the ARP is administered in a range selected from the group consisting of 0.0001 to 100, 0.0005-0.001, 0.001-0.01, 0.01-0.1, 0.1-1, 1-10, and 10-100 μg per kg body weight of the subject.

28. The method of claim 25, wherein the ARP is administered in the range of from 0.0001-0.001 μg per kg body weight of the subject.

29. The method of claim 28, wherein the ARP is administered at 0.00014 μg per kg body weight of the subject and the subject is a human.

30. The method of claim 25, wherein the dosing and resting regimen is once weekly for at least a month starting on the suspected day of infection or the onset of a symptom associated with the viral infection.

31. The method of claim 25, wherein the dosing and resting regimen comprises a first dose administered to the subject daily for a week starting on the suspected day of infection or the onset of a symptom associated with the viral infection and a second dose administered to the subject daily for a week at least once every other week after administration of the first dose.

32. The method of claim 25, wherein the dosing and resting regimen comprises a first dose administered to the subject on the suspected day of infection or the onset of a symptom associated with an acute viral infection and a second dose administered to the subject at least once every 3 days after administration of the first dose.

33. The method of claim 25, wherein the pharmaceutical composition is administered intraperitoneally.

34. The method of claim 25, wherein the pharmaceutical composition is administered intranasally, orally, or rectally.

35. The method of claim 25, wherein the pharmaceutical composition is administered subcutaneously.

36. The method of claim 25, wherein the pharmaceutical composition is administered intramuscularly or intravenously.

37. The method of claim 25, wherein the pharmaceutical composition is administered conjointly with an effective amount of at least one immunostimulatory agent.

38. The method of claim 37, wherein at least one immunostimulatory agent is selected from the group consisting of GM-CSF and IL-18.

39. The method of claim 37, wherein at least one immunostimulatory agent is selected from the group consisting of G-CSF, anti-CD40, IFN-γ, FLT-3 ligand, IFN α/β, TNF-α/β, MCP-1, IL-1, IL-2, IL-4, and IL-6.

40. The method of claim 37, wherein the at least one immunostimulatory agent is administered in a range selected from the group consisting of 0.001-0.01, 0.01-0.1, 0.1-1, 1-10, 10-100, 100-1000, 1000-10000, and 10000-100000 μg per kg body weight of the subject.

41. The method of claim 37, wherein the immunostimulatory agent is administered intraperitoneally, intranasally, subcutaneously, intramuscularly, intravenously, orally or rectally.

42. A method of treating a disease, disorder or condition associated with a Rift Valley Fever virus infection or Sandfly Fever virus infection, or reducing the lethality of a disease, disorder or condition associated with a Rift Valley Fever virus infection or Sandfly Fever virus infection in a subject, which method comprises administering to the subject an effective amount of a pharmaceutical composition comprising an ARP comprising a sequence that is at least 85% identical to SEQ ID NO:20, wherein the composition is administered according to a dosing and resting regimen.

43. The method of claim 42, wherein the ARP comprises a sequence that is at least 90% identical to SEQ ID NO:20.

44. The method of claim 42, wherein the ARP comprises a sequence that is at least 95% identical to SEQ ID NO:20.

45. The method of claim 42, wherein the ARP comprises SEQ ID NO:1 or SEQ ID NO:2.

46. The method of claim 25, wherein the ARP is purified.

47. The method of claim 42, wherein the ARP is purified.

48. The method of claim 1, wherein the ARP consists of SEQ ID NO:20.

49. The method of claim 19, wherein the ARP consists of SEQ ID NO:1, SEQ ID NO:2, or SEQ ID NO:20.

50. The method of claim 25, wherein the ARP consists of SEQ ID NO:20.

51. The method of claim 42, wherein the ARP consists of SEQ ID NO:1, SEQ ID NO:2 or SEQ ID NO:20.

52. The method of claim 1, wherein the dosing and resting regimen starts before exposure or suspected exposure to a Punta Toro virus.

53. The method of claim 19, wherein the dosing and resting regimen starts before exposure or suspected exposure to a Punta Toro virus.

54. The method of claim 25, wherein the dosing and resting regimen starts before exposure or suspected exposure to a Rift Valley Fever virus or Sandfly Fever virus.

55. The method of claim 42, wherein the dosing and resting regimen starts before exposure or suspected exposure to a Rift Valley Fever virus or Sandfly Fever virus.

* * * * *